(12) United States Patent
Luengo et al.

(10) Patent No.: US 11,524,962 B2
(45) Date of Patent: Dec. 13, 2022

(54) SUBSTITUTED PYRROLO[2,3-D]PYRIMIDINES AS INHIBITORS OF PROTEIN ARGININE METHYL TRANSFERASE 5 (PRMT5)

(71) Applicant: PRELUDE THERAPEUTICS, INCORPORATED, Wilmington, DE (US)

(72) Inventors: Juan Luengo, Phoenixville, PA (US); Hong Lin, Exton, PA (US); Michael Hawkins, Ambler, PA (US)

(73) Assignee: Prelude Therapeutics, Incorporated, Wilmington, DE (US)

( * ) Notice: Subject to any disclaimer, the term of this patent is extended or adjusted under 35 U.S.C. 154(b) by 31 days.

(21) Appl. No.: 16/758,629

(22) PCT Filed: Oct. 26, 2018

(86) PCT No.: PCT/US2018/057813
§ 371 (c)(1),
(2) Date: Apr. 23, 2020

(87) PCT Pub. No.: WO2019/084470
PCT Pub. Date: May 2, 2019

(65) Prior Publication Data
US 2021/0403472 A1    Dec. 30, 2021

Related U.S. Application Data

(60) Provisional application No. 62/577,448, filed on Oct. 26, 2017, provisional application No. 62/666,724, filed on May 4, 2018.

(51) Int. Cl.
| | | |
|---|---|---|
| *A61K 31/519* | (2006.01) | |
| *C07D 487/04* | (2006.01) | |
| *A61P 35/00* | (2006.01) | |
| *A61K 45/06* | (2006.01) | |

(52) U.S. Cl.
CPC ............ *C07D 487/04* (2013.01); *A61K 45/06* (2013.01); *A61P 35/00* (2018.01)

(58) Field of Classification Search
CPC ............................ A61K 31/519; C07D 487/04
USPC ........................................ 514/258.1; 544/253
See application file for complete search history.

(56) References Cited

U.S. PATENT DOCUMENTS

2016/0244475 A1    8/2016   Tatlock et al.

FOREIGN PATENT DOCUMENTS

| WO | 2016178870 A1 | 11/2016 |
|---|---|---|
| WO | 2017032840 A1 | 3/2017 |
| WO | 2017153186 A1 | 9/2017 |
| WO | 2017212385 A1 | 12/2017 |
| WO | 2018065365 A1 | 4/2018 |
| WO | 2018152548 A1 | 8/2018 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
International Search Report and Written Opinion issued in PCT/US2018/057813, dated Jan. 15, 2019.
International Preliminary Report on Patentability and Written Opinion issued in PCT/US2018/057813, dated May 7, 2020.

\* cited by examiner

*Primary Examiner* — Douglas M Willis
(74) *Attorney, Agent, or Firm* — BakerHostetler

(57) ABSTRACT

The disclosure is directed to compounds of Formula (I) and Formula (II). Formula (I) and Formula (II) and pharmaceutically acceptable salts or solvates thereof. Pharmaceutical compositions comprising compounds of Formula (I) or Formula (II), as well as methods of their use and preparation, are also described.

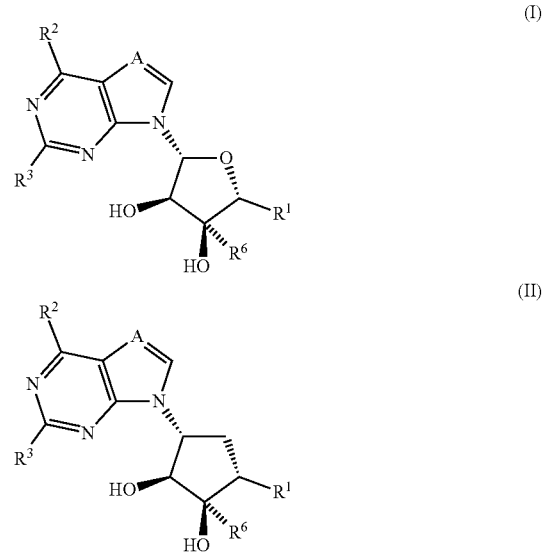

23 Claims, 1 Drawing Sheet

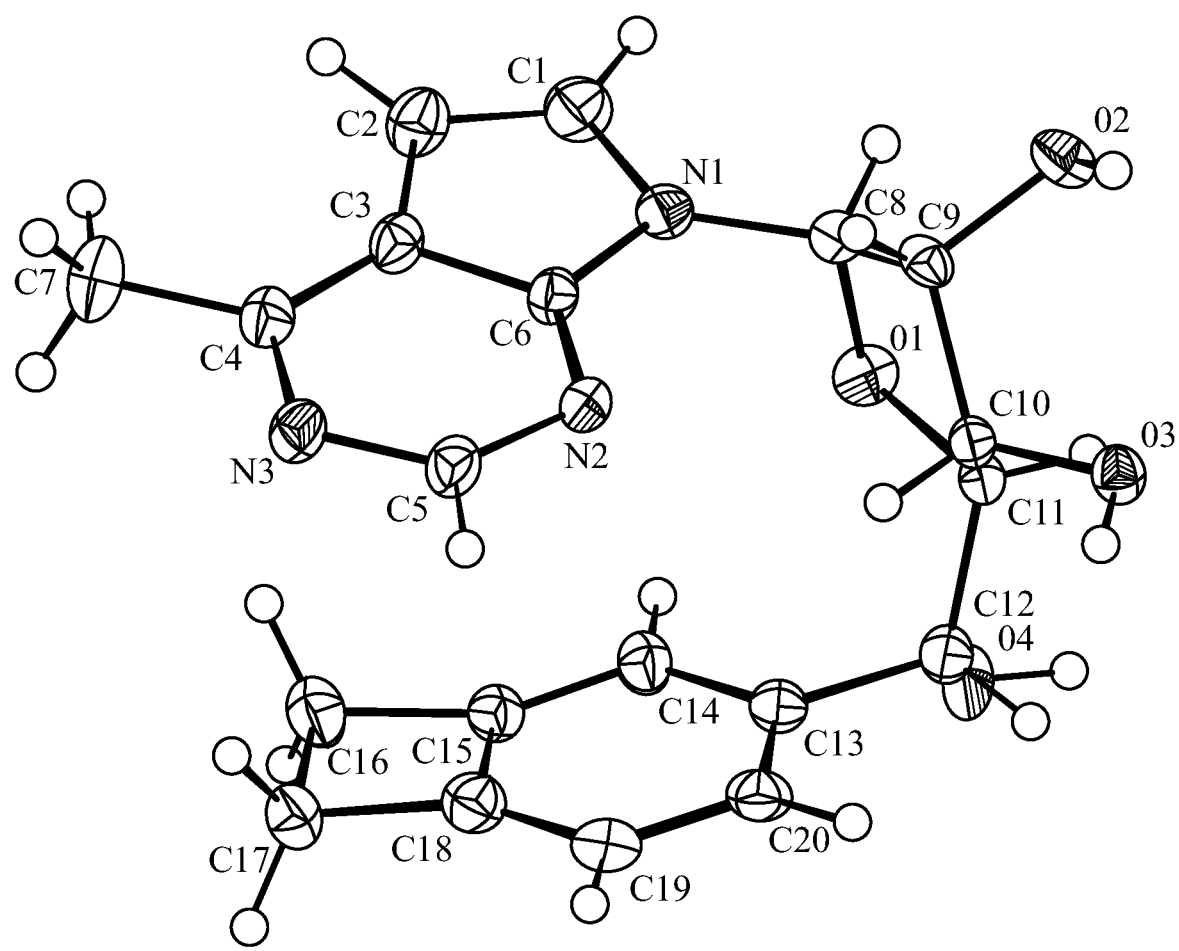

SUBSTITUTED PYRROLO[2,3-D]PYRIMIDINES AS INHIBITORS OF PROTEIN ARGININE METHYL TRANSFERASE 5 (PRMT5)

CROSS-REFERENCE TO RELATED APPLICATIONS

This application is the United States National Stage Application of International Patent Application No. PCT/US2018/057813 filed Oct. 26, 2018, which claims the benefit of priority to U.S. Provisional Application No. 62/577,448, filed on Oct. 26, 2017, and to U.S. Provisional Application No. 62/666,724, filed on May 4, 2018. Each of these applications is incorporated by reference herein in its entirety.

TECHNICAL FIELD

The disclosure is directed to PRMT5 inhibitors and methods of their use.

BACKGROUND

Protein arginine methylation is a common post-translational modification that regulates numerous cellular processes, including gene transcription, mRNA splicing, DNA repair, protein cellular localization, cell fate determination, and signaling. Three types of methyl-arginine species exist: ω NG monomethylarginine (MMA), ω NG, NG asymmetric dimethylarginine (ADMA) and ω NG,N'G symmetric dimethylarginine (SDMA). The formation of methylated arginines is catalyzed by the protein arginine methyl transferases (PRMTs) family of methyltransferases. Currently, there are nine PRMTs annotated in the human genome The majority of these enzymes are Type I enzymes (PRMT1,-2,-3,-4,-6,-8) that are capable of mono- and asymmetric dimethylation of arginine, with S-adenosylmethionine (SAM) as the methyl donor. PRMT-5,-7 and-9 are considered to be Type II enzymes that catalyze symmetric dimethylation of arginines. Each PRMT species harbors the characteristic motifs of seven beta strand methyltransferases (Katz et al., 2003), as well as additional "double E" and "THW" sequence motifs particular to the PRMT subfamily.

PRMT5 is as a general transcriptional repressor that functions with numerous transcription factors and repressor complexes, including BRG1 and hBRM, Blimp1, and Snail. This enzyme, once recruited to a promoter, symmetrically dimethylates H3R8 and H4R3. Importantly, the H4R3 site is a major target for PRMT1 methylation (ADMA) and is generally regarded as a transcriptional activating mark. Thus, both H4R3me2s (repressive; me2s indicates SDMA modification) and H4R3me2a (active; me2a indicates ADMA modification) marks are produced in vivo. The specificity of PRMT5 for H3R8 and H4R3 can be altered by its interaction with COPR5 and this could perhaps play an important role in determining PRMT5 corepressor status.

Role of PRMTs in Cancer

Aberrant expression of PRMTs has been identified in human cancers, and PRMTs are considered to be therapeutic targets. Global analysis of histone modifications in prostate cancer has shown that the dimethylation of histone H4R3 is positively correlated with increasing grade, and these changes are predictive of clinical outcome.

PRMT5 levels have been shown to be elevated in a panel of lymphoid cancer cell lines as well as mantle cell lymphoma clinical samples. PRMT5 interacts with a number of substrates that are involved in a variety of cellular processes, including RNA processing, signal transduction, and transcriptional regulation. PRMT5 can directly modify histone H3 and H4, resulting in the repression of gene expression. PRMT5 overexpression can stimulate cell growth and induce transformation by directly repressing tumor suppressor genes. Pal et al., Mol. Cell. Biol. 2003, 7475; Pal et al. Mol. Cell. Biol. 2004, 9630; Wang et al. Mol. Cell. Biol. 2008, 6262; Chung et al. J Biol Chem 2013, 5534. In addition to its well-documented oncogenic functions in transcription and translation, the transcription factor MYC also safeguards proper pre-messenger-RNA splicing as an essential step in lymphomagenesis. Koh et al. Nature 2015, 523 7558; Hsu et al. Nature 2015 525, 384.

The discovery of cancer dependencies has the potential to inform therapeutic strategies and to identify putative drug targets. Integrating data from comprehensive genomic profiling of cancer cell lines and from functional characterization of cancer cell dependencies, it has been recently discovered that loss of the enzyme methylthioadenosine phosphorylase (MTAP) confers a selective dependence on protein arginine methyltransferase 5 (PRMT5) and its binding partner WDR77. MTAP is frequently lost due to its proximity to the commonly deleted tumor suppressor gene, CDKN2A. Cells harboring MTAP deletions possess increased intracellular concentrations of methylthioadenosine (MTA, the metabolite cleaved by MTAP). Furthermore, MTA specifically inhibits PRMT5 enzymatic activity. Administration of either MTA or a small-molecule PRMT5 inhibitor shows a preferential impairment of cell viability for MTAP-null cancer cell lines compared to isogenic MTAP-expressing counterparts. Together, these findings reveal PRMT5 as a potential vulnerability across multiple cancer lineages augmented by a common "passenger" genomic alteration.

Role of PRMT5 in Hemoglobinopathies

The developmental switch in human globin gene subtype from fetal to adult that begins at birth heralds the onset of the hemoglobinopathies, b-thalassemia and sickle cell disease (SCD). The observation that increased adult globin gene expression (in the setting of hereditary persistence of fetal hemoglobin [HPFH] mutations) significantly ameliorates the clinical severity of thalassemia and SCD has prompted the search for therapeutic strategies to reverse gamma-globin gene silencing. Central to silencing of the gamma-genes is DNA methylation, which marks critical CpG dinucleotides flanking the gene transcriptional start site in adult bone marrow erythroid cells. It has been shown that these marks are established as a consequence of recruitment of the DNA methyltransferase, DNMT3A to the gamma-promoter by the protein arginine methyltransferase PRMT5. Zhao et al. Nat Struct Mol Biol. 2009 16, 304. PRMT5-mediated methylation of histone H4R3 recruits DNMT3A, coupling histone and DNA methylation in gene silencing.

PRMT5 induces the repressive histone mark, H4R3me2s, which serves as a template for direct binding of DNMT3A, and subsequent DNA methylation. Loss of PRMT5 binding or its enzymatic activity leads to demethylation of the CpG dinucleotides and gene activation. In addition to the H4R3me2s mark and DNA methylation, PRMT5 binding to the gamma-promoter, and its enzymatic activity are essential for assembly of a multiprotein complex on the gamma-promoter, which induces a range of coordinated repressive epigenetic marks. Disruption of this complex leads to reactivation of gamma gene expression. These studies provide the basis for developing PRMT5 inhibitors as targeted therapies for thalassemia and SCD.

SUMMARY

The disclosure is directed to compounds of Formula I and Formula II:

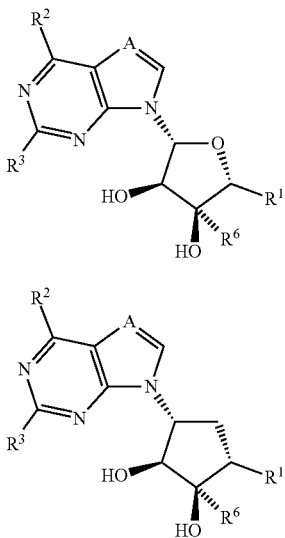

or a pharmaceutically acceptable salt or solvate thereof; wherein

A is N, C—H or C—R$^4$ wherein R$^4$ is halo or C$_1$-C$_6$haloalkyl;

R$^1$ is —C$_1$-C$_6$alk-fused aryl, or —C$_1$-C$_6$alk-fused heteroaryl

R$^2$ is halo, —C$_1$-C$_6$alkyl, —C$_2$-C$_4$alkenyl, —C$_1$-C$_6$alk-OH, —C$_1$-C$_6$alk-halo, —C$_1$-C$_6$alk-O—C$_1$-C$_6$alkyl, —C$_1$-C$_6$alk-O—C$_1$-C$_6$alk-aryl, —O—C$_1$-C$_6$alkyl, —NR$^5$R$^{5'}$, —NHC(O)NR$^5$R$^{5'}$, —NHC(S)NR$^5$R$^{5'}$, —NH—O—R$^5$, or —NH—NR$^5$R$^{5'}$;

R$^3$ is H, halo, NH$_2$, or —C$_1$-C$_6$alkyl;

R$^5$ and R$^{5'}$ are each independently H, C$_1$-C$_6$alkyl, or —C$_1$-C$_6$alk-OC$_1$-C$_6$alkyl;

or R$^5$ and R$^{5'}$, together with the atom to which they are attached, form a C$_2$-C$_6$heterocycloalkyl ring; and R$^6$ is H or —C$_1$-C$_6$alkyl.

Stereoisomers of the compounds of Formula I and Formula II, and the pharmaceutical salts and solvates thereof, are also described. Methods of using compounds of Formula I and Formula II are described, as well as pharmaceutical compositions including the compounds of Formula I and Formula II.

BRIEF DESCRIPTION OF THE DRAWINGS

FIG. 1 shows an ORTEP representation of the compound of Example 11.

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

The term "alkyl," when used alone or as part of a substituent group, refers to a straight- or branched-chain hydrocarbon group having from 1 to 12 carbon atoms ("C$_1$-C$_{12}$"), preferably 1 to 6 carbons atoms ("C$_1$-C$_6$"), in the group. Examples of alkyl groups include methyl (Me, C$_1$alkyl), ethyl(Et, C$_2$alkyl), n-propyl (C$_3$alkyl), isopropyl (C$_3$alkyl), butyl (C$_4$alkyl), isobutyl (C$_4$alkyl), sec-butyl (C$_4$alkyl), tert-butyl (C$_4$alkyl), pentyl (C$_5$alkyl), isopentyl (C$_5$alkyl), tert-pentyl (C$_5$alkyl), hexyl (C$_6$alkyl), isohexyl (C$_6$alkyl), and the like.

The term "alkenyl" when used alone or as part of a substituent group refers to a straight- or branched-chain group having from 2 to 12 carbon atoms ("C$_2$-C$_{12}$alkenyl"), preferably 2 to 4 carbons atoms ("C$_2$-C$_4$alkenyl"), in the group, wherein the group includes at least one carbon-carbon double bond. Examples of alkenyl groups include vinyl (—CH=CH$_2$; C$_2$alkenyl) allyl (—CH$_2$—CH=CH$_2$; C$_3$alkenyl), propenyl (—CH=CHCH$_3$; C$_3$alkenyl); isopropenyl (—C(CH$_3$)=CH$_2$; C$_3$alkenyl), butenyl (—CH=CHCH$_2$CH$_3$; C$_4$alkenyl), sec-butenyl (—C(CH$_3$)=CHCH$_3$; C$_4$alkenyl), iso-butenyl (—CH=C(CH$_3$)$_2$; C$_4$alkenyl), 2-butenyl (—CH$_2$CH=CHCH$_3$; C$_4$alkyl), pentenyl (—CH=CHCH$_2$CH$_2$CH$_3$; C$_5$alkenyl), and the like.

The term "halo" when used alone or as part of a substituent group refers to chloro, fluoro, bromo, or iodo.

The term "haloalkyl" when used alone or as part of a substituent group refers to refers to an alkyl group wherein one or more of the hydrogen atoms has been replaced with one or more halogen atoms. Halogen atoms include chlorine, fluorine, bromine, and iodine. Examples of haloalkyl groups of the disclosure include, for example, trifluoromethyl (—CF$_3$), chloromethyl (—CH$_2$Cl), and the like.

The term "cycloalkyl" when used alone or as part of a substituent group refers to cyclic-containing, non-aromatic hydrocarbon groups having from 3 to 10 carbon atoms ("C$_3$-C$_{10}$"), preferably from 3 to 6 carbon atoms ("C$_3$-C$_6$"). Examples of cycloalkyl groups include, for example, cyclopropyl (C$_3$), cyclobutyl (C$_4$), cyclopropylmethyl (C$_4$), cyclopentyl (C$_5$), cyclohexyl (C$_6$), 1-methylcyclopropyl (C$_4$), 2-methylcyclopentyl (C$_4$), adamantanyl (C$_{10}$), and the like.

The term "heterocycloalkyl" when used alone or as part of a substituent group refers to any three to ten membered monocyclic or bicyclic, saturated ring structure containing at least one heteroatom selected from the group consisting of O, N and S. Where N is a heteroatom in the heterocycloalkyl group, the N may be substituted with H, —C$_1$-C$_3$alkyl, C$_1$-C$_3$haloalkyl or C$_3$-C$_6$cycloalkyl. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

The term "aryl" when used alone or as part of a substituent group refers to a mono- or bicyclic-aromatic hydrocarbon ring structure having 6 or 10 carbon atoms in the ring, wherein one or more of the carbon atoms in the ring is optionally substituted with a halogen atom, a —C$_1$-C$_3$ alkyl group, an amino-substituted —C$_1$-C$_3$ alkyl group, a C$_1$-C$_3$haloalkyl group, an amino group (i.e., —NH$_2$), or a substituted amino group. Preferred aryl groups include phenyl and naphthyl.

The term "fused aryl" when used alone or as part of a substituent group refers to a fused-ring bicyclic-group having 6 to 10 carbon atoms, wherein one of the rings has a fully conjugated pi electron system, and the other ring does not have a fully conjugated pi electron system; and wherein one or more of the carbon atoms is optionally substituted with a halogen atom, a —$C_1$-$C_3$ alkyl group, an amino-substituted —$C_1$-$C_3$ alkyl group, a $C_1$-$C_3$ haloalkyl group, an amino group (i.e., —$NH_2$), or a substituted amino group. In addition, one or more of the carbon atoms of the ring that does not have a fully conjugated pi electron system may also optionally substituted with a hydroxy group (—OH), a keto group (C=O), or a cyano group (—CN). Halogen atoms include chlorine, fluorine, bromine, and iodine. Amino-substituted —$C_1$-$C_3$ alkyl groups include —$CH_2$—$NH_2$, —$CH_2CH_2$—$NH_2$, and the like. $C_1$-$C_3$ haloalkyl groups include, for example, —$CF_3$, —$CH_2CF_3$, and the like. Substituted amino groups include, for example, —NH—C(O)—$NH_2$. Examples of fused aryl groups include:

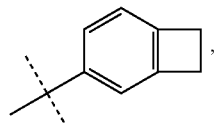

(bicycle[4.2.0]octa-1(6),2,4-trien-3-yl)

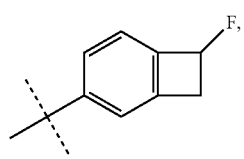

(7-fluorobicyclo[4.2.0]octa-1(6),2,4-trien-3-yl)

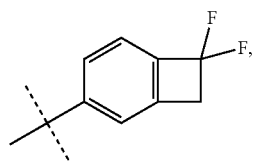

(7,7-difluorobicyclo[4.2.0]octa-1(6),2,4-trien-3-yl)

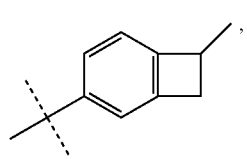

(7-methylbicyclo[4.2.0]octa-1(6),2,4-triene-3-yl)

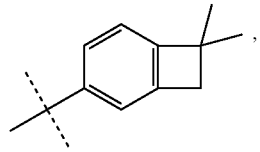

(7,7-methylbicyclo[4.2.0]octa-1(6),2,4-triene-3-yl)

-continued

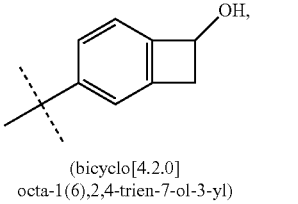

(bicyclo[4.2.0]octa-1(6),2,4-trien-7-ol-3-yl)

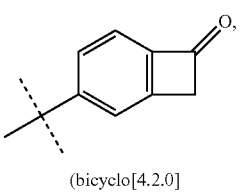

(bicyclo[4.2.0]octa-1(6),2,4-trien-7-one-3-yl)

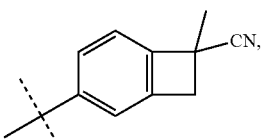

(7-methylbicyclo[4.2.0]octa-1(6),2,4-triene-7-carbonirtile-3-yl)

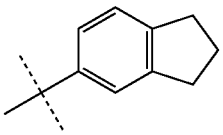

(2,3-dihydro-1H-inden-5-yl)

and the like.

The term "fused heteroaryl" when used alone or as part of a substituent group refers to fused-ring bicyclic group including carbon atoms as well as up to four heteroatoms selected from nitrogen, oxygen, and sulfur, wherein one of the rings has a fully conjugated pi electron system, and the other ring does not have a fully conjugated pi electron system. Fused heteroaryl rings can include a total of 8, 9, or 10 ring atoms. The heteroatoms may be present in either the ring having a fully conjugated pi electron system, or in the ring that does not have a fully conjugated pi electron system, or in both of the rings. The fused heteroaryl moiety can be unsubstituted, or one or more of the atoms in the ring can be substituted with a halogen atom; an amino group; a substituted amino group, including an amino group substituted with a —$C_3$-$C_6$ cycloalkyl group or a —$C_1$-$C_6$ alkyl group; or a —$C_1$-$C_3$ alkyl group. Halogen atoms include chlorine, fluorine, bromine, and iodine. Examples of fused heteroaryl groups include

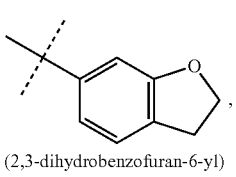

(2,3-dihydrobenzofuran-6-yl)

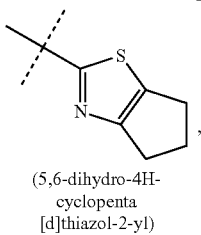

(5,6-dihydro-4H-cyclopenta[d]thiazol-2-yl)

and the like.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "$C_1$-$C_6$alk" when used alone or as part of a substituent group refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond. In some aspects, the $C_1$-$C_6$alk can be substituted with one or more —OH, —$NH_2$, or halo (e.g., —F, —Cl, —Br, with —F being preferred) substituents. $C_1$alk groups, for example, include:

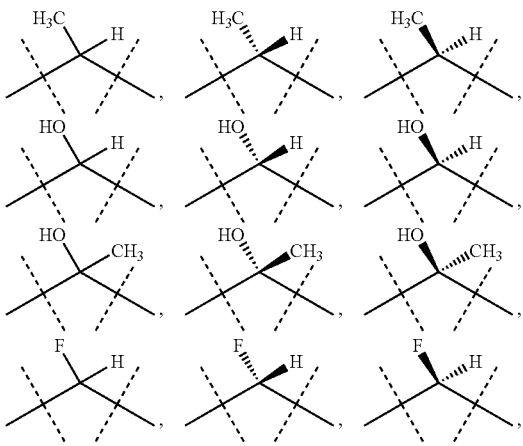

and the like.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of Formula I or Formula II as described herein, as well as their subgenera, which expression includes the stereoisomers (e.g., enantiomers, diastereomers) and constitutional isomers (e.g., tautomers) of compounds of Formula I or Formula II as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

The disclosure is directed to compounds of Formula I.

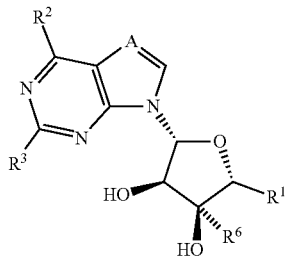

I

According to the disclosure, A in Formula I is N, C—H, or C—$R^4$. In some aspects, A is N, and the compounds of Formula I have the structure IA:

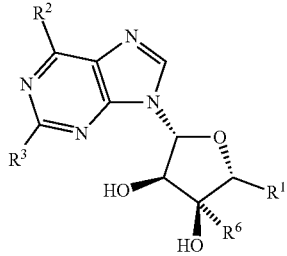

IA

In other aspects, A is C—H, and the compounds of Formula I have the structure IB:

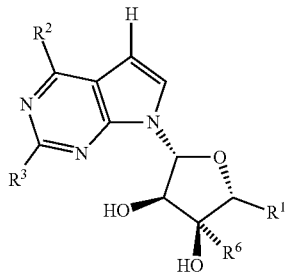

IB

In other aspects, A is C—$R^4$, and the compounds of Formula I have the structure IC:

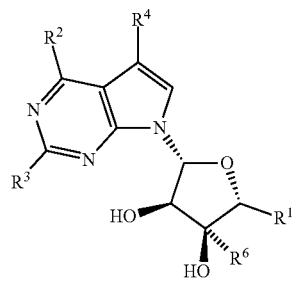

IC

In some aspects, $R^4$ in compounds of Formula IC is halo. In other aspects, $R^4$ in compounds of Formula IC is halo or $C_1$-$C_6$haloalkyl.

In some embodiments $R^4$ is halo, for example, F, Cl, Br, or I. In some embodiments, $R^4$ is F. In other embodiments, $R^4$ is Br. In yet other embodiments, $R^4$ is I.

In some embodiments, $R^4$ is $C_1$-$C_6$haloalkyl, for example, $C_6$haloalkyl, $C_5$haloalkyl, $C_4$haloalkyl, $C_3$haloalkyl, $C_2$haloalkyl, $C_1$haloalkyl, —$CF_3$, and the like. In some embodiments, $R^4$ is —$CF_3$.

The disclosure is directed to compounds of Formula II:

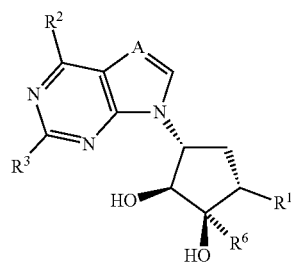

II

According to the disclosure, A in Formula II is N, C—H, or C—$R^4$. In some aspects, A is N, and the compounds of Formula II have the structure IIA:

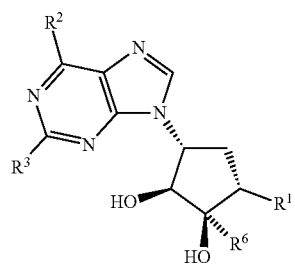

IIA

In other aspects, A is C—H, and the compounds of Formula II have the structure IIB

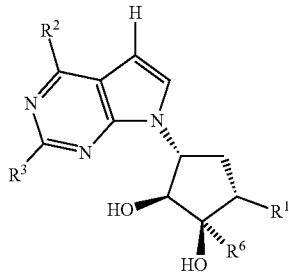

In other aspects, A is C—R⁴, and the compounds of Formula II have the structure IIC:

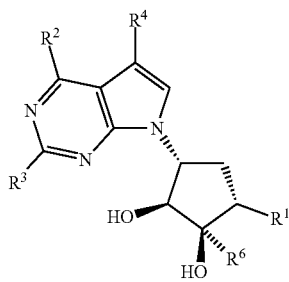

In some aspects, $R^4$ in compounds of Formula IIC is halo. In other aspects, $R^4$ in compounds of Formula IIC is halo or $C_1$-$C_6$haloalkyl.

In some embodiments $R^4$ is halo, for example, F, Cl, Br, or I. In some embodiments, $R^4$ is F. In other embodiments, $R^4$ is Br. In yet other embodiments, $R^4$ is I.

In some embodiments, $R^4$ is $C_1$-$C_6$haloalkyl, for example, $C_6$haloalkyl, $C_5$haloalkyl, $C_4$haloalkyl, $C_3$haloalkyl, $C_2$haloalkyl, $C_1$haloalkyl, —$CF_3$, and the like. In some embodiments, $R^4$ is —$CF_3$.

In some aspects, $R^1$ in the compounds of Formula I and Formula II is —$C_1$-$C_6$alk-fused aryl, for example, —$C_1$alk-fused aryl, —$C_2$alk-fused aryl, —$C_3$alk-fused aryl, —$C_4$alk-fused aryl, —$C_5$alk-fused aryl, —Calk-fused aryl, —$CH_2$fused aryl, —CH(OH)-fused aryl, —CH(F)-fused aryl, —CH($NH_2$)-fused aryl, —CH(Me)-fused aryl, —C(Me)(OH)-fused aryl, and the like. In some embodiments wherein $R^1$ is —$C_1$-$C_6$alk-fused aryl, the -fused aryl is bicyclo[4.2.0]octa-1(6),2,4-trien-3-yl, 7-fluorobicyclo[4.2.0]octa-1(6),2,4-trien-3-yl, 7,7-difluorobicyclo[4.2.0]octa-1(6),2,4-trien-3-yl. Thus in some embodiments, $R^1$ is —$CH_2$-(bicyclo[4.2.0]octa-1(6),2,4-trien-3-yl), —$CH_2$-(7-fluorobicyclo[4.2.0]octa-1(6),2,4-trien-3-yl), —$CH_2$-(7,7-difluorobicyclo[4.2.0]octa-1(6),2,4-trien-3-yl), —CH(OH)-(bicyclo[4.2.0]octa-1(6),2,4-trien-3-yl), —CH(OH)-(7-fluorobicyclo[4.2.0]octa-1(6),2,4-trien-3-yl), —CH(OH)-(7,7-difluorobicyclo[4.2.0]octa-1(6),2,4-trien-3-yl), —CH(F)-(bicyclo[4.2.0]octa-1(6),2,4-trien-3-yl), —CH(F)-(7-fluorobicyclo[4.2.0]octa-1(6),2,4-trien-3-yl), —CH(F)-(7,7-difluorobicyclo[4.2.0]octa-1(6),2,4-trien-3-yl), —CH($NH_2$)-(bicyclo[4.2.0]octa-1(6),2,4-trien-3-yl), —CH($NH_2$)-(7-fluorobicyclo[4.2.0]octa-1(6),2,4-trien-3-yl), —CH($NH_2$)-(7,7-difluorobicyclo[4.2.0]octa-1(6),2,4-trien-3-yl), —CH(Me)-(bicyclo[4.2.0]octa-1(6),2,4-trien-3-yl), —CH(Me)-(7-fluorobicyclo[4.2.0]octa-1(6),2,4-trien-3-yl), —CH(Me)-(7,7-difluorobicyclo[4.2.0]octa-1(6),2,4-trien-3-yl), —C(Me)(OH)-(bicyclo[4.2.0]octa-1(6),2,4-trien-3-yl), —C(Me)(OH)-(7-fluorobicyclo[4.2.0]octa-1(6),2,4-trien-3-yl), or —C(Me)(OH)-(7,7-difluorobicyclo[4.2.0]octa-1(6),2,4-trien-3-yl).

In other embodiments wherein $R^1$ is —$C_1$-$C_6$alk-fused aryl, the -fused aryl is 7-methylbicyclo[4.2.0]octa-1(6),2,4-triene-3-yl, 7,7-dimethylbicyclo[4.2.0]octa-1(6),2,4-triene-3-yl, bicyclo[4.2.0]octa-1(6),2,4-trien-7-ol-3-yl, bicyclo[4.2.0]octa-1(6),2,4-trien-7-one-3-yl, 7-methylbicyclo[4.2.0]octa-1(6),2,4-triene-7-carbonitrile-3-yl, or 2,3-dihydro-1H-inden-5-yl. Thus, in some embodiments, $R^1$ is —$CH_2$-(7-methylbicyclo[4.2.0]octa-1(6),2,4-triene-3-yl), —$CH_2$-(7,7-dimethylbicyclo[4.2.0]octa-1(6),2,4-triene-3-yl), —$CH_2$-(bicyclo[4.2.0]octa-1(6),2,4-trien-7-ol-3-yl), —$CH_2$-(bicyclo[4.2.0]octa-1(6),2,4-trien-7-one-3-yl), —$CH_2$-(7-methylbicyclo[4.2.0]octa-1(6),2,4-triene-7-carbonitrile-3-yl), —$CH_2$-(2,3-dihydro-1H-inden-5-yl), —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), —CH(OH)-(2,3-dihydro-1H-inden-5-yl), —CH(F)-(7-methylbicyclo[4.2.0]octa-1(6),2,4-triene-3-yl), —CH(F)-(7,7-dimethylbicyclo[4.2.0]octa-1(6),2,4-triene-3-yl), —CH(F)-(bicyclo[4.2.0]octa-1(6),2,4-trien-7-ol-3-yl), —CH(F)-(bicyclo[4.2.0]octa-1(6),2,4-trien-7-one-3-yl), —CH(F)-(7-methylbicyclo[4.2.0]octa-1(6),2,4-triene-7-carbonitrile-3-yl), —CH(F)-(2,3-dihydro-1H-inden-5-yl), —CH($NH_2$)-(7-methylbicyclo[4.2.0]octa-1(6),2,4-triene-3-yl), —CH($NH_2$)-(7,7-dimethylbicyclo[4.2.0]octa-1(6),2,4-triene-3-yl), —CH($NH_2$)-(bicyclo[4.2.0]octa-1(6),2,4-trien-7-ol-3-yl), —CH($NH_2$)-(bicyclo[4.2.0]octa-1(6),2,4-trien-7-one-3-yl), —CH($NH_2$)-(7-methylbicyclo[4.2.0]octa-1(6),2,4-triene-7-carbonitrile-3-yl), —CH($NH_2$)-(2,3-dihydro-1H-inden-5-yl), —CH(Me)-(7-methylbicyclo[4.2.0]octa-1(6),2,4-triene-3-yl), —CH(Me)-(7,7-dimethylbicyclo[4.2.0]octa-1(6),2,4-triene-3-yl), —CH(Me)-(bicyclo[4.2.0]octa-1(6),2,4-trien-7-ol-3-yl), —CH(Me)-(bicyclo[4.2.0]octa-1(6),2,4-trien-7-one-3-yl), —CH(Me)-(7-methylbicyclo[4.2.0]octa-1(6),2,4-triene-7-carbonitrile-3-yl), —CH(Me)-(2,3-dihydro-1H-inden-5-yl), —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl).

In some aspects, $R^1$ in the compounds of Formula I and Formula II is —$C_1$-$C_6$alk-fused heteroaryl, for example, —$C_1$alk-fused heteroaryl, —$C_2$alk-fused heteroaryl, —$C_3$alk-fused heteroaryl, —$C_4$alk-fused heteroaryl, —$C_5$alk-fused heteroaryl, —$C_6$alk-fused heteroaryl, —$CH_2$-fused heteroaryl, —CH(OH)-fused heteroaryl, —CH(F)-fused heteroaryl, —CH($NH_2$)-fused heteroaryl, —CH(Me)-fused heteroaryl, —C(Me)(OH)-fused heteroaryl, and the like. In some embodiments wherein $R^1$ is —$C_1$-$C_6$alk-fused heteroaryl, the -fused heteroaryl is 2,3-dihydrobenzofuran-6-yl. Thus in some embodiments, $R^1$ is —$CH_2$-(2,3-dihydrobenzofuran-6-yl), —CH(OH)-(2,3-dihydrobenzofuran-6-yl), —CH(F)-(2,3-dihydrobenzofuran- 6-yl), —CH($NH_2$)-(2,3-dihydrobenzofuran-6-yl), —CH(Me)-(2,3-dihydrobenzofuran-6-yl), or —C(Me)(OH)-(2,3-dihydrobenzofuran-6-yl).

In some embodiments wherein $R^1$ is —$C_1$-$C_6$alk-fused heteroaryl, the -fused heteroaryl is 5,6-dihydro-4H-cyclopenta[d]thiazol-2-yl. Thus in some embodiments, $R^1$ is —$CH_2$-(5,6-dihydro-4H-cyclopenta[d]thiazol-2-yl), —CH(OH)-(5,6-dihydro-4H-cyclopenta[d]thiazol-2-yl), —CH(F)-(5,6-dihydro-4H-cyclopenta[d]thiazol-2-yl), —CH($NH_2$)-(5,6-dihydro-4H-cyclopenta[d]thiazol-2-yl), —CH(Me)-(5,6-dihydro-4H-cyclopenta[d]thiazol-2-yl), or —C(Me)(OH)-(5,6-dihydro-4H-cyclopenta[d]thiazol-2-yl).

In compounds of Formula I and Formula II in the present disclosure, $R^3$ is H, halo, —$C_1$-$C_6$alkyl, or $NH_2$. Thus in some embodiments, $R^3$ is H. In other embodiments, $R^3$ is halo, for example F, Cl, Br, or I. In other embodiments, $R^3$ is —$C_1$-$C_6$alkyl, for example, methyl, ethyl, propyl, isopropyl, butyl, isobutyl, s-butyl, t-butyl, pentyl, and the like. Thus, in some embodiments, $R^3$ is methyl (Me). In yet other embodiments, $R^3$ is $NH_2$. In the most preferred embodiments, $R^3$ is H.

In some aspects, in compounds of Formula I or Formula II in the present disclosure, $R^2$ is halo, —$C_1$-$C_6$alkyl, —$C_1$-$C_6$alk-O—$C_1$-$C_6$alkyl, —$NR^5R^{5'}$, —$NHCONR^5R^{5'}$, NHC(S)$NR^5R^{5'}$, —NH—O—$R^5$, or —NH—$NR^5R^{5'}$. In other aspects, $R^2$ in the compounds of Formula I or Formula II is halo, —$C_1$-$C_6$alkyl, —$C_2$-$C_4$alkenyl, —$C_1$-$C_6$alk-OH, —$C_1$-$C_6$alk-halo, —$C_1$-$C_6$alk-O—$C_1$-$C_6$alkyl, —$C_1$-$C_6$alk-O—$C_1$-$C_6$alk-aryl, —O—$C_1$-$C_6$alkyl, —$NR^5R^{5'}$, —NHC(O)$NR^5R^{5'}$, —NHC(S)$NR^5R^{5'}$, —NH—O—$R^5$, or —NH—$NR^5R^{5'}$.

In some aspects, $R^2$ is halo, for example chloro, fluoro, bromo, or iodo. In some embodiments, $R^2$ is chloro.

In some aspects, $R^2$ is —$C_1$-$C_6$alkyl, for example, methyl, ethyl, propyl, isopropyl, butyl, isobutyl, s-butyl, t-butyl, pentyl, and the like. In some embodiments, $R^2$ is methyl. In other embodiments, $R^2$ is n-butyl (—$CH_2CH_2CH_2CH_3$). In yet other embodiments, $R^2$ is isopropyl (—CH($CH_3$)$_2$).

In some aspects, $R^2$ is —$C_2$-$C_4$alkenyl, for example, —$C_4$alkenyl, —$C_3$alkenyl, —$C_2$alkenyl, vinyl, allyl, isopropenyl, and the like. In some embodiments, $R^2$ is vinyl (—CH=$CH_2$). In other embodiments, $R^2$ is isopropenyl (—C($CH_3$)=$CH_2$).

In some aspects, $R^2$ is —$C_1$-$C_6$alk-OH, for example, $C_6$alk-OH, $C_5$alk-OH, $C_4$alk-OH, $C_3$alk-OH, $C_2$alk-OH, $C_1$alk-OH, —$CH_2$—OH, —$CH_2CH_2$—OH, and the like. In some embodiments, $R^2$ is —$CH_2$—OH. In other embodiments, $R^2$ is —$CH_2CH_2$—OH.

In some aspects, $R^2$ is —$C_1$-$C_6$alk-halo, for example, $C_6$alk-halo, $C_5$alk-halo, $C_4$alk-halo, $C_3$alk-halo, $C_2$alk-halo, $C_1$alk-halo, —$CH_2$-halo, —$CH_2CH_2$-halo, and the like. In some embodiments, $R^2$ is —$CH_2$—Cl. In other embodiments, $R^2$ is —$CH_2$—F.

In some aspects, $R^2$ is —$C_1$-$C_6$alk-O—$C_1$-$C_6$alkyl, for example, —$C_1$-$C_6$alk-O—$C_1$-$C_6$alkyl, —$C_1$-$C_6$alk-O—$C_1$-$C_6$alkyl, —$C_1$-$C_4$alk-O—$C_1$-$C_6$alkyl, —$C_1$-$C_3$alk-O—$C_1$-$C_6$alkyl, —$C_1$-$C_2$alk-O—$C_1$-$C_6$alkyl, —$C_1$alk-O—$C_1$-$C_6$alkyl, —$C_1$-$C_6$alk-O—$C_1$-$C_5$alkyl, —$C_1$-$C_6$alk-O—$C_1$-$C_4$alkyl, —$C_1$-$C_6$alk-O—$C_1$-$C_3$alkyl, —$C_1$-$C_6$alk-O—$C_1$-$C_2$alkyl, or —$C_1$-$C_6$alk-O—$C_1$alkyl. In some embodiments, $R^2$ is —$CH_2CH_2$—O—$CH_3$. In other embodiments, $R^2$ is —$CH_2$—O—$CH_2CH_3$.

In some aspects, $R^2$ is —$C_1$-$C_6$alk-O—$C_1$-$C_6$alk-aryl, for example, —$C_1$alk-O—$C_1$alk-aryl, —$C_2$alk-O—$C_1$alk-aryl, —$C_3$alk-O—$C_1$alk-aryl, —$C_4$alk-O—$C_1$alk-aryl, —$C_5$alk-O—$C_1$alk-aryl, —$C_6$alk-O—$C_1$alk-aryl, —$C_1$alk-O—$C_2$alk-aryl, —$C_2$alk-O—$C_2$alk-aryl, —$C_3$alk-O—$C_2$alk-aryl, —$C_4$alk-O—$C_2$alk-aryl, —$C_5$alk-O—$C_2$alk-aryl, —$C_6$alk-O—$C_2$alk-aryl, —$C_1$alk-O—$C_3$alk-aryl, —$C_2$alk-O—$C_3$alk-aryl, —$C_3$alk-O—$C_3$alk-aryl, —$C_4$alk-O—$C_3$alk-aryl, —$C_5$alk-O—$C_3$alk-aryl, —$C_6$alk-O—$C_3$alk-aryl, —$C_1$alk-O—$C_4$alk-aryl, —$C_2$alk-O—$C_4$alk-aryl, —$C_3$alk-O—$C_4$alk-aryl, —$C_4$alk-O—$C_4$alk-aryl, —$C_5$alk-O—$C_4$alk-aryl, —$C_6$alk-O—$C_4$alk-aryl, —$C_1$alk-O—$C_5$alk-aryl, —$C_2$alk-O—$C_5$alk-aryl, —$C_3$alk-O—$C_5$alk-aryl, —$C_4$alk-O—$C_5$alk-aryl, —$C_5$alk-O—$C_5$alk-aryl, —$C_6$alk-O—$C_5$alk-aryl, —$C_1$alk-O—$C_6$alk-aryl, —$C_2$alk-O—$C_6$alk-aryl, —$C_3$alk-O—$C_6$alk-aryl, —$C_4$alk-O—$C_6$alk-aryl, —$C_5$alk-O—$C_6$alk-aryl, —$C_6$alk-O—$C_6$alk-aryl. In some embodiments, $R^2$ is —$C_2$alk-O—$C_1$alk-aryl. In some embodiments, $R^2$ is —$CH_2CH_2$—O—$CH_2$-phenyl.

In some aspects, $R^2$ is —O—$C_1$-$C_6$alkyl, for example, —O—$C_6$alkyl, —O—$C_5$alkyl, —O—$C_4$alkyl, —O—$C_3$alkyl, —O—$C_2$alkyl, —O—$C_1$alkyl, —O—$CH_3$, —O—$CH_2CH_3$, and the like. In some embodiments, $R^2$ is —O—$CH_3$.

In some aspects, $R^2$ is —$NR^5R^{5'}$. Thus, in some embodiments wherein $R^5$ and $R^{5'}$ are both H, $R^2$ is —$NH_2$. In some embodiments wherein $R^5$ and $R^{5'}$ are both methyl, $R^2$ is —N($CH_3$)$_2$. In embodiments wherein $R^5$ is H and $R^{5'}$ is methyl, $R^2$ is —NH($CH_3$).

In some aspects, $R^2$ is —$NHCONR^5R^{5'}$. Thus, in some embodiments wherein $R^5$ and $R^{5'}$ are both H, $R^2$ is —$NHCONH_2$. In embodiments wherein $R^5$ and $R^{5'}$ are both methyl, $R^2$ is —NHCON($CH_3$)$_2$. In embodiments wherein $R^5$ is H and $R^{5'}$ is methyl, $R^2$ is —NHCONH$CH_3$.

In some aspects, $R^2$ is NHC(S)$NR^5R^{5'}$. Thus, in some embodiments wherein $R^5$ and $R^{5'}$ are both H, $R^2$ is —NHC(S)$NH_2$. In embodiments wherein $R^5$ and $R^{5'}$ are both methyl, $R^2$ is —NHC(S)N($CH_3$)$_2$. In embodiments wherein $R^5$ is H and $R^{5'}$ is methyl, $R^2$ is —NHC(S)NH$CH_3$.

In some aspects, $R^2$ is —NH—O—$R^5$. In some embodiments wherein $R^5$ is $C_1$-$C_6$alkyl, for example, methyl, $R^2$ is —NH—$OCH_3$. In some embodiments wherein $R^5$ is $C_1$-$C_6$alkyl, for example, ethyl, $R^2$ is —NH—$OCH_2CH_3$. In some embodiments wherein $R^5$ is H, $R^2$ is —NH—OH.

In some aspects, $R^2$ is —NH—$NR^5R^{5'}$. In some embodiments wherein $R^5$ and $R^{5'}$ are both H, $R^2$ is —NH—$NH_2$. In embodiments wherein $R^5$ and $R^{5'}$ are both $C_1$-$C_6$alkyl, for example, methyl, $R^2$ is —NH—N($CH_3$)$_2$. In embodiments wherein $R^5$ is H and $R^{5'}$ is $C_1$-$C_6$alkyl, for example, methyl, $R^2$ is —NH—NH$CH_3$.

It will be apparent that when $R^2$ is —NH—O—$R^5$ or —NH—$NR^5R^{5'}$, the compounds of Formula I and Formula II may exist as tautomers having (E)- or (Z)-geometry at the exocyclic carbon-nitrogen double bond. The compounds of Formula I and Formula II described and claimed herein are meant to encompass all such tautomers and geometric isomers, and mixtures thereof. The depiction of a particular tautomer or geometric isomer is not intended to be limiting. For example, when $R^2$ is —NH—O—$R^5$, compounds of Formula I may be represented by any of the following equivalent structures:

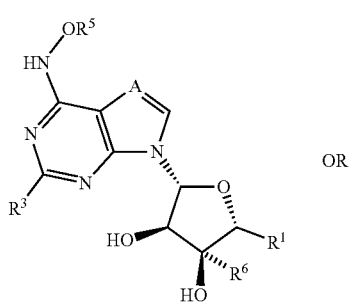
OR
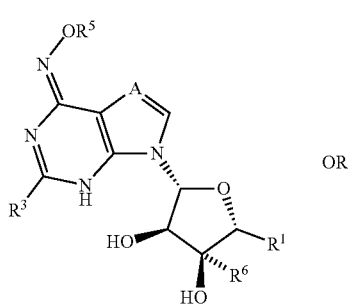
OR
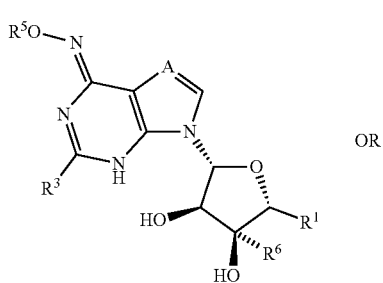
OR
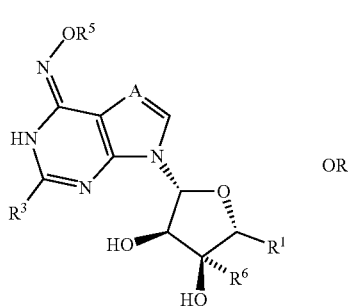
OR
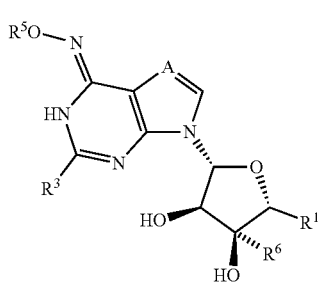
Similarly, when $R^2$ is —NH—NR$^5$R$^{5'}$, compounds of Formula I may be represented by any of the following equivalent structures:
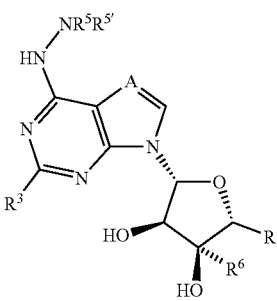
OR
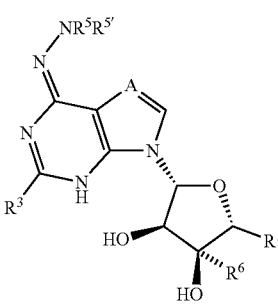
OR
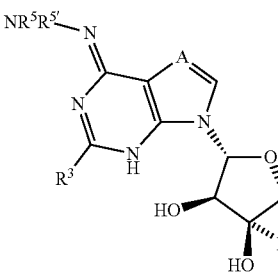
OR
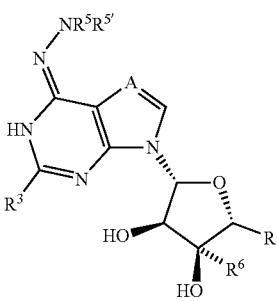
OR
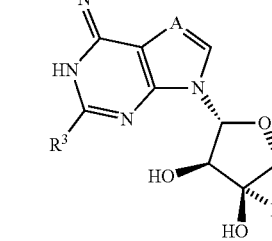

Similarly, when R² is —NH—O—R⁵, compounds of Formula II may be represented by any of the following equivalent structures:

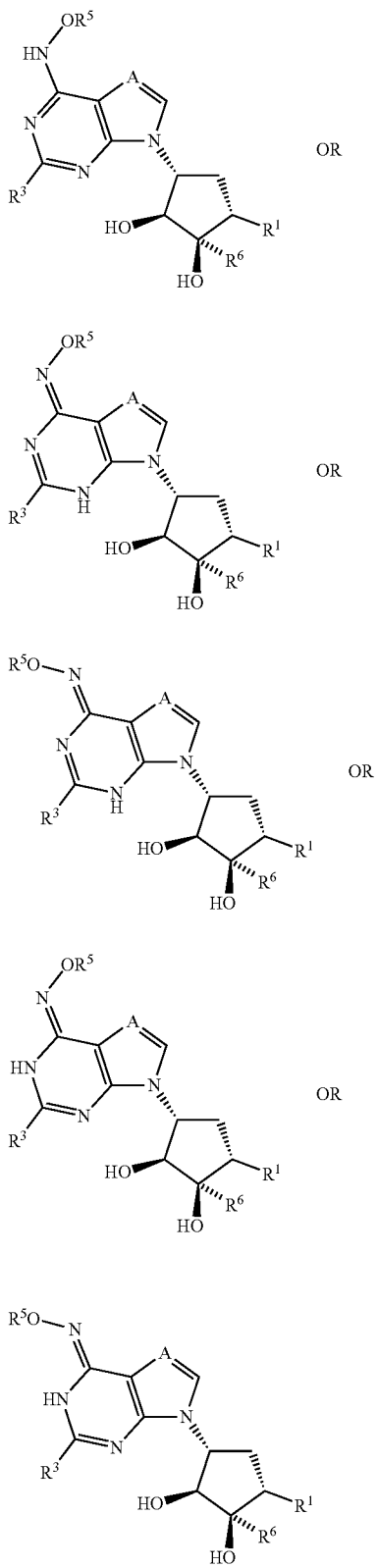

Similarly, when R² is —NH—NR⁵R⁵', compounds of Formula II may be represented by any of the following equivalent structures:

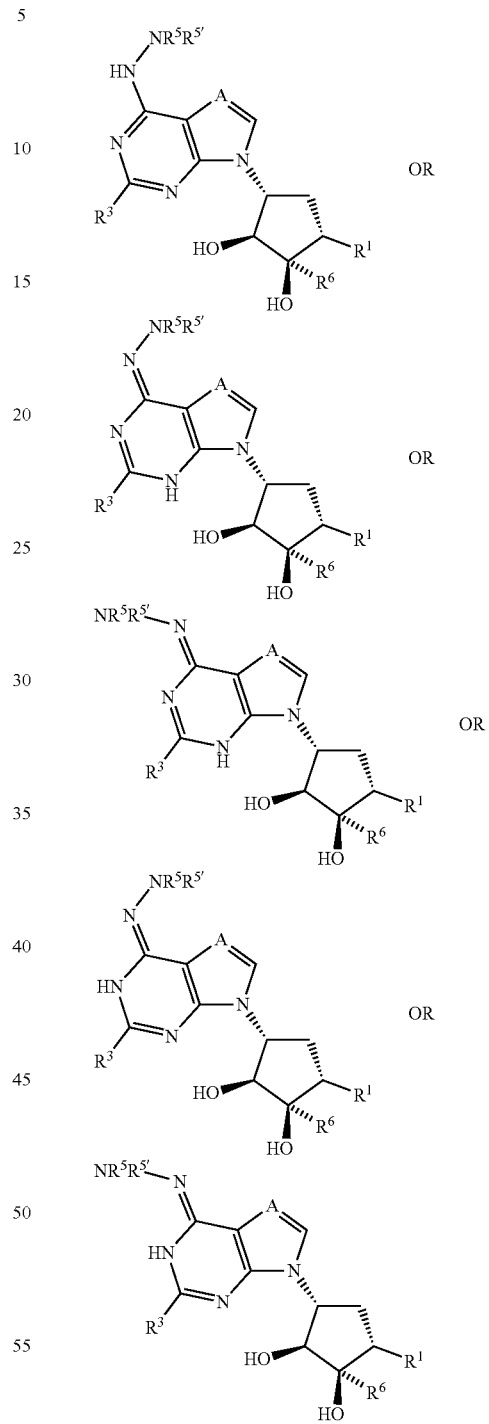

In compounds of the present disclosure, R⁵ and R⁵' are each independently H, $C_1$-$C_6$alkyl (e.g., methyl, ethyl, propyl, isopropyl, butyl, isobutyl, s-butyl, t-butyl, pentyl, and the like), or —$C_1$-$C_6$alk-O$C_1$-$C_6$alkyl (e.g., $C_1$-$C_6$alk-O$C_1$-$C_6$alkyl, $C_1$-$C_5$alk-O$C_1$-$C_6$alkyl, $C_1$-$C_4$alk-O$C_1$-$C_6$alkyl, $C_1$-$C_3$alk-O$C_1$-$C_6$alkyl, $C_1$-$C_2$alk-O$C_1$-$C_6$alkyl, $C_1$alk-O$C_1$-$C_6$alkyl, $C_1$-$C_6$alk-O$C_1$-$C_5$alkyl, $C_1$-$C_6$alk-O$C_1$-$C_4$alkyl, $C_1$-$C_6$alk-O$C_1$-$C_3$alkyl, $C_1$-$C_6$alk-O$C_1$-$C_2$alkyl, or $C_1$-$C_6$alk-O$C_1$alkyl).

In some embodiments, $R^5$ is H or $C_1$-$C_6$alkyl. In some embodiments, $R^{5'}$ is H or $C_1$-$C_6$alkyl.

In some embodiments, $R^5$ and $R^{5'}$ are each H.

In other embodiments, $R^5$ and $R^{5'}$ are each independently $C_1$-$C_6$alkyl. Thus, in some embodiments $R^5$ is methyl and $R^{5'}$ is methyl.

In some aspects, $R^5$ is $C_1$-$C_6$alkyl and $R^{5'}$ is H. Thus, in some embodiments, $R^5$ is methyl and $R^{5'}$ is H.

In other aspects, $R^5$ and $R^{5'}$ are each independently —$C_1$-$C_6$alk-O$C_1$-$C_6$alkyl.

In other aspects, $R^5$ is —$C_1$-$C_6$alk-O$C_1$-$C_6$alkyl and $R^{5'}$ is H.

In some embodiments of the disclosure, $R^5$ and $R^{5'}$, together with the atom to which they are attached, form a $C_2$-$C_6$heterocycloalkyl, for example, azepanyl, aziridinyl, azetidinyl, pyrrolidinyl, imidazolidinyl, pyrazolidinyl, piperazinyl, piperidinyl, morpholinyl, thiomorpholinyl, oxazepanyl, piperazinyl, and the like.

In compounds of the present disclosure, $R^6$ is H or $C_1$-$C_6$alkyl. In some embodiments, $R^6$ is H. In other embodiments, $R^6$ is $C_1$-$C_6$alkyl, for example, methyl.

In some aspects, the present disclosure is directed to compounds of Formula IA-1

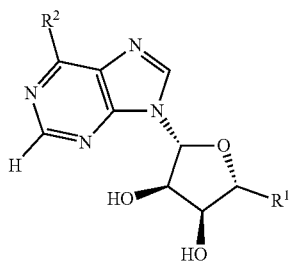

IA-1 wherein $R^1$ is —CH(OH)-fused aryl, —C(Me)(OH)-fused aryl, —CH(OH)-fused heteroaryl, or C(Me)(OH)-fused heteroaryl; and $R^2$ is —$NH_2$ or —$CH_3$.

In some embodiments of the compound of Formula IA-1, $R^1$ is —CH(OH)-fused aryl, or —C(Me)(OH)-fused aryl; and $R^2$ is —$NH_2$ or —$CH_3$.

In some embodiments of the compound of Formula IA-1, $R^1$ is —CH(OH)-fused heteroaryl, or C(Me)(OH)-fused heteroaryl; and $R^2$ is —$NH_2$ or —$CH_3$.

In some embodiments of the compound of Formula IA-1, $R^1$ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and $R^2$ is —$NH_2$ or —$CH_3$.

In other embodiments of the compound of Formula IA-1, $R^1$ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2, 4-trien-3-yl; and $R^2$ is —$NH_2$ or —$CH_3$.

In other embodiments of the compound of Formula IA-1, $R^1$ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and $R^2$ is —$NH_2$ or —$CH_3$.

In other embodiments of the compound of Formula IA-1, $R^1$ is —C(Me)(OH)-(7-methylbicyclo[4.2.0]octa-1(6),2,4-triene-3-yl), —C(Me)(OH)-(7,7-dimethylbicyclo[4.2.0] octa-1(6),2,4-triene-3-yl), —C(Me)(OH)-(bicyclo[4.2.0] octa-1(6),2,4-trien-7-ol-3-yl), —C(Me)(OH)-(bicyclo [4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and $R^2$ is —$NH_2$ or —$CH_3$.

In yet other embodiments of the compound of Formula IA-1, $R^1$ is —CH(OH)-2,3-dihydrobenzofuran-6-yl, or —C(Me)(OH)-2,3-dihydrobenzofuran-6-yl; and $R^2$ is —$NH_2$ or —$CH_3$.

In yet other embodiments of the compound of Formula IA-1, $R^1$ is —CH(OH)-(5,6-dihydro-4H-cyclopenta[d]thiazol-2-yl) or —C(Me)(OH)-(5,6-dihydro-4H-cyclopenta[d] thiazol-2-yl); and $R^2$ is —$NH_2$ or —$CH_3$.

In some aspects, the present disclosure is directed to compounds of Formula IA-2

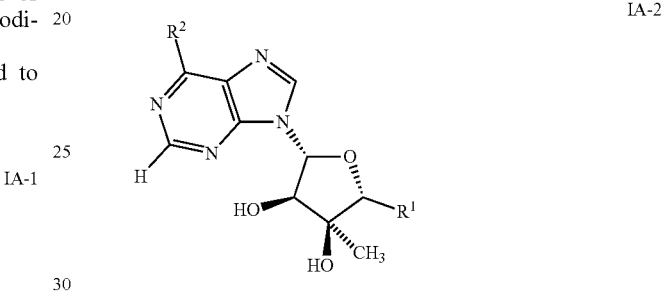

IA-2 wherein $R^1$ is —CH(OH)-fused aryl, —C(Me)(OH)-fused aryl, —CH(OH)-fused heteroaryl, or C(Me)(OH)-fused heteroaryl; and $R^2$ is —$NH_2$ or —$CH_3$.

In some embodiments of the compound of Formula IA-2, $R^1$ is —CH(OH)-fused aryl, or —C(Me)(OH)-fused aryl, and $R^2$ is —$NH_2$ or —$CH_3$.

In some embodiments of the compound of Formula IA-2, $R^1$ is —CH(OH)-fused heteroaryl, or C(Me)(OH)-fused heteroaryl, and $R^2$ is —$NH_2$ or —$CH_3$.

In some embodiments of the compound of Formula IA-2, $R^1$ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and $R^2$ is —$NH_2$ or —$CH_3$.

In other embodiments of the compound of Formula IA-2, $R^1$ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2, 4-trien-3-yl; and $R^2$ is —$NH_2$ or —$CH_3$.

In other embodiments of the compound of Formula IA-2, $R^1$ is —CH(OH)-(7-methylbicyclo[4.2.0]octa-1(6),2,4-triene-3-yl), —CH(OH)-(7,7-dimethylbicyclo[4.2.0]octa-1 (6),2,4-triene-3-yl), —CH(OH)-(bicyclo[4.2.0]octa-1(6),2, 4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and $R^2$ is —$NH_2$ or —$CH_3$.

In other embodiments of the compound of Formula IA-2, $R^1$ is —C(Me)(OH)-(7-methylbicyclo[4.2.0]octa-1(6),2,4-triene-3-yl), —C(Me)(OH)-(7,7-dimethylbicyclo[4.2.0] octa-1(6),2,4-triene-3-yl), —C(Me)(OH)-(bicyclo[4.2.0] octa-1(6),2,4-trien-7-ol-3-yl), —C(Me)(OH)-(bicyclo [4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and $R^2$ is —$NH_2$ or —$CH_3$.

In yet other embodiments of the compound of Formula IA-2, R¹ is —CH(OH)-2,3-dihydrobenzofuran-6-yl, or —C(Me)(OH)-2,3-dihydrobenzofuran-6-yl; and R² is —NH₂ or —CH₃.

In yet other embodiments of the compound of Formula IA-2, R¹ is —CH(OH)-(5,6-dihydro-4H-cyclopenta[d]thiazol-2-yl) or —C(Me)(OH)-(5,6-dihydro-4H-cyclopenta[d]thiazol-2-yl); and R² is —NH₂ or —CH₃.

In some aspects, the present disclosure is directed to compounds of Formula IB-1

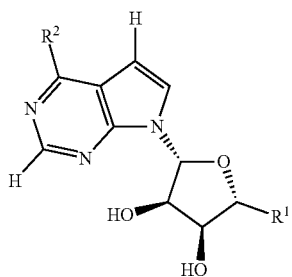

IB-1 wherein R¹ is —CH(OH)-fused aryl, —C(Me)(OH)-fused aryl, —CH(OH)-fused heteroaryl, or C(Me)(OH)-fused heteroaryl; and R² is —C₁-C₆alkyl, —NR⁵R⁵', —NHCONR⁵R⁵', or —NH—O—R⁵; and R⁵ and R⁵' are independently H, C₁-C₆alkyl; or R⁵ and R⁵', together with the atom to which they are attached, form a C₂-C₆heterocycloalkyl.

In some embodiments of the compound of Formula IB-1, R¹ is —CH(OH)-fused aryl, —C(Me)(OH)-fused aryl; and R² is —C₁-C₆alkyl, —NR⁵R⁵', —NHCONR⁵R⁵', or —NH—O—R⁵; and R⁵ and R⁵' are independently H, C₁-C₆alkyl; or R⁵ and R⁵', together with the atom to which they are attached, form a C₂-C₆heterocycloalkyl.

In some embodiments of the compound of Formula IB-1, R¹ is —CH(OH)-fused heteroaryl, or C(Me)(OH)-fused heteroaryl; and R² is —C₁-C₆alkyl, —NR⁵R⁵', —NHCONR⁵R⁵', or —NH—O—R⁵; and R⁵ and R⁵' are independently H, C₁-C₆alkyl; or R⁵ and R⁵', together with the atom to which they are attached, form a C₂-C₆heterocycloalkyl.

In some embodiments of the compound of Formula IB-1, R¹ is —CH(OH)-fused aryl, —C(Me)(OH)-fused aryl; and R² is halo, —C₁-C₆alkyl, —C₂-C₄alkenyl, —C₁-C₆alk-OH, —C₁-C₆alk-halo, —C₁-C₆alk-O—C₁-C₆alkyl, —C₁-C₆alk-O—C₁-C₆alk-aryl, or —O—C₁-C₆alkyl.

In some embodiments of the compound of Formula IB-1, R¹ is —CH(OH)-fused heteroaryl, or C(Me)(OH)-fused heteroaryl; and R² is halo, —C₁-C₆alkyl, —C₂-C₄alkenyl, —C₁-C₆alk-OH, —C₁-C₆alk-halo, —C₁-C₆alk-O—C₁-C₆alkyl, —C₁-C₆alk-O—C₁-C₆alk-aryl, or —O—C₁-C₆alkyl.

In some embodiments of the compound of Formula IB-1, R¹ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and R² is —NH₂, —CH₃, —NH—O—CH₃, —NH—O—CH₂CH₃, —NHCON(CH₃)₂, or

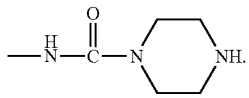

In some embodiments of the compound of Formula IB-1, R¹ is —CH(OH)-(bicyclo[4.2.0]octa-1(6),2,4-trien-3-yl), —CH(OH)-(7-fluorobicyclo[4.2.0]octa-1(6),2,4-trien-3-yl), —CH(OH)-(7,7-difluorobicyclo[4.2.0]octa-1(6),2,4-trien-3-yl); and R² is halo, —C₁-C₆alkyl, —C₂-C₄alkenyl, —C₁-C₆alk-OH, —C₁-C₆alk-halo, —C₁-C₆alk-O—C₁-C₆alkyl, —C₁-C₆alk-O—C₁-C₆alk-aryl, or —O—C₁-C₆alkyl.

In other embodiments of the compound of Formula IB-1, R¹ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and R² is —NH₂, —CH₃, —NH—O—CH₃, —NH—O—CH₂CH₃, —NHCON(CH₃)₂, or

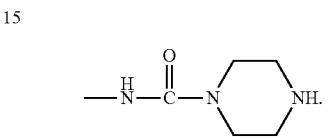

In other embodiments of the compound of Formula IB-1, R¹ is —C(Me)(OH)-(bicyclo[4.2.0]octa-1(6),2,4-trien-3-yl), —C(Me)(OH)-(7-fluorobicyclo[4.2.0]octa-1(6),2,4-trien-3-yl), or —C(Me)(OH)-(7,7-difluorobicyclo[4.2.0]octa-1(6), 2,4-trien-3-yl); and R² is halo, —C₁-C₆alkyl, —C₂-C₄alkenyl, —C₁-C₆alk-OH, —C₁-C₆alk-halo, —C₁-C₆alk-O—C₁-C₆alkyl, —C₁-C₆alk-O—C₁-C₆alk-aryl, or —O—C₁-C₆alkyl.

In other embodiments of the compound of Formula IB-1, R¹ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and R² is —NH₂, —CH₃, —NH—O—CH₃, —NH—O—CH₂CH₃, —NHCON(CH₃)₂, or

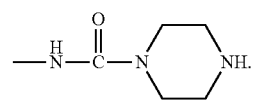

In other embodiments of the compound of Formula IB-1, R¹ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and R² is —NH₂, —CH₃, —NH—O—CH₃, —NH—O—CH₂CH₃, —NHCON(CH₃)₂, or

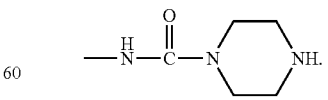

In yet other embodiments of the compound of Formula IB-1, R¹ is —CH(OH)-2,3-dihydrobenzofuran-6-yl, or —C(Me)(OH)-2,3-dihydrobenzofuran-6-yl; and R² is —NH₂, —CH₃, —NH—O—CH₃, —NH—O—CH₂CH₃, —NHCON(CH₃)₂, or

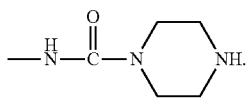

In yet other embodiments of the compound of Formula IB-1, $R^1$ is —CH(OH)-(5,6-dihydro-4H-cyclopenta[d]thiazol-2-yl) or —C(Me)(OH)-(5,6-dihydro-4H-cyclopenta[d]thiazol-2-yl); and $R^2$ is —NH$_2$, —CH$_3$, —NH—O—CH$_3$, —NH—O—CH$_2$CH$_3$, —NHCON(CH$_3$)$_2$, or

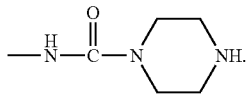

In some aspects, the present disclosure is directed to compounds of Formula IB-2

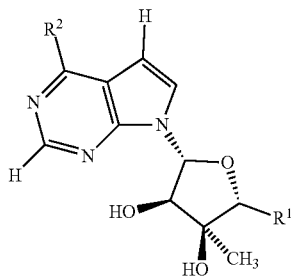

IB-2 wherein $R^1$ is —CH(OH)-fused aryl, —C(Me)(OH)-fused aryl, —CH(OH)-fused heteroaryl, or C(Me)(OH)-fused heteroaryl; and $R^2$ is —C$_1$-C$_6$alkyl, —NR$^5$R$^{5'}$, —NHCONR$^5$R$^{5'}$, or —NH—O—R$^5$; and R5 and R5' are independently H, C$_1$-C$_6$alkyl; or $R^5$ and $R^{5'}$, together with the atom to which they are attached, form a C$_2$-C$_6$heterocycloalkyl.

In some embodiments of the compound of Formula IB-2, $R^1$ is —CH(OH)-fused aryl, or —C(Me)(OH)-fused aryl; and $R^2$ is —C$_1$-C$_6$alkyl, —NR$^5$R$^{5'}$, —NHCONR$^5$R$^{5'}$, or —NH—O—R$^5$; and R5 and R5' are independently H, C$_1$-C$_6$alkyl; or $R^5$ and $R^{5'}$, together with the atom to which they are attached, form a C$_2$-C$_6$heterocycloalkyl.

In some embodiments of the compound of Formula IB-2, $R^1$ is —CH(OH)-fused heteroaryl, or C(Me)(OH)-fused heteroaryl; and $R^2$ is —C$_1$-C$_6$alkyl, —NR$^5$R$^{5'}$, —NHCONR$^5$R$^{5'}$, or —NH—O—R$^5$; and R5 and R5' are independently H, C$_1$-C$_6$alkyl; or $R^5$ and $R^{5'}$, together with the atom to which they are attached, form a C$_2$-C$_6$heterocycloalkyl.

In some embodiments of the compound of Formula IB-2, $R^1$ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and $R^2$ is —NH$_2$, —CH$_3$, —NH—O—CH$_3$, —NH—O—CH$_2$CH$_3$, —NHCON(CH$_3$)$_2$, or

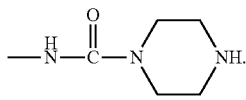

In other embodiments of the compound of Formula IB-2, $R^1$ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and $R^2$ is —NH$_2$, —CH$_3$, —NH—O—CH$_3$, —NH—O—CH$_2$CH$_3$, —NHCON(CH$_3$)$_2$, or

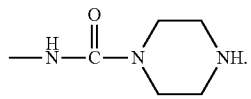

In other embodiments of the compound of Formula IB-2, $R^1$ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and $R^2$ is —NH$_2$, —CH$_3$, —NH—O—CH$_3$, —NH—O—CH$_2$CH$_3$, —NHCON(CH$_3$)$_2$, or

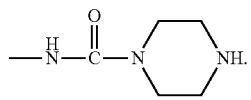

In other embodiments of the compound of Formula IB-2, $R^1$ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and $R^2$ is —NH$_2$, —CH$_3$, —NH—O—CH$_3$, —NH—O—CH$_2$CH$_3$, —NHCON(CH$_3$)$_2$, or

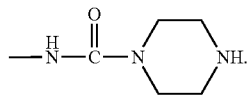

In yet other embodiments of the compound of Formula IB-2, $R^1$ is —CH(OH)-2,3-dihydrobenzofuran-6-yl, or —C(Me)(OH)-2,3-dihydrobenzofuran-6-yl; and $R^2$ is —NH$_2$, —CH$_3$, —NH—O—CH$_3$, —NH—O—CH$_2$CH$_3$, —NHCON(CH$_3$)$_2$, or

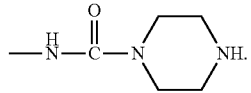

In yet other embodiments of the compound of Formula IB-2, $R^1$ is —CH(OH)-(5,6-dihydro-4H-cyclopenta[d]thiazol-2-yl) or —C(Me)(OH)-(5,6-dihydro-4H-cyclopenta[d]thiazol-2-yl); and $R^2$ is —NH$_2$, —CH$_3$, —NH—O—CH$_3$, —NH—O—CH$_2$CH$_3$, —NHCON(CH$_3$)$_2$, or

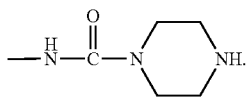

In some aspects, the present disclosure is directed to compounds of Formula IC-1:

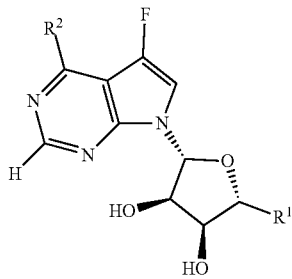

IC-1 wherein R¹ is —CH(OH)-fused aryl, —C(Me)(OH)-fused aryl, —CH(OH)-fused heteroaryl, or C(Me)(OH)-fused heteroaryl; and R² is —$C_1$-$C_6$alkyl, —NR⁵R⁵', —NHCONR⁵R⁵', or —NH—O—R⁵; and R⁵ and R⁵' are independently H, $C_1$-$C_6$alkyl; or R⁵ and R⁵', together with the atom to which they are attached, form a $C_2$-$C_6$heterocycloalkyl.

In some embodiments of the compound of Formula IC-1, R¹ is —CH(OH)-fused aryl, or —C(Me)(OH)-fused aryl; and R² is —$C_1$-$C_6$alkyl, —NR⁵R⁵', —NHCONR⁵R⁵', or —NH—O—R⁵; and R⁵ and R⁵' are independently H, $C_1$-$C_6$alkyl; or R⁵ and R⁵', together with the atom to which they are attached, form a $C_2$-$C_6$heterocycloalkyl.

In some embodiments of the compound of Formula IC-1, R¹ is —CH(OH)-fused heteroaryl, or C(Me)(OH)-fused heteroaryl; and R² is —$C_1$-$C_6$alkyl, —NR⁵R⁵', —NHCONR⁵R⁵', or —NH—O—R⁵; and R⁵ and R⁵' are independently H, $C_1$-$C_6$alkyl; or R⁵ and R⁵', together with the atom to which they are attached, form a $C_2$-$C_6$heterocycloalkyl.

In some embodiments of the compound of Formula IC-1, R¹ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and R² is —NH₂, —CH₃, —NH—O—CH₃, —NH—O—CH₂CH₃, —NHCON(CH₃)₂, or

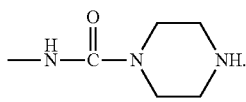

In other embodiments of the compound of Formula IC-1, R¹ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and R² is —NH₂, —CH₃, —NH—O—CH₃, —NH—O—CH₂CH₃, —NHCON(CH₃)₂, or

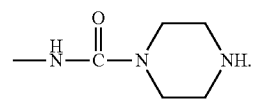

In other embodiments of the compound of Formula IC-1, R¹ is —CH(OH)-(7-methylbicyclo[4.2.0]octa-1(6),2,4-trien-3-yl), —CH(OH)-(7,7-dimethylbicyclo[4.2.0]octa-1(6),2,4-trien-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and R² is —NH₂, —CH₃, —NH—O—CH₃, —NH—O—CH₂CH₃, —NHCON(CH₃)₂, or

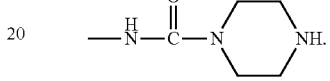

In other embodiments of the compound of Formula IC-1, R¹ is —C(Me)(OH)-(7-methylbicyclo[4.2.0]octa-1(6),2,4-trien-3-yl), —C(Me)(OH)-(7,7-dimethylbicyclo[4.2.0]octa-1(6),2,4-trien-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and R² is —NH₂, —CH₃, —NH—O—CH₃, —NH—O—CH₂CH₃, —NHCON(CH₃)₂, or

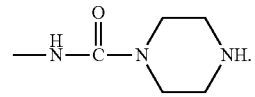

In yet other embodiments of the compound of Formula IC-1, R¹ is —CH(OH)-2,3-dihydrobenzofuran-6-yl, or —C(Me)(OH)-2,3-dihydrobenzofuran-6-yl; and R² is —NH₂, —CH₃, —NH—O—CH₃, —NH—O—CH₂CH₃, —NHCON(CH₃)₂, or

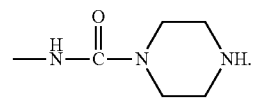

In yet other embodiments of the compound of Formula IC-1, R¹ is —CH(OH)-(5,6-dihydro-4H-cyclopenta[d]thiazol-2-yl) or —C(Me)(OH)-(5,6-dihydro-4H-cyclopenta[d]thiazol-2-yl); and R² is —NH₂, —CH₃, —NH—O—CH₃, —NH—O—CH₂CH₃, —NHCON(CH₃)₂, or

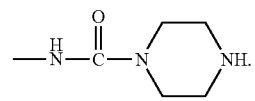

In some aspects, the present disclosure is directed to compounds of Formula IC-2:

IC-2

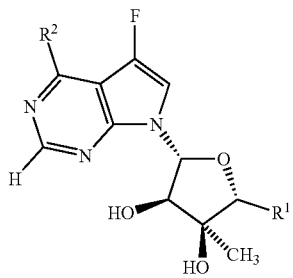

wherein $R^1$ is —CH(OH)-fused aryl, —C(Me)(OH)-fused aryl, —CH(OH)-fused heteroaryl, or C(Me)(OH)-fused heteroaryl; and $R^2$ is —$C_1$-$C_6$alkyl, —$NR^5R^{5'}$, —$NHCONR^5R^{5'}$, or —NH—O—$R^5$; and $R^5$ and $R^{5'}$ are independently H, $C_1$-$C_6$alkyl; or $R^5$ and $R^{5'}$, together with the atom to which they are attached, form a $C_2$-$C_6$heterocycloalkyl.

In some embodiments of the compound of Formula IC-2, $R^1$ is —CH(OH)-fused aryl, or —C(Me)(OH)-fused aryl; and $R^2$ is —$C_1$-$C_6$alkyl, —$NR^5R^{5'}$, —$NHCONR^5R^{5'}$, or —NH—O—$R^5$; and $R^5$ and $R^{5'}$ are independently H, $C_1$-$C_6$alkyl; or $R^5$ and $R^{5'}$, together with the atom to which they are attached, form a $C_2$-$C_6$heterocycloalkyl.

In some embodiments of the compound of Formula IC-2, $R^1$ is —CH(OH)-fused heteroaryl, or C(Me)(OH)-fused heteroaryl; and $R^2$ is —$C_1$-$C_6$alkyl, —$NR^5R^{5'}$, —$NHCONR^5R^{5'}$, or —NH—O—$R^5$; and $R^5$ and $R^{5'}$ are independently H, $C_1$-$C_6$alkyl; or $R^5$ and $R^{5'}$, together with the atom to which they are attached, form a $C_2$-$C_6$heterocycloalkyl.

In some embodiments of the compound of Formula IC-2, $R^1$ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and $R^2$ is —$NH_2$, —$CH_3$, —NH—O—$CH_3$, —NH—O—$CH_2CH_3$, —$NHCON(CH_3)_2$, or

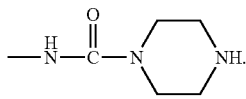

In other embodiments of the compound of Formula IC-2, $R^1$ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and $R^2$ is —$NH_2$, —$CH_3$, —NH—O—$CH_3$, —NH—O—$CH_2CH_3$, —$NHCON(CH_3)_2$, or

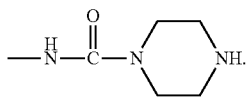

In other embodiments of the compound of Formula IC-2, $R^1$ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and $R^2$ is —$NH_2$, —$CH_3$, —NH—O—$CH_3$, —NH—O—$CH_2CH_3$, —$NHCON(CH_3)_2$, or

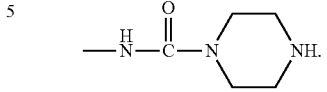

In other embodiments of the compound of Formula IC-2, $R^1$ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and $R^2$ is —$NH_2$, —$CH_3$, —NH—O—$CH_3$, —NH—O—$CH_2CH_3$, —$NHCON(CH_3)_2$, or

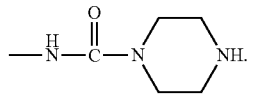

In yet other embodiments of the compound of Formula IC-2, $R^1$ is —CH(OH)-2,3-dihydrobenzofuran-6-yl, or —C(Me)(OH)-2,3-dihydrobenzofuran-6-yl; and $R^2$ is —$NH_2$, —$CH_3$, —NH—O—$CH_3$, —NH—O—$CH_2CH_3$, —$NHCON(CH_3)_2$, or

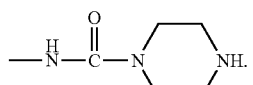

In yet other embodiments of the compound of Formula IC-2, $R^1$ is —CH(OH)-(5,6-dihydro-4H-cyclopenta[d]thiazol-2-yl) or —C(Me)(OH)-(5,6-dihydro-4H-cyclopenta[d]thiazol-2-yl); and $R^2$ is —$NH_2$, —$CH_3$, —NH—O—$CH_3$, —NH—O—$CH_2CH_3$, —$NHCON(CH_3)_2$, or

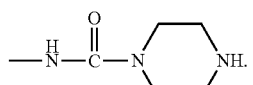

In some aspects, the present disclosure is directed to compounds of Formula IIA-1

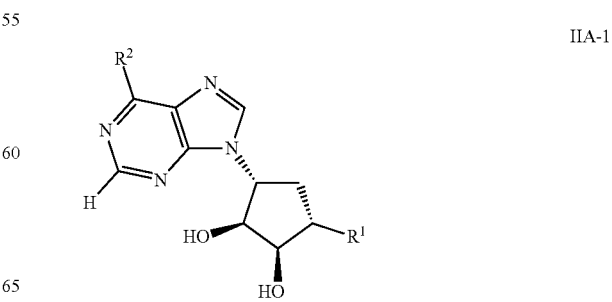

wherein R¹ is —CH(OH)-fused aryl, —C(Me)(OH)-fused aryl, —CH(OH)-fused heteroaryl, or C(Me)(OH)-fused heteroaryl; and R² is —NH₂ or —CH₃.

In some embodiments of the compound of Formula IIA-1, R¹ is —CH(OH)-fused aryl, or —C(Me)(OH)-fused aryl; and R² is —NH₂ or —CH₃.

In some embodiments of the compound of Formula IIA-1, R¹ is —CH(OH)-fused heteroaryl, or C(Me)(OH)-fused heteroaryl; and R² is —NH₂ or —CH₃.

In some embodiments of the compound of Formula IIA-1, R¹ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and R² is —NH₂ or —CH₃.

In other embodiments of the compound of Formula IIA-1, R¹ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and R² is —NH₂ or —CH₃.

In other embodiments of the compound of Formula IIA-1, R¹ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and R² is —NH₂ or —CH₃.

In other embodiments of the compound of Formula IIA-1, R¹ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and R² is —NH₂ or —CH₃.

In yet other embodiments of the compound of Formula IIA-1, R¹ is —CH(OH)-2,3-dihydrobenzofuran-6-yl, or —C(Me)(OH)-2,3-dihydrobenzofuran-6-yl; and R² is —NH₂ or —CH₃.

In yet other embodiments of the compound of Formula IIA-1, R¹ is —CH(OH)-(5,6-dihydro-4H-cyclopenta[d]thiazol-2-yl) or —C(Me)(OH)-(5,6-dihydro-4H-cyclopenta[d]thiazol-2-yl); and R² is —NH₂ or —CH₃.

In some aspects, the present disclosure is directed to compounds of Formula IIA-2

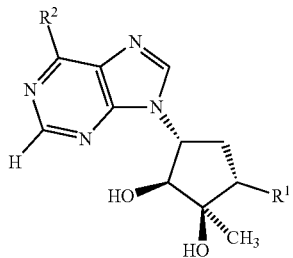

IIA-2 wherein R¹ is —CH(OH)-fused aryl, —C(Me)(OH)-fused aryl, —CH(OH)-fused heteroaryl, or C(Me)(OH)-fused heteroaryl; and R² is —NH₂ or —CH₃.

In some embodiments of the compound of Formula IIA-2, R¹ is —CH(OH)-fused aryl, or —C(Me)(OH)-fused aryl, and R² is —NH₂ or —CH₃.

In some embodiments of the compound of Formula IIA-2, R¹ is —CH(OH)-fused heteroaryl, or C(Me)(OH)-fused heteroaryl; and R² is —NH₂ or —CH₃.

In some embodiments of the compound of Formula IIA-2, R¹ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and R² is —NH₂ or —CH₃.

In other embodiments of the compound of Formula IIA-2, R¹ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and R² is —NH₂ or —CH₃.

In other embodiments of the compound of Formula IIA-2, R¹ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and R² is —NH₂ or —CH₃.

In other embodiments of the compound of Formula IIA-2, R¹ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and R² is —NH₂ or —CH₃.

In yet other embodiments of the compound of Formula IIA-2, R¹ is —CH(OH)-2,3-dihydrobenzofuran-6-yl, or —C(Me)(OH)-2,3-dihydrobenzofuran-6-yl; and R² is —NH₂ or —CH₃.

In yet other embodiments of the compound of Formula IIA-2, R¹ is —CH(OH)-(5,6-dihydro-4H-cyclopenta[d]thiazol-2-yl) or —C(Me)(OH)-(5,6-dihydro-4H-cyclopenta[d]thiazol-2-yl); and R² is —NH₂ or —CH₃.

In some aspects, the present disclosure is directed to compounds of Formula IIB-1

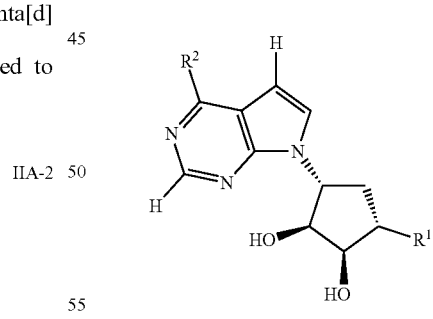

IIB-1 wherein R¹ is —CH(OH)-fused aryl, —C(Me)(OH)-fused aryl, —CH(OH)-fused heteroaryl, or C(Me)(OH)-fused heteroaryl; and R² is —C₁-C₆alkyl, —NR⁵R⁵', —NHCONR⁵R⁵', or —NH—O—R⁵; and R5 and R5' are independently H, C₁-C₆alkyl; or R⁵ and R⁵', together with the atom to which they are attached, form a C₂-C₆heterocycloalkyl.

In some embodiments of the compound of Formula IIB-1, R¹ is —CH(OH)-fused aryl, —C(Me)(OH)-fused aryl; and R² is —C₁-C₆alkyl, —NR⁵R⁵', —NHCONR⁵R⁵', or —NH—O—R⁵; and R⁵ and R⁵' are independently H, $C_1$-$C_6$alkyl; or $R^5$ and $R^{5'}$, together with the atom to which they are attached, form a $C_2$-$C_6$heterocycloalkyl.

In some embodiments of the compound of Formula IIB-1, $R^1$ is —CH(OH)-fused heteroaryl, or C(Me)(OH)-fused heteroaryl; and $R^2$ is —$C_1$-$C_6$alkyl, —$NR^5R^{5'}$, —$NHCONR^5R^{5'}$, or —NH—O—$R^5$; and $R^5$ and $R^{5'}$ are independently H, $C_1$-$C_6$alkyl; or $R^5$ and $R^{5'}$, together with the atom to which they are attached, form a $C_2$-$C_6$heterocycloalkyl.

In some embodiments of the compound of Formula IIB-1, $R^1$ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and $R^2$ is —$NH_2$, —$CH_3$, —NH—O—$CH_3$, —NH—O—$CH_2CH_3$, —$NHCON(CH_3)_2$, or

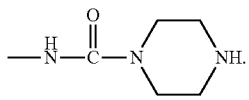

In other embodiments of the compound of Formula IIB-1, $R^1$ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and $R^2$ is —$NH_2$, —$CH_3$, —NH—O—$CH_3$, —NH—O—$CH_2CH_3$, —$NHCON(CH_3)_2$, or

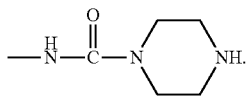

In other embodiments of the compound of Formula IIB-1, $R^1$ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and $R^2$ is —$NH_2$, —$CH_3$, —NH—O—$CH_3$, —NH—O—$CH_2CH_3$, —$NHCON(CH_3)_2$, or

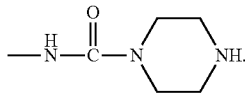

In other embodiments of the compound of Formula IIB-1, $R^1$ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and $R^2$ is —$NH_2$, —$CH_3$, —NH—O—$CH_3$, —NH—O—$CH_2CH_3$, —$NHCON(CH_3)_2$, or

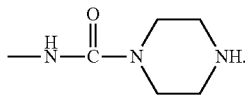

In yet other embodiments of the compound of Formula IIB-1, $R^1$ is —CH(OH)-2,3-dihydrobenzofuran-6-yl, or —C(Me)(OH)-2,3-dihydrobenzofuran-6-yl; and $R^2$ is —$NH_2$, —$CH_3$, —NH—O—$CH_3$, —NH—O—$CH_2CH_3$, —$NHCON(CH_3)_2$, or

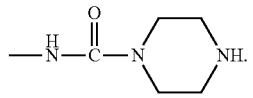

In yet other embodiments of the compound of Formula IIB-1, $R^1$ is —CH(OH)-(5,6-dihydro-4H-cyclopenta[d]thiazol-2-yl) or —C(Me)(OH)-(5,6-dihydro-4H-cyclopenta[d]thiazol-2-yl); and $R^2$ is —$NH_2$, —$CH_3$, —NH—O—$CH_3$, —NH—O—$CH_2CH_3$, —$NHCON(CH_3)_2$, or

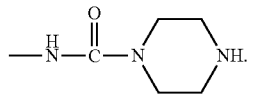

In some aspects, the present disclosure is directed to compounds of Formula IIB-2

IIB-2

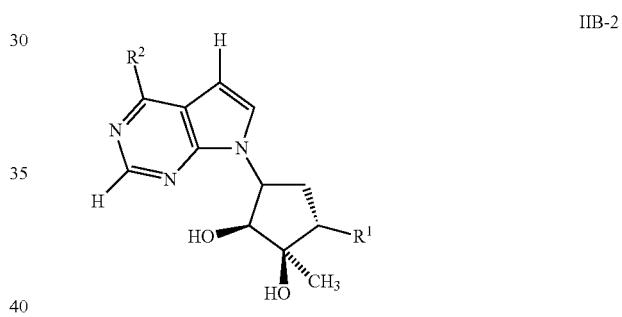

wherein $R^1$ is —CH(OH)-fused aryl, —C(Me)(OH)-fused aryl, —CH(OH)-fused heteroaryl, or C(Me)(OH)-fused heteroaryl; and $R^2$ is —$C_1$-$C_6$alkyl, —$NR^5R^{5'}$, —$NHCONR^5R^{5'}$, or —NH—O—$R^5$; and R5 and R5' are independently H, $C_1$-$C_6$alkyl; or $R^5$ and $R^{5'}$, together with the atom to which they are attached, form a $C_2$-$C_6$heterocycloalkyl.

In some embodiments of the compound of Formula IIB-2, $R^1$ is —CH(OH)-fused aryl, or —C(Me)(OH)-fused aryl; and $R^2$ is —$C_1$-$C_6$alkyl, —$NR^5R^{5'}$, —$NHCONR^5R^{5'}$, or —NH—O—$R^5$; and R5 and R5' are independently H, $C_1$-$C_6$alkyl; or $R^5$ and $R^{5'}$, together with the atom to which they are attached, form a $C_2$-$C_6$heterocycloalkyl.

In some embodiments of the compound of Formula IIB-2, $R^1$ is —CH(OH)-fused heteroaryl, or C(Me)(OH)-fused heteroaryl; and $R^2$ is —$C_1$-$C_6$alkyl, —$NR^5R^{5'}$, —$NHCONR^5R^{5'}$, or —NH—O—$R^5$; and R5 and R5' are independently H, $C_1$-$C_6$alkyl; or $R^5$ and $R^{5'}$, together with the atom to which they are attached, form a $C_2$-$C_6$heterocycloalkyl.

In some embodiments of the compound of Formula IIB-2, $R^1$ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and $R^2$ is —$NH_2$, —$CH_3$, —NH—O—$CH_3$, —NH—O—$CH_2CH_3$, —$NHCON(CH_3)_2$, or

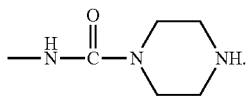

In other embodiments of the compound of Formula IIB-2, $R^1$ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and $R^2$ is —NH$_2$, —CH$_3$, —NH—O—CH$_3$, —NH—O—CH$_2$CH$_3$, —NHCON(CH$_3$)$_2$, or

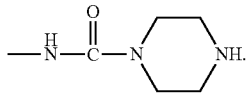

In other embodiments of the compound of Formula IIB-2, $R^1$ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and $R^2$ is —NH$_2$, —CH$_3$, —NH—O—CH$_3$, —NH—O—CH$_2$CH$_3$, —NHCON(CH$_3$)$_2$, or

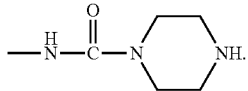

In other embodiments of the compound of Formula IIB-2, $R^1$ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and $R^2$ is —NH$_2$, —CH$_3$, —NH—O—CH$_3$, —NH—O—CH$_2$CH$_3$, —NHCON(CH$_3$)$_2$, or

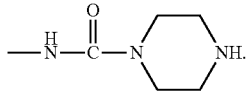

In yet other embodiments of the compound of Formula IIB-2, $R^1$ is —CH(OH)-2,3-dihydrobenzofuran-6-yl, or —C(Me)(OH)-2,3-dihydrobenzofuran-6-yl; and $R^2$ is —NH$_2$, —CH$_3$, —NH—O—CH$_3$, —NH—O—CH$_2$CH$_3$, —NHCON(CH$_3$)$_2$, or

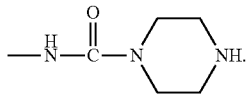

In yet other embodiments of the compound of Formula IIB-2, $R^1$ is —CH(OH)-(5,6-dihydro-4H-cyclopenta[d]thiazol-2-yl) or —C(Me)(OH)-(5,6-dihydro-4H-cyclopenta[d]thiazol-2-yl); and $R^2$ is —NH$_2$, —CH$_3$, —NH—O—CH$_3$, —NH—O—CH$_2$CH$_3$, —NHCON(CH$_3$)$_2$, or

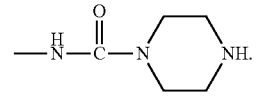

In some aspects, the present disclosure is directed to compounds of Formula IIC-1:

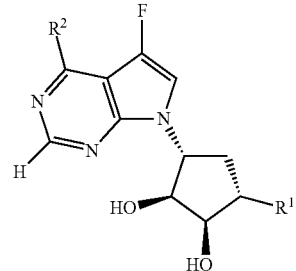

IIC-1 wherein $R^1$ is —CH(OH)-fused aryl, —C(Me)(OH)-fused aryl, —CH(OH)-fused heteroaryl, or C(Me)(OH)-fused heteroaryl; and $R^2$ is —C$_1$-C$_6$alkyl, —NR$^5$R$^{5'}$, —NHCONR$^5$R$^{5'}$, or —NH—O—R$^5$; and $R^5$ and $R^{5'}$ are independently H, C$_1$-C$_6$alkyl; or $R^5$ and $R^{5'}$, together with the atom to which they are attached, form a C$_2$-C$_6$heterocycloalkyl.

In some embodiments of the compound of Formula IIC-1, $R^1$ is —CH(OH)-fused aryl, or —C(Me)(OH)-fused aryl; and $R^2$ is —C$_1$-C$_6$alkyl, —NR$^5$R$^{5'}$, —NHCONR$^5$R$^{5'}$, or —NH—O—R$^5$; and $R^5$ and $R^{5'}$ are independently H, C$_1$-C$_6$alkyl; or $R^5$ and $R^{5'}$, together with the atom to which they are attached, form a C$_2$-C$_6$heterocycloalkyl.

In some embodiments of the compound of Formula IIC-1, $R^1$ is —CH(OH)-fused heteroaryl, or C(Me)(OH)-fused heteroaryl; and $R^2$ is —C$_1$-C$_6$alkyl, —NR$^5$R$^{5'}$, —NHCONR$^5$R$^{5'}$, or —NH—O—R$^5$; and $R^5$ and $R^{5'}$ are independently H, C$_1$-C$_6$alkyl; or $R^5$ and $R^{5'}$, together with the atom to which they are attached, form a C$_2$-C$_6$heterocycloalkyl.

In some embodiments of the compound of Formula IIC-1, $R^1$ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and $R^2$ is —NH$_2$, —CH$_3$, —NH—O—CH$_3$, —NH—O—CH$_2$CH$_3$, —NHCON(CH$_3$)$_2$, or

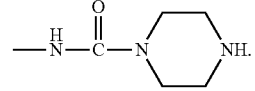

In other embodiments of the compound of Formula IIC-1, $R^1$ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and $R^2$ is —NH$_2$, —CH$_3$, —NH—O—CH$_3$, —NH—O—CH$_2$CH$_3$, —NHCON(CH$_3$)$_2$, or

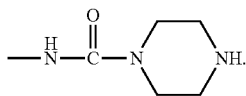

In other embodiments of the compound of Formula IIC-1, $R^1$ is —CH(OH)-(7-methylbicyclo[4.2.0]octa-1(6),2,4-trien-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3-dihydro-1H-inden-5-yl); and $R^2$ is —NH$_2$, —CH$_3$, —NH—O—CH$_3$, —NH—O—CH$_2$CH$_3$, —NHCON(CH$_3$)$_2$, or

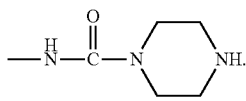

In other embodiments of the compound of Formula IIC-1, $R^1$ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and $R^2$ is —NH$_2$, —CH$_3$, —NH—O—CH$_3$, —NH—O—CH$_2$CH$_3$, —NHCON(CH$_3$)$_2$, or

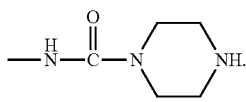

In yet other embodiments of the compound of Formula IIC-1, $R^1$ is —CH(OH)-2,3-dihydrobenzofuran-6-yl, or —C(Me)(OH)-2,3-dihydrobenzofuran-6-yl; and $R^2$ is —NH$_2$, —CH$_3$, —NH—O—CH$_3$, —NH—O—CH$_2$CH$_3$, —NHCON(CH$_3$)$_2$, or

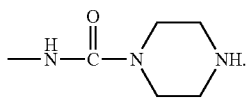

In yet other embodiments of the compound of Formula IIC-1, $R^1$ is —CH(OH)-(5,6-dihydro-4H-cyclopenta[d]thiazol-2-yl) or —C(Me)(OH)-(5,6-dihydro-4H-cyclopenta[d]thiazol-2-yl); and $R^2$ is —NH$_2$, —CH$_3$, —NH—O—CH$_3$, —NH—O—CH$_2$CH$_3$, —NHCON(CH$_3$)$_2$, or

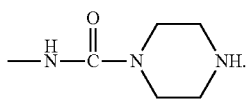

In some aspects, the present disclosure is directed to compounds of Formula IIC-2:

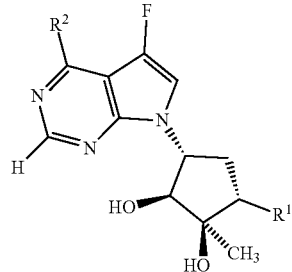

IIC-2 wherein $R^1$ is —CH(OH)-fused aryl, —C(Me)(OH)-fused aryl, —CH(OH)-fused heteroaryl, or C(Me)(OH)-fused heteroaryl; and $R^2$ is —C$_1$-C$_6$alkyl, —NR$^5$R$^{5'}$, —NHCONR$^5$R$^{5'}$, or —NH—O—R$^5$; and R$^5$ and R$^{5'}$ are independently H, C$_1$-C$_6$alkyl; or R$^5$ and R$^{5'}$, together with the atom to which they are attached, form a C$_2$-C$_6$heterocycloalkyl.

In some embodiments of the compound of Formula IIC-2, $R^1$ is —CH(OH)-fused aryl, or —C(Me)(OH)-fused aryl; and $R^2$ is —C$_1$-C$_6$alkyl, —NR$^5$R$^{5'}$, —NHCONR$^5$R$^{5'}$, or —NH—O—R$^5$; and R$^5$ and R$^{5'}$ are independently H, C$_1$-C$_6$alkyl; or R$^5$ and R$^{5'}$, together with the atom to which they are attached, form a C$_2$-C$_6$heterocycloalkyl.

In some embodiments of the compound of Formula IIC-2, $R^1$ is —CH(OH)-fused heteroaryl, or C(Me)(OH)-fused heteroaryl; and $R^2$ is —C$_1$-C$_6$alkyl, —NR$^5$R$^{5'}$, —NHCONR$^5$R$^{5'}$, or —NH—O—R$^5$; and R$^5$ and R$^{5'}$ are independently H, C$_1$-C$_6$alkyl; or R$^5$ and R$^{5'}$, together with the atom to which they are attached, form a C$_2$-C$_6$heterocycloalkyl.

In some embodiments of the compound of Formula IIC-2, $R^1$ is —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl; and $R^2$ is —NH$_2$, —CH$_3$, —NH—O—CH$_3$, —NH—O—CH$_2$CH$_3$, —NHCON(CH$_3$)$_2$, or

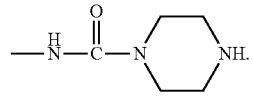

In other embodiments of the compound of Formula IIC-2, $R^1$ is —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl; and $R^2$ is —NH$_2$, —CH$_3$, —NH—O—CH$_3$, —NH—O—CH$_2$CH$_3$, —NHCON(CH$_3$)$_2$, or

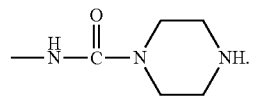

In other embodiments of the compound of Formula IIC-2, $R^1$ is —CH(OH)-(7-methylbicyclo[4.2.0]octa-1(6),2,4-triene-3-yl), —CH(OH)-(7,7-dimethylbicyclo[4.2.0]octa-1(6),2,4-triene-3-yl), —CH(OH)-(bicyclo[4.2.0]octa-1(6),2,4-trien-7-ol-3-yl), —CH(OH)-(bicyclo[4.2.0]octa-1(6),2,4-trien-7-one-3-yl), —CH(OH)-(7-methylbicyclo[4.2.0]octa-1(6),2,4-triene-7-carbonitrile-3-yl), or —CH(OH)-(2,3- dihydro-1H-inden-5-yl); and R² is —NH₂, —CH₃, —NH—O—CH₃, —NH—O—CH₂CH₃, —NHCON(CH₃)₂, or

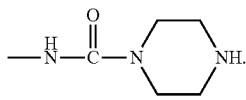

In other embodiments of the compound of Formula IIC-2, R¹ is —C(Me)(OH)-(7-methylbicyclo[4.2.0]octa-1(6),2,4-triene-3-yl), —C(Me)(OH)-(7,7-dimethylbicyclo[4.2.0]octa-1(6),2,4-triene-3-yl), —C(Me)(OH)-(bicyclo[4.2.0]octa-1(6),2,4-trien-7-ol-3-yl), —C(Me)(OH)-(bicyclo[4.2.0]octa-1(6),2,4-trien-7-one-3-yl), —C(Me)(OH)-(7-methylbicyclo[4.2.0]octa-1(6),2,4-triene-7-carbonitrile-3-yl), or —C(Me)(OH)-(2,3-dihydro-1H-inden-5-yl); and R² is —NH₂, —CH₃, —NH—O—CH₃, —NH—O—CH₂CH₃, —NHCON(CH₃)₂, or

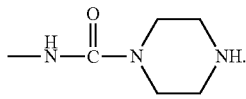

In yet other embodiments of the compound of Formula IIC-2, R¹ is —CH(OH)-2,3-dihydrobenzofuran-6-yl, or —C(Me)(OH)-2,3-dihydrobenzofuran-6-yl; and R² is —NH₂, —CH₃, —NH—O—CH₃, —NH—O—CH₂CH₃, —NHCON(CH₃)₂, or

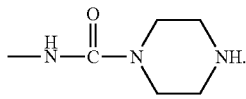

In yet other embodiments of the compound of Formula IIC-2, R¹ is —CH(OH)-(5,6-dihydro-4H-cyclopenta[d]thiazol-2-yl) or —C(Me)(OH)-(5,6-dihydro-4H-cyclopenta[d]thiazol-2-yl); and R² is —NH₂, —CH₃, —NH—O—CH₃, —NH—O—CH₂CH₃, —NHCON(CH₃)₂, or

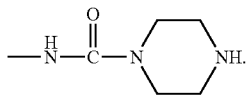

References to Formula I herein also refer to Formulas IA, IA-1, IA-2, IB, IB-1, IB-2, IC-1, and IC-2. References to Formula II herein also refer to Formulas IIA, IIA-1, IIA-2, IIB, IIB-1, IIB-2, IIC-1, and IIC-2.

Stereoisomers of compounds of Formula I and Formula II are also contemplated by the present disclosure. Thus, the disclosure encompasses all stereoisomers and constitutional isomers of any compound disclosed or claimed herein, including all enantiomers and diastereomers.

Pharmaceutically acceptable salts and solvates of the compounds of Formula I and Formula II are also within the scope of the disclosure.

Isotopic variants of the compounds of Formula I and Formula II are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range.

For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof, carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, F-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25% o, 50%), 100% o, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art.

See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a PRMT5 inhibitor with an IC50 value of about or less than a predetermined value, as ascertained in an in vitro assay. In some embodiments, the PRMT5 inhibitor inhibits PRMT5 a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 µM, 100 µM, 200 µM, 300 µM, 400 µM, or 500 µM, or less, (or a number in the range defined by and including any two numbers above).

In some embodiments, the PRMT5 inhibitor selectively inhibits PRMT5 a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other PRMTs.

In some embodiments, the PRMT5 inhibitor selectively inhibits PRMT5 a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other PRMTs.

The subject methods are useful for treating a disease condition associated with PRMT5. Any disease condition that results directly or indirectly from an abnormal activity or expression level of PRMT5 can be an intended disease condition.

Different disease conditions associated with PRMT5 have been reported. PRMT5 has been implicated, for example, in a variety of human cancers as well as a number of hemoglobinopathies.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, said method is for treating a disease selected from breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

In yet other embodiments, said method is for treating a disease selected from CDKN2A deleted cancers; 9P deleted cancers; MTAP deleted cancers; glioblastoma multiforme (GBM), NSCLC, head and neck cancer, bladder cancer, or hepatocellular carcinoma.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

In other aspects, compounds of the disclosure, as well as pharmaceutical compositions comprising them, can be administered to treat any of the described diseases, alone or in combination with one or more other chemotherapeutic agents. Examples of other chemotherapeutic agents include, for example, abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat, and zoledronate, as well as any combination thereof.

In other aspects, the other agent is a therapeutic agent that targets an epigenetic regulator. Examples of epigenetic regulator agents include, for example, bromodomain inhibitors, the histone lysine methyltransferases, histone arginine methyl transferases, histone demethylases, histone deacetylases, histone acetylases, and DNA methyltransferases, as well as any combination thereof. Histone deacetylase inhibitors are preferred in some aspects, and include, for example, vorinostat.

In other methods wherein the disease to be treated is cancer or another proliferative disease, the compounds of the disclosure, as well as pharmaceutical compositions comprising them, can be administered in combination with targeted therapy agents. Targeted therapies include, for example, JAK kinase inhibitors (e.g. Ruxolitinib), PI3 kinase inhibitors (including PI3K-delta selective and broad spectrum PI3K inhibitors), MEK inhibitors, Cyclin Dependent kinase inhibitors (e.g, CDK4/6 inhibitors), BRAF inhibitors, mTOR inhibitors, proteasome inhibitors (e.g., Bortezomib, Carfilzomib), HDAC-inhibitors (e.g., panobinostat, vorinostat), DNA methyl transferase inhibitors, dexamethasone, bromo and extra terminal family members, BTK inhibitors (e.g., ibrutinib, acalabrutinib), BCL2 inhibitors (e.g., venetoclax), MCL1 inhibitors, PARP inhibitors, FLT3 inhibitors, and LSD1 inhibitors, as well as any combination thereof.

In other methods wherein the disease to be treated is cancer or another proliferative disease, the compounds of the disclosure, as well as pharmaceutical compositions comprising them, can be administered in combination with an immune checkpoint inhibitor agents. Immune checkpoint inhibitors include, for example, inhibitors of PD-1, for example, an anti-PD-1 monoclonal antibody. Examples of anti-PD-1 monoclonal antibodies include, for example, nivolumab, pembrolizumab (also known as MK-3475), pidilizumab, SHR-1210, PDR001, and AMP-224, as well as combinations thereof. In some aspects, the anti-PD1 antibody is nivolumab. In some aspects, the anti-PD1 antibody is pembrolizumab. In some aspects, the immunce checkpoint inhibitor is an inhibitor of PD-L1, for example, an anti-PD-L1 monoclonal antibody. In some aspects, the anti-PD-L1 monoclonal antibody is BMS-935559, MEDI4736, MPDL3280A (also known as RG7446), or MSB0010718C, or any combination thereof. In some aspects, the anti-PD-L1 monoclonal antibody is MPDL3280A or MEDI4736. In other aspects, the immune checkpoint inhibitor is an inhibitor of CTLA-4, for example, and anti-CTLA-4 antibody. In some aspects, the anti-CTLA-4 antibody is ipilimumab.

In other methods wherein the disease to be treated is cancer or another proliferative disease, the compounds of the disclosure, as well as pharmaceutical compositions comprising them, can be administered in combination with an alkylating agent (e.g., cyclophosphamide (CY), melphalan (MEL), and bendamustine), a proteasome inhibitor agent (e.g., carfilzomib), a corticosteroid agent (e.g., dexamethasone (DEX)), or an immunomodulatory agent (e.g., lenalidomide (LEN) or pomalidomide (POM)), or any combination thereof.

In some embodiments, the disease to be treated is an autoimmune condition or an inflammatory condition. In these aspects, the compounds of the disclosure, as well as pharmaceutical compositions comprising them, can be administered in combination with a corticosteroid agent such as, for example, triamcinolone, dexamethasone, fluocinolone, cortisone, prednisolone, or flumetholone, or any combination thereof.

In other methods wherein the disease to be treated is an autoimmune condition or an inflammatory condition, the compounds of the disclosure, as well as pharmaceutical compositions comprising them, can be administered in combination with an immune suppressant agent such as, for example, fluocinolone acetonide (RETISERT™), rimexolone (AL-2178, VEXOL™, ALCO™), or cyclosporine (RESTASIS™), or any combination thereof.

In some embodiments, the disease to be treated is beta-thalassemia or sickle cell disease. In these aspects, the compounds of the disclosure, as well as pharmaceutical compositions comprising them, can be administered in combination with one or more agents such as, for example, HYDREA™ (hydroxyurea).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Compounds of the disclosure can be prepared, for example, by reference to the following schemes.

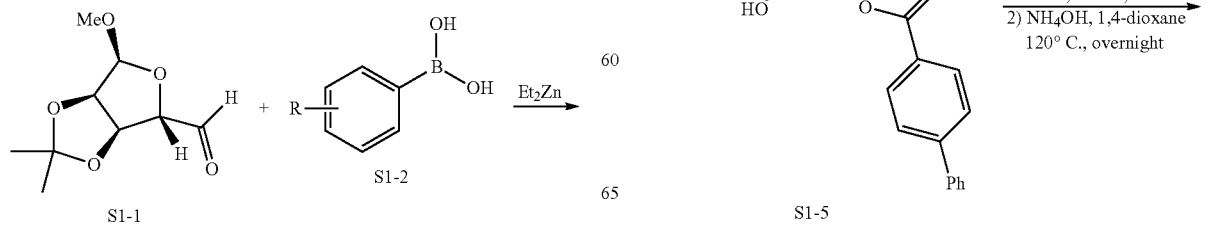

-continued
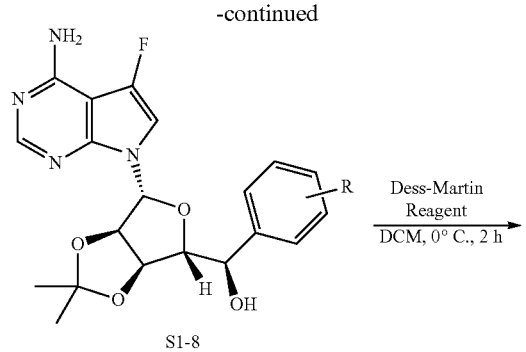
S1-8
Dess-Martin Reagent
DCM, 0° C., 2 h →
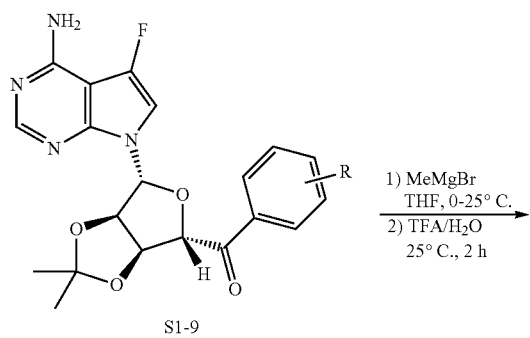
S1-9
1) MeMgBr
THF, 0-25° C.
2) TFA/H₂O
25° C., 2 h →
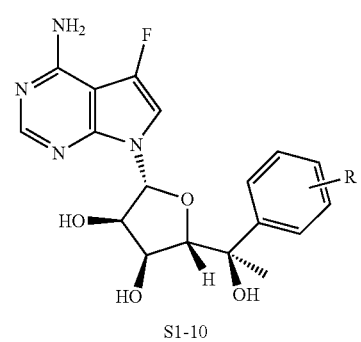
S1-10
Scheme 2
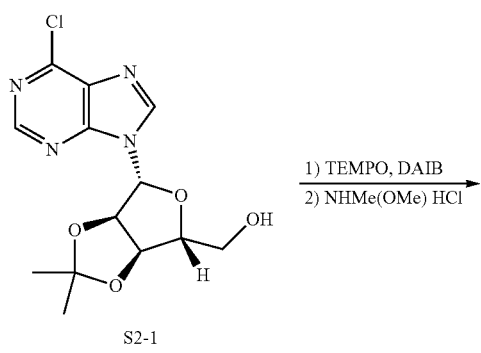
S2-1
1) TEMPO, DAIB
2) NHMe(OMe) HCl →
-continued
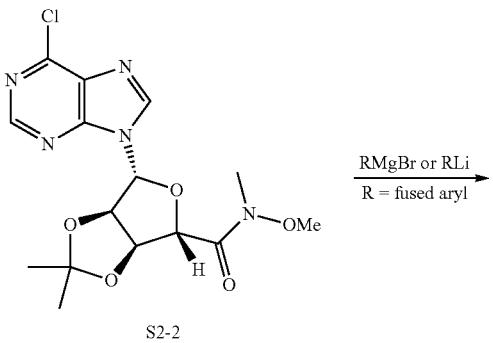
S2-2
RMgBr or RLi
R = fused aryl →
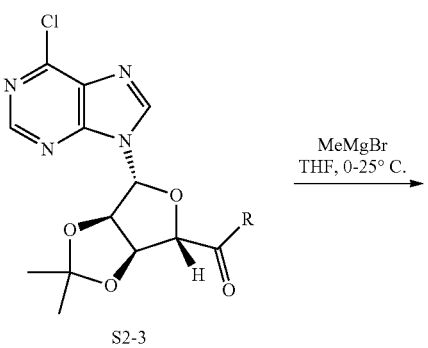
S2-3
MeMgBr
THF, 0-25° C. →
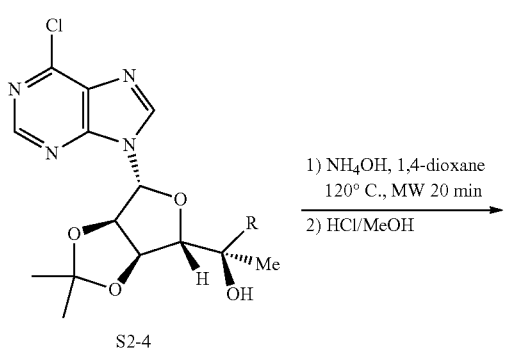
S2-4
1) NH₄OH, 1,4-dioxane
120° C., MW 20 min
2) HCl/MeOH →
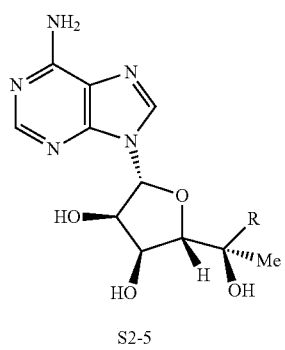
S2-5

Compounds of the disclosure include, for example, the compounds identified in Table A.

TABLE A

| Example No. | Structure | MW | Chemical Name |
|---|---|---|---|
| 1 | 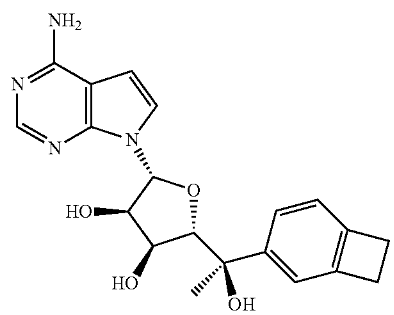 [SMILES: C[C@@](O)(c1ccc2c(c1)CC2)[C@H]1O[C@@H](n2ccc3c(N)ncnc32)[C@H](O)[C@@H]1O] | 382.42 | (2R,3R,4S,5S)-2-(4-amino-7H-pyrrolo[2,3-d]pyrimidin-7-yl)-5-((R)-1-(bicyclo[4.2.0]octa-1(6),2,4-trien-3-yl)-1-hydroxyethyl)tetrahydrofuran-3,4-diol |
| 2 | 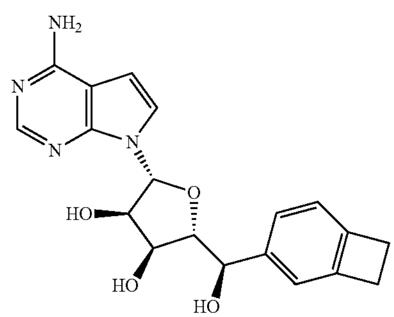 | 368.393 | (2R,3R,4S,5R)-2-(4-amino-7H-pyrrolo[2,3-d]pyrimidin-7-yl)-5-((R)-bicyclo[4.2.0]octa-1(6),2,4-trien-3-yl(hydroxy)methyl)tetrahydrofuran-3,4-diol |
| 3 | 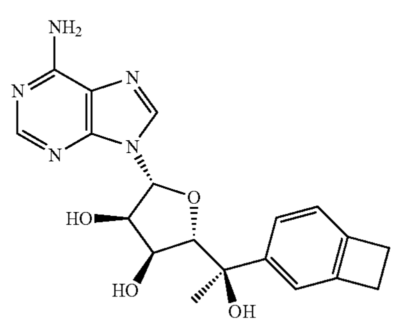 [SMILES: C[C@@](O)(c1ccc2c(c1)CC2)[C@H]1O[C@@H](n2cnc3c(N)ncnc32)[C@H](O)[C@@H]1O] | 383.408 | (2R,3R,4S,5S)-2-(6-amino-9H-purin-9-yl)-5-((R)-1-(bicyclo[4.2.0]octa-1(6),2,4-trien-3-yl)-1-hydroxyethyl)tetrahydrofuran-3,4-diol |
| 4 | 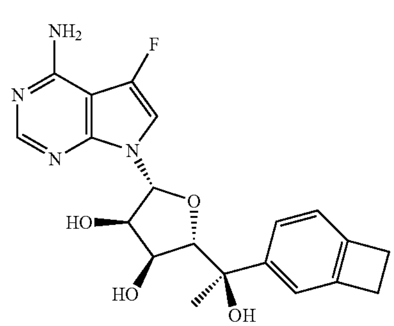 [SMILES: C[C@@](O)(c1ccc2c(c1)CC2)[C@H]1O[C@@H](n2cc(F)c3c(N)ncnc32)[C@H](O)[C@@H]1O] | 400.410403 | (2R,3R,4S,5S)-2-(4-amino-5-fluoro-7H-pyrrolo[2,3-d]pyrimidin-7-yl)-5-((R)-1-(bicyclo[4.2.0]octa-1(6),2,4-trien-3-yl)-1-hydroxyethyl)tetrahydrofuran-3,4-diol |

TABLE A-continued

| Example No. | Structure | MW | Chemical Name |
|---|---|---|---|
| 5 | 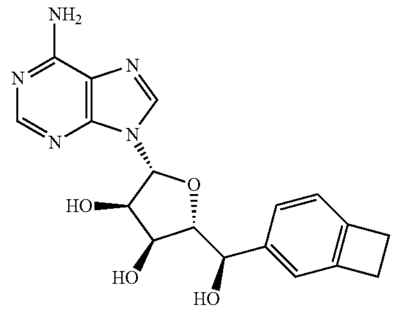 | 369.381 | (2R,3R,4S,5R)-2-(6-amino-9H-purin-9-yl)-5-((R)-bicyclo[4.2.0]octa-1(6),2,4-trien-3-yl(hydroxy)methyl)tetrahydrofuran-3,4-diol |
| 6 | 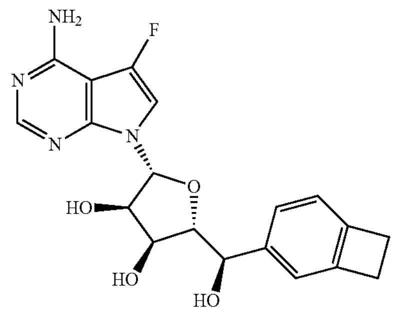 [SMILES: Nc1ncnc2c1c(F)cn2[C@@H]1O[C@H]([C@H](O)c2ccc3c(c2)CC3)[C@@H](O)[C@H]1O] | 386.383403 | (2R,3R,4S,5R)-2-(4-amino-5-fluoro-7H-pyrrolo[2,3-d]pyrimidin-7-yl)-5-((R)-bicyclo[4.2.0]octa-1(6),2,4-trien-3-yl(hydroxy)methyl)tetrahydrofuran-3,4-diol |
| 7 | 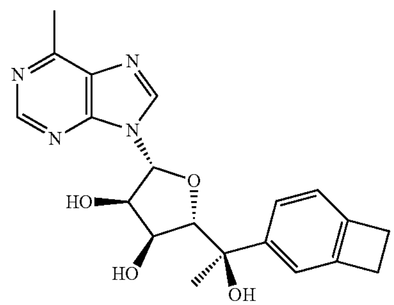 [SMILES: Cc1ncnc2c1ncn2[C@@H]1O[C@H]([C@](C)(O)c2ccc3c(c2)CC3)[C@@H](O)[C@H]1O] | 382.42 | (2S,3S,4R,5R)-2-((R)-1-(bicyclo[4.2.0]octa-1(6),2,4-trien-3-yl)-1-hydroxyethyl)-5-(6-methyl-9H-purin-9-yl)tetrahydrofuran-3,4-diol |
| 8 | 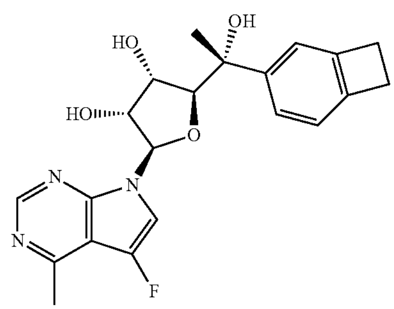 [SMILES: Cc1ncnc2c1c(F)cn2[C@@H]1O[C@H]([C@](C)(O)c2ccc3c(c2)CC3)[C@@H](O)[C@H]1O] | 399.422403 | (2S,3S,4R,5R)-2-((R)-1-(bicyclo[4.2.0]octa-1(6),2,4-trien-3-yl)-1-hydroxyethyl)-5-(5-fluoro-4-methyl-7H-pyrrolo[2,3-d]pyrimidin-7-yl)tetrahydrofuran-3,4-diol |
| 9 | 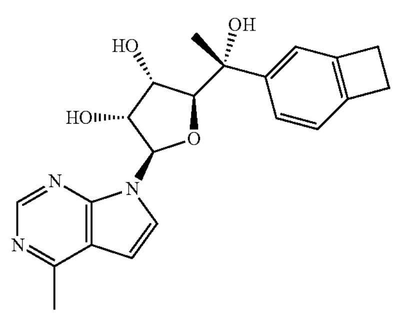 [SMILES: Cc1ncnc2c1ccn2[C@@H]1O[C@H]([C@](C)(O)c2ccc3c(c2)CC3)[C@@H](O)[C@H]1O] | 381.432 | (2S,3S,4R,5R)-2-((R)-1-(bicyclo[4.2.0]octa-1(6),2,4-trien-3-yl)-1-hydroxyethyl)-5-(4-methyl-7H-pyrrolo[2,3-d]pyrimidin-7-yl)tetrahydrofuran-3,4-diol |

TABLE A-continued

| Example No. | Structure | MW | Chemical Name |
|---|---|---|---|
| 10 | 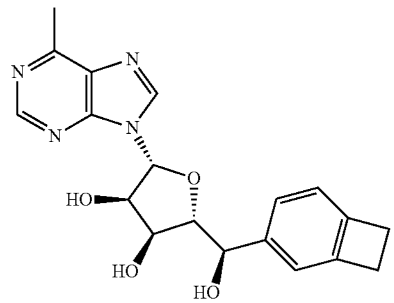 [SMILES: Cc1ncnc2c1ncn2[C@@H]1O[C@H]([C@H](O)c2ccc3c(c2)CC3)[C@@H](O)[C@H]1O] | 368.393 | (2R,3S,4R,5R)-2-((R)-bicyclo[4.2.0]octa-1(6),2,4-trien-3-yl(hydroxy)methyl)-5-(6-methyl-9H-purin-9-yl)tetrahydrofuran-3,4-diol |
| 11 | 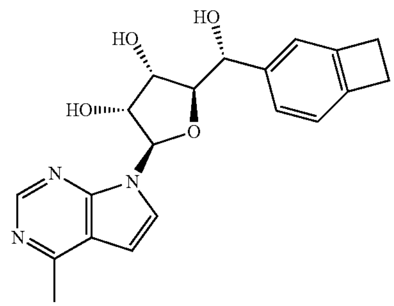 [SMILES: Cc1ncnc2c1ccn2[C@@H]1O[C@H]([C@H](O)c2ccc3c(c2)CC3)[C@@H](O)[C@H]1O] | 367.405 | (2R,3S,4R,5R)-2-((R)-bicyclo[4.2.0]octa-1(6),2,4-trien-3-yl(hydroxy)methyl)-5-(4-methyl-7H-pyrrolo[2,3-d]pyrimidin-7-yl)tetrahydrofuran-3,4-diol |
| 12 | 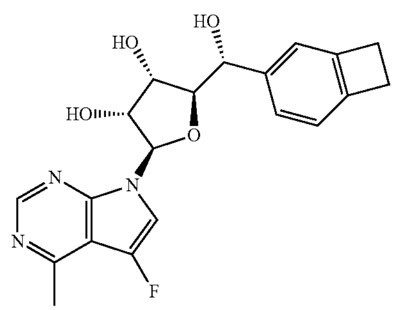 [SMILES: Cc1ncnc2c1c(F)cn2[C@@H]1O[C@H]([C@H](O)c2ccc3c(c2)CC3)[C@@H](O)[C@H]1O] | 385.395403 | (2R,3S,4R,5R)-2-((R)-bicyclo[4.2.0]octa-1(6),2,4-trien-3-yl(hydroxy)methyl)-5-(5-fluoro-4-methyl-7H-pyrrolo[2,3-d]pyrimidin-7-yl)tetrahydrofuran-3,4-diol |
| 13 | 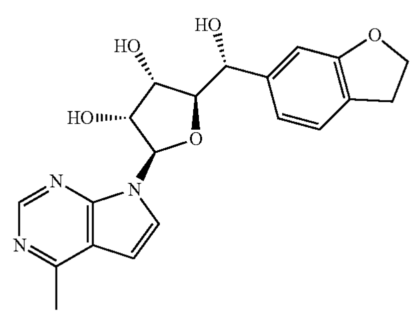 [SMILES: Cc1ncnc2c1ccn2[C@@H]1O[C@H]([C@H](O)c2ccc3c(c2)OCC3)[C@@H](O)[C@H]1O] | 383.404 | (2R,3S,4R,5R)-2-((R)-(2,3-dihydrobenzofuran-6-yl)(hydroxy)methyl)-5-(4-methyl-7H-pyrrolo[2,3-d]pyrimidin-7-yl)tetrahydrofuran-3,4-diol |
| 14 | 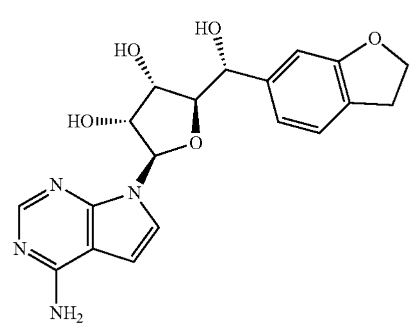 [SMILES: Nc1ncnc2c1ccn2[C@@H]1O[C@H]([C@H](O)c2ccc3c(c2)OCC3)[C@@H](O)[C@H]1O] | 384.392 | (2R,3R,4S,5R)-2-(4-amino-7H-pyrrolo[2,3-d]pyrimidin-7-yl)-5-((R)-(2,3-dihydrobenzofuran-6-yl)(hydroxy)methyl)tetrahydrofuran-3,4-diol |

TABLE A-continued

| Example No. | Structure | MW | Chemical Name |
|---|---|---|---|
| 15 | 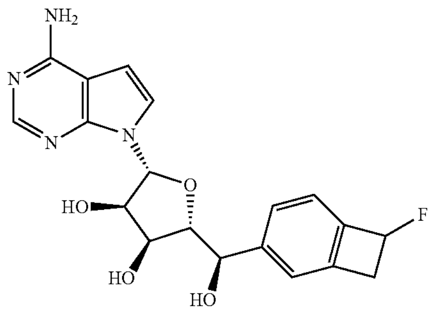 [SMILES: Nc1ncnc2c1ccn2[C@@H]1O[C@H]([C@H](O)c2ccc3c(c2)CC3F)[C@@H](O)[C@H]1O] | 386.383403 | (2R,3R,4S,5R)-2-(4-amino-7H-pyrrolo[2,3-d]pyrimidin-7-yl)-5-((1R)-(7-fluorobicyclo[4.2.0]octa-1(6),2,4-trien-3-yl)(hydroxy)methyl)tetrahydrofuran-3,4-diol |
| 16 | 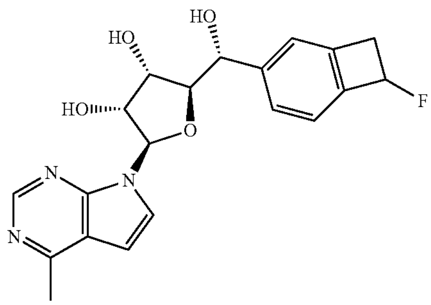 [SMILES: Cc1ncnc2c1ccn2[C@@H]1O[C@H]([C@H](O)c2ccc3c(c2)CC3F)[C@@H](O)[C@H]1O] | 385.395403 | (2R,3S,4R,5R)-2-((1R)-(7-fluorobicyclo[4.2.0]octa-1(6),2,4-trien-3-yl)(hydroxy)methyl)-5-(4-methyl-7H-pyrrolo[2,3-d]pyrimidin-7-yl)tetrahydrofuran-3,4-diol |
| 17 | 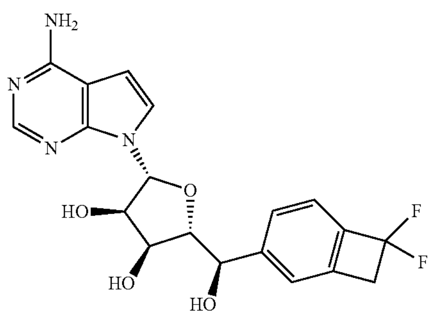 [SMILES: Nc1ncnc2c1ccn2[C@@H]1O[C@H]([C@H](O)c2ccc3c(c2)CC3(F)F)[C@@H](O)[C@H]1O] | 404.373806 | (2R,3R,4S,5R)-2-(4-amino-7H-pyrrolo[2,3-d]pyrimidin-7-yl)-5-((R)-(7,7-difluorobicyclo[4.2.0]octa-1(6),2,4-trien-3-yl)(hydroxy)methyl)tetrahydrofuran-3,4-diol |
| 18 | 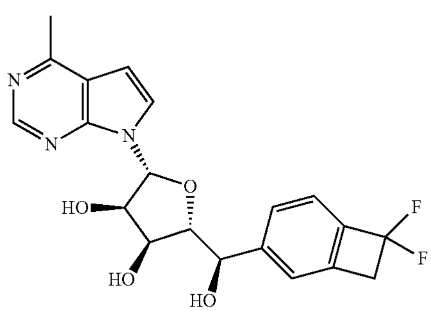 [SMILES: Cc1ncnc2c1ccn2[C@@H]1O[C@H]([C@H](O)c2ccc3c(c2)CC3(F)F)[C@@H](O)[C@H]1O] | 403.385806 | (2R,3S,4R,5R)-2-((R)-(7,7-difluorobicyclo[4.2.0]octa-1(6),2,4-trien-3-yl)(hydroxy)methyl)-5-(4-methyl-7H-pyrrolo[2,3-d]pyrimidin-7-yl)tetrahydrofuran-3,4-diol |
| 19 | 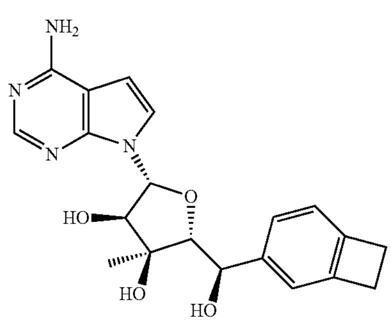 [SMILES: C[C@@]1(O)[C@@H]([C@H](O)c2ccc3c(c2)CC3)O[C@@H](n2ccc3c(N)ncnc32)[C@@H]1O] | 382.42 | (2R,3S,4R,5R)-5-(4-amino-7H-pyrrolo[2,3-d]pyrimidin-7-yl)-2-((R)-bicyclo[4.2.0]octa-1(6),2,4-trien-3-yl(hydroxy)methyl)-3-methyltetrahydrofuran-3,4-diol |

TABLE A-continued

| Example No. | Structure | MW | Chemical Name |
|---|---|---|---|
| 20 | 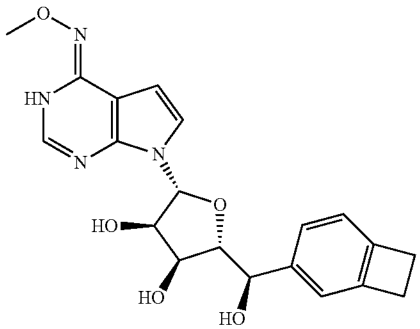 [SMILES: CO/N=c1\[nH]cnc2c1ccn2[C@@H]1O[C@H]([C@H](O)c2ccc3c(c2)CC3)[C@@H](O)[C@H]1O] | 398.419 | 7-((2R,3R,4S,5R)-5-((R)-bicyclo[4.2.0]octa-1(6),2,4-trien-3-yl(hydroxy)methyl)-3,4-dihydroxytetrahydrofuran-2-yl)-3,7-dihydro-4H-pyrrolo[2,3-d]pyrimidin-4-one O-methyl oxime |
| 21 | 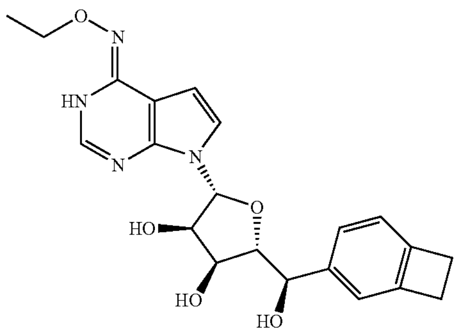 [SMILES: CCO/N=c1\[nH]cnc2c1ccn2[C@@H]1O[C@H]([C@H](O)c2ccc3c(c2)CC3)[C@@H](O)[C@H]1O] | 412.446 | 7-((2R,3R,4S,5R)-5-((R)-bicyclo[4.2.0]octa-1(6),2,4-trien-3-yl(hydroxy)methyl)-3,4-dihydroxytetrahydrofuran-2-yl)-3,7-dihydro-4H-pyrrolo[2,3-d]pyrimidin-4-one O-ethyl oxime |
| 22 | 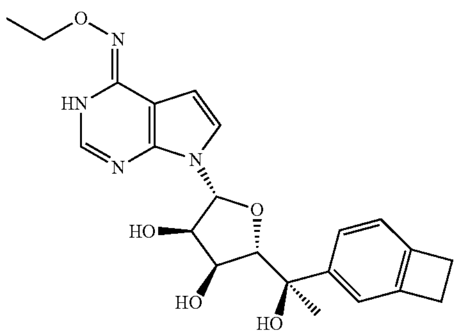 [SMILES: CCO/N=c1\[nH]cnc2c1ccn2[C@@H]1O[C@H]([C@](C)(O)c2ccc3c(c2)CC3)[C@@H](O)[C@H]1O] | 426.473 | 7-((2R,3R,4S,5S)-5-((R)-1-(bicyclo[4.2.0]octa-1(6),2,4-trien-3-yl)-1-hydroxyethyl)-3,4-dihydroxytetrahydrofuran-2-yl)-3,7-dihydro-4H-pyrrolo[2,3-d]pyrimidin-4-one O-ethyl oxime |
| 23 | 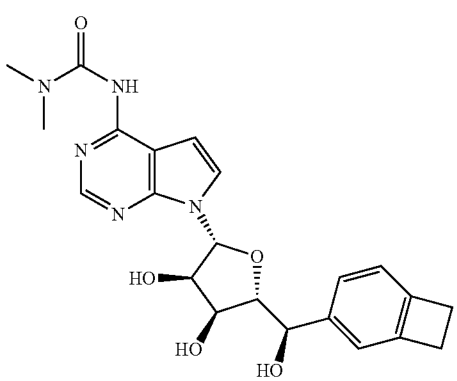 [SMILES: CN(C)C(=O)Nc1ncnc2c1ccn2[C@@H]1O[C@H]([C@H](O)c2ccc3c(c2)CC3)[C@@H](O)[C@H]1O] | 439.472 | 3-(7-((2R,3R,4S,5R)-5-((R)-bicyclo[4.2.0]octa-1(6),2,4-trien-3-yl(hydroxy)methyl)-3,4-dihydroxytetrahydrofuran-2-yl)-7H-pyrrolo[2,3-d]pyrimidin-4-yl)-1,1-dimethylurea |

TABLE A-continued

| Example No. | Structure | MW | Chemical Name |
|---|---|---|---|
| 24 | 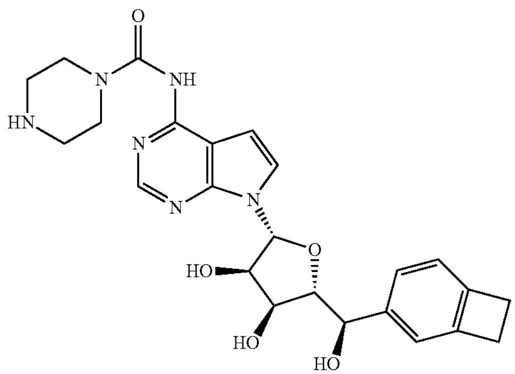 | 480.525 | N-(7-((2R,3R,4S,5R)-5-((R)-bicyclo[4.2.0]octa-1(6),2,4-trien-3-yl(hydroxy)methyl)-3,4-dihydroxytetrahydrofuran-2-yl)-7H-pyrrolo[2,3-d]pyrimidin-4-yl)piperazine-1-carboxamide |
| 25 | 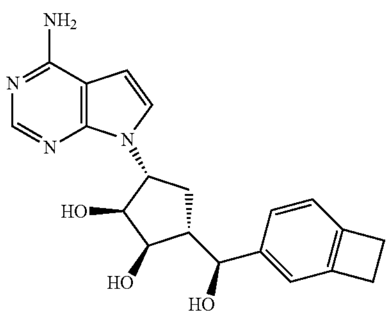 [SMILES: Nc1ncnc2c1ccn2[C@@H]1C[C@H]([C@H](O)c2ccc3c(c2)CC3)[C@@H](O)[C@H]1O] | 366.421 | (1R,2S,3R,5R)-3-(4-amino-7H-pyrrolo[2,3-d]pyrimidin-7-yl)-5-((S)-bicyclo[4.2.0]octa-1(6),2,4-trien-3-yl(hydroxy)methyl)cyclopentane-1,2-diol |
| 26 | 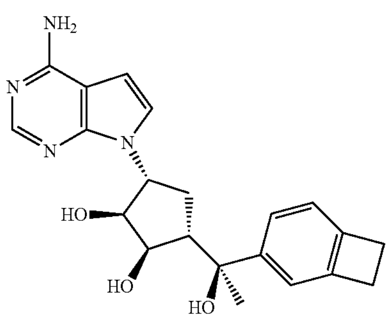 [SMILES: C[C@@](O)(c1ccc2c(c1)CC2)[C@H]1C[C@@H](n2ccc3c(N)ncnc32)[C@H](O)[C@@H]1O] | 380.448 | (1R,2S,3R,5S)-3-(4-amino-7H-pyrrolo[2,3-d]pyrimidin-7-yl)-5-((S)-1-(bicyclo[4.2.0]octa-1(6),2,4-trien-3-yl)-1-hydroxyethyl)cyclopentane-1,2-diol |
| 27 | 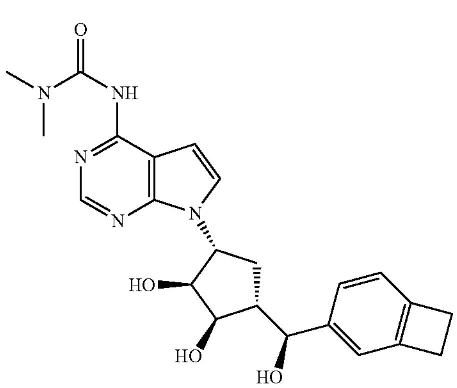 | 437.5 | 3-(7-((1R,2S,3R,4R)-4-((S)-bicyclo[4.2.0]octa-1(6),2,4-trien-3-yl(hydroxy)methyl)-2,3-dihydroxycyclopentyl)-7H-pyrrolo[2,3-d]pyrimidin-4-yl)-1,1-dimethylurea |

TABLE A-continued

| Example No. | Structure | MW | Chemical Name |
|---|---|---|---|
| 28 | 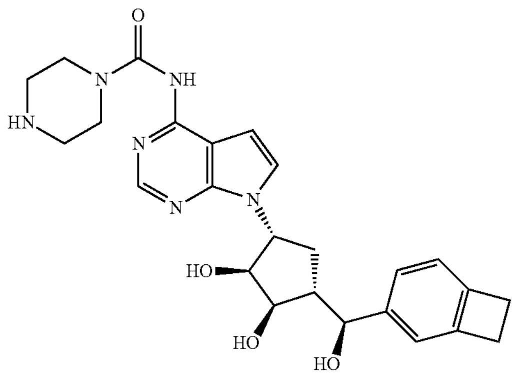 [SMILES: O=C(Nc1ncnc2c1ccn2[C@@H]1C[C@H]([C@H](O)c2ccc3c(c2)CC3)[C@@H](O)[C@H]1O)N1CCNCC1] | 478.553 | N-(7-((1R,2S,3R,4R)-4-((S)-bicyclo[4.2.0]octa-1(6),2,4-trien-3-yl(hydroxy)methyl)-2,3-dihydroxycyclopentyl)-7H-pyrrolo[2,3-d]pyrimidin-4-yl)piperazine-1-carboxamide |
| 29 | 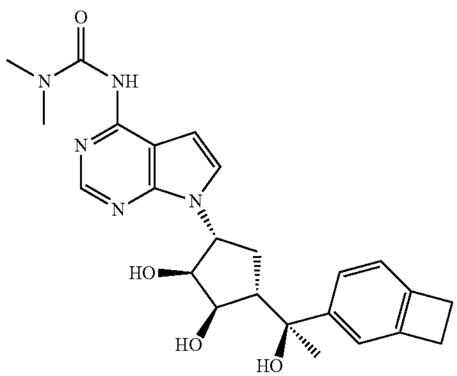 [SMILES: CN(C)C(=O)Nc1ncnc2c1ccn2[C@@H]1C[C@H]([C@](C)(O)c2ccc3c(c2)CC3)[C@@H](O)[C@H]1O] | 451.527 | 3-(7-((1R,2S,3R,4S)-4-((S)-1-(bicyclo[4.2.0]octa-1(6),2,4-trien-3-yl)-1-hydroxyethyl)-2,3-dihydroxycyclopentyl)-7H-pyrrolo[2,3-d]pyrimidin-4-yl)-1,1-dimethylurea |
| 30 | 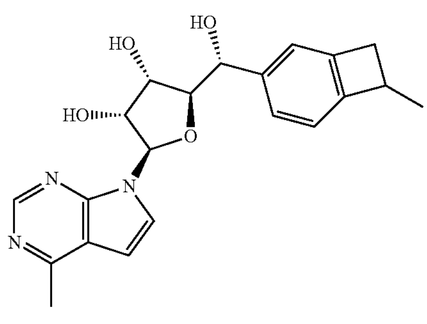 [SMILES: Cc1ncnc2c1ccn2[C@@H]1O[C@H]([C@H](O)c2ccc3c(c2)CC3C)[C@@H](O)[C@H]1O] | 381.43 | (2R,3S,4R,5R)-2-((1R)-hydroxy(7-methylbicyclo[4.2.0]octa-1(6),2,4-trien-3-yl)methyl)-5-(4-methyl-7H-pyrrolo[2,3-d]pyrimidin-7-yl)tetrahydrofuran-3,4-diol |
| 31 | 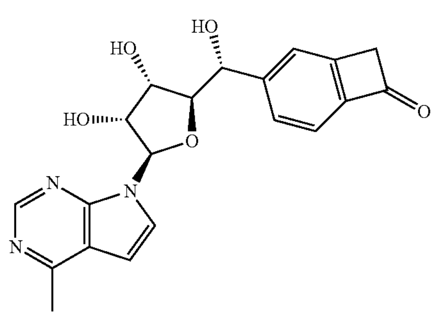 [SMILES: Cc1ncnc2c1ccn2[C@@H]1O[C@H]([C@H](O)c2ccc3c(c2)CC3=O)[C@@H](O)[C@H]1O] | 381.39 | 3-((R)-((2R,3S,4R,5R)-3,4-dihydroxy-5-(4-methyl-7H-pyrrolo[2,3-d]pyrimidin-7-yl)tetrahydrofuran-2-yl)(hydroxy)methyl)bicyclo[4.2.0]octa-1(6),2,4-trien-7-one |

TABLE A-continued

| Example No. | Structure | MW | Chemical Name |
|---|---|---|---|
| 32 | 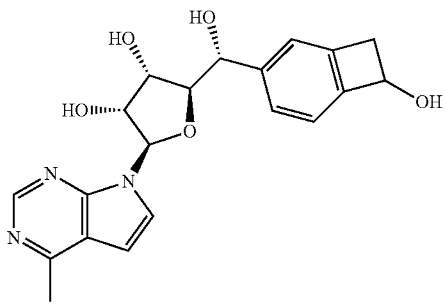 [SMILES: Cc1ncnc2c1ccn2[C@@H]1O[C@H]([C@H](O)c2ccc3c(c2)CC3O)[C@@H](O)[C@H]1O] | 383.40 | (2R,3S,4R,5R)-2-((1R)-hydroxy(7-hydroxybicyclo[4.2.0]octa-1(6),2,4-trien-3-yl)methyl)-5-(4-methyl-7H-pyrrolo[2,3-d]pyrimidin-7-yl)tetrahydrofuran-3,4-diol |
| 33 | 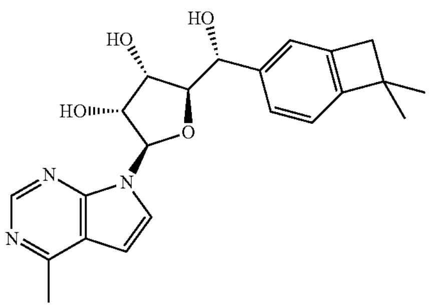 [SMILES: Cc1ncnc2c1ccn2[C@@H]1O[C@H]([C@H](O)c2ccc3c(c2)CC3(C)C)[C@@H](O)[C@H]1O] | 395.46 | (2R,3S,4R,5R)-2-((R)-(7,7-dimethylbicyclo[4.2.0]octa-1(6),2,4-trien-3-yl)(hydroxy)methyl)-5-(4-methyl-7H-pyrrolo[2,3-d]pyrimidin-7-yl)tetrahydrofuran-3,4-diol |
| 34 | 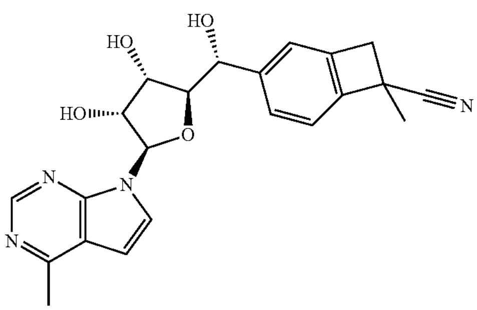 [SMILES: Cc1ncnc2c1ccn2[C@@H]1O[C@H]([C@H](O)c2ccc3c(c2)CC3(C)C#N)[C@@H](O)[C@H]1O] | 406.44 | 3-((R)-((2R,3S,4R,5R)-3,4-dihydroxy-5-(4-methyl-7H-pyrrolo[2,3-d]pyrimidin-7-yl)tetrahydrofuran-2-yl)(hydroxy)methyl)-7-methylbicyclo[4.2.0]octa-1(6),2,4-triene-7-carbonitrile |
| 35 | 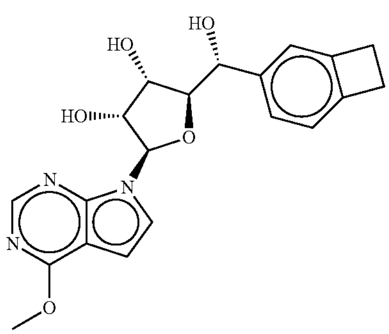 | 383.4 | (2R,3S,4R,5R)-2-[(R)-4-bicyclo[4.2.0]octa-1,3,5-trienyl(hydroxy)methyl]-5-(4-methoxypyrrolo[2,3-d]pyrimidin-7-yl)tetrahydrofuran-3,4-diol |
| 36 | 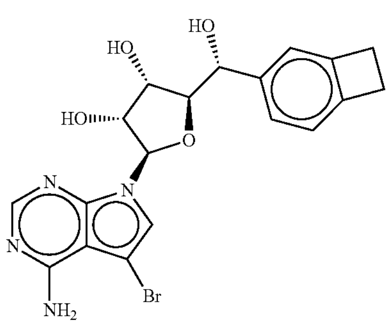 | 447.28 | (2R,3R,4S,5R)-2-(4-amino-5-bromo-7H-pyrrolo[2,3-d]pyrimidin-7-yl)-5-((R)-bicyclo[4.2.0]octa-1,3,5-trien-3-yl(hydroxy)methyl)tetrahydrofuran-3,4-diol |

TABLE A-continued

| Example No. | Structure | MW | Chemical Name |
|---|---|---|---|
| 37 | 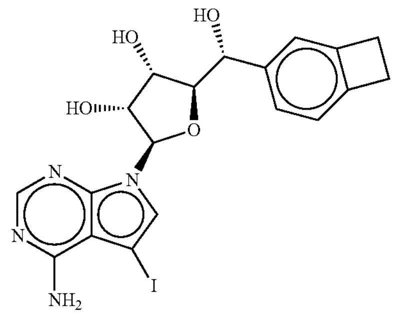 | 494.28 | (2R,3R,4S,5R)-2-(4-amino-5-iodo-7H-pyrrolo[2,3-d]pyrimidin-7-yl)-5-((R)-bicyclo[4.2.0]octa-1(6),2,4-trien-3-yl(hydroxy)methyl)tetrahydrofuran-3,4-diol |
| 38 | 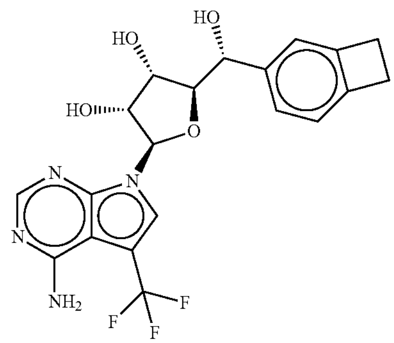 | 436.38 | (2R,3R,4S,5R)-2-(4-amino-5-(trifluoromethyl)-7H-pyrrolo[2,3-d]pyrimidin-7-yl)-5-((R)-bicyclo[4.2.0]octa-1(6),2,4-trien-3-yl(hydroxy)methyl)tetrahydrofuran-3,4-diol |
| 39 | 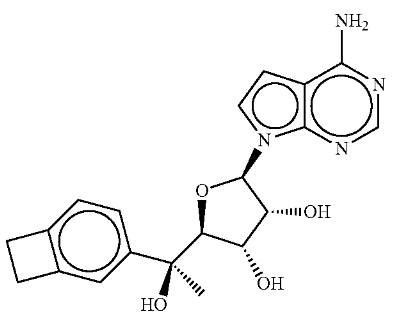 | 382.41 | (2R,3R,4S,5S)-2-(4-amino-7H-pyrrolo[2,3-d]pyrimidin-7-yl)-5-((S)-1-(bicyclo[4.2.0]octa-1(6),2,4-trien-3-yl)-1-hydroxyethyl)tetrahydrofuran-3,4-diol |
| 40 | 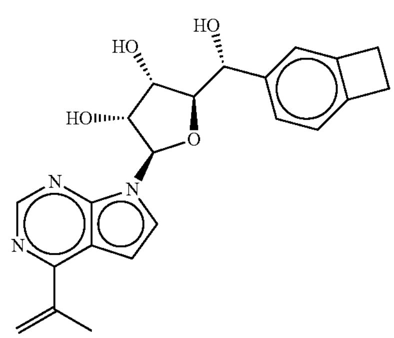 | 393.44 | (2R,3S,4R,5R)-2-((R)-bicyclo[4.2.0]octa-1(6),2,4-trien-3-yl(hydroxy)methyl)-5-(4-(prop-1-en-2-yl)-7H-pyrrolo[2,3-d]pyrimidin-7-yl)tetrahydrofuran-3,4-diol |

TABLE A-continued

| Example No. | Structure | MW | Chemical Name |
|---|---|---|---|
| 41 | 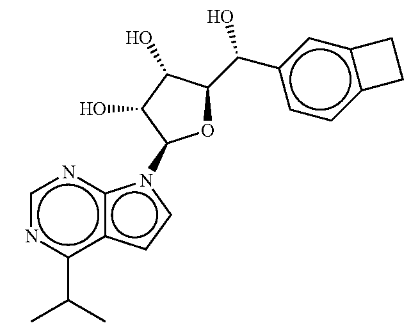 | 395.45 | (2R,3S,4R,5R)-2-((R)-bicyclo[4.2.0]octa-1(6),2,4-trien-3-yl(hydroxy)methyl)-5-(4-isopropyl-7H-pyrrolo[2,3-d]pyrimidin-7-yl)tetrahydrofuran-3,4-diol |
| 42 | 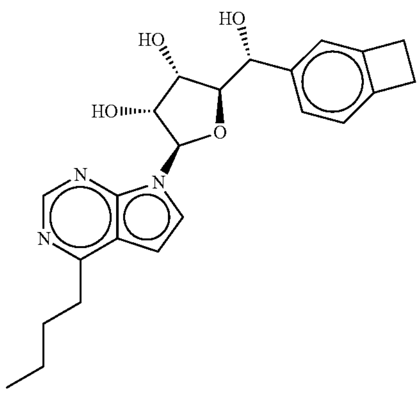 | 409.48 | (2R,3S,4R,5R)-2-((R)-bicyclo[4.2.0]octa-1,3,5-trien-3-yl(hydroxy)methyl)-5-(4-butyl-7H-pyrrolo[2,3-d]pyrimidin-7-yl)tetrahydrofuran-3,4-diol |
| 43 | 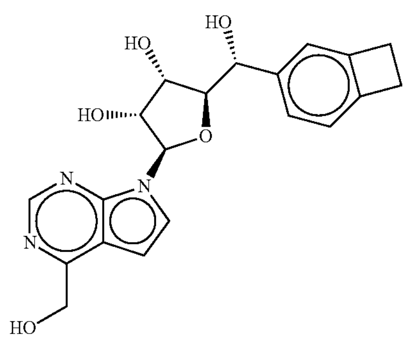 | 383.4 | (2R,3S,4R,5R)-2-((R)-bicyclo[4.2.0]octa-1,3,5-trien-3-yl(hydroxy)methyl)-5-(4-(hydroxymethyl)-7H-pyrrolo[2,3-d]pyrimidin-7-yl)tetrahydrofuran-3,4-diol |
| 44 | 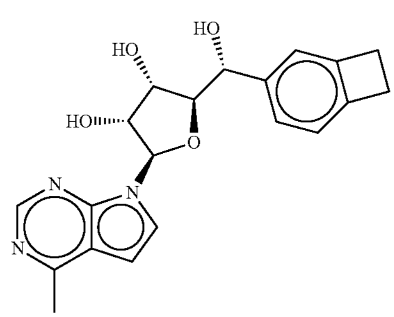 | 381.43 | (2R,3S,4R,5R)-2-((R)-(2,3-dihydro-1H-inden-5-yl)(hydroxy)methyl)-5-(4-methyl-7H-pyrrolo[2,3-d]pyrimidin-7-yl)tetrahydrofuran-3,4-diol |

TABLE A-continued

| Example No. | MW | Chemical Name |
|---|---|---|
| 45 | 382.41 | (2R,3R,4S,5R)-2-(4-amino-7H-pyrrolo[2,3-d]pyrimidin-7-yl)-5-((R)-(2,3-dihydro-1H-inden-5-yl)(hydroxy)methyl)tetrahydrofuran-3,4-diol |
| 46 | 379.41 | (2R,3S,4R,5R)-2-((R)-bicyclo[4.2.0]octa-1(6),2,4-trien-3-yl(hydroxy)methyl)-5-(4-vinyl-7H-pyrrolo[2,3-d]pyrimidin-7-yl)tetrahydrofuran-3,4-diol |
| 47 | 367.4 | (2R,3S,4R,5R)-2-((S)-bicyclo[4.2.0]octa-1,3,5-trien-3-yl(hydroxy)methyl)-5-(4-methyl-7H-pyrrolo[2,3-d]pyrimidin-7-yl)tetrahydrofuran-3,4-diol |
| 48 | 411.45 | (2R,3S,4R,5R)-2-((R)-bicyclo[4.2.0]octa-1(6),2,4-trien-3-yl(hydroxy)methyl)-5-(4-(2-methoxyethyl)-7H-pyrrolo[2,3-d]pyrimidin-7-yl)tetrahydrofuran-3,4-diol |

TABLE A-continued

| Example No. | Structure | MW | Chemical Name |
|---|---|---|---|
| 49 | 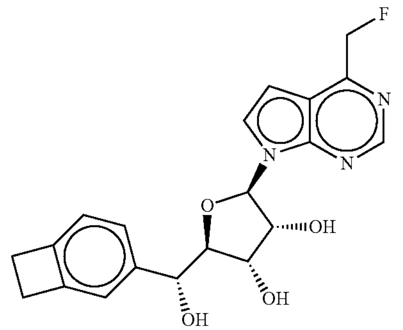 | 385.39 | (2R,3S,4R,5R)-2-((R)-bicyclo[4.2.0]octa-1(6),2,4-trien-3-yl(hydroxy)methyl)-5-(4-(fluoromethyl)-7H-pyrrolo[2,3-d]pyrimidin-7-yl)tetrahydrofuran-3,4-diol |
| 50 | 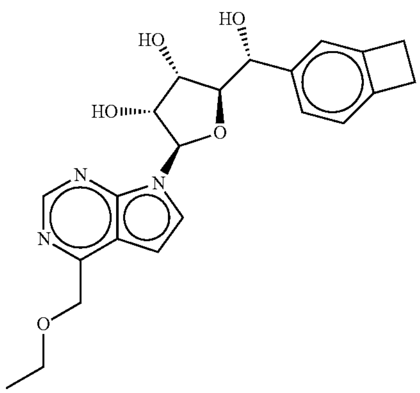 | 411.45 | (2R,3S,4R,5R)-2-((R)-bicyclo[4.2.0]octa-1(6),2,4-trien-3-yl(hydroxy)methyl)-5-(4-(ethoxymethyl)-7H-pyrrolo[2,3-d]pyrimidin-7-yl)tetrahydrofuran-3,4-diol |
| 51 | 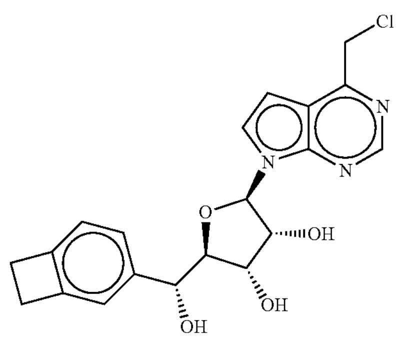 | 401.84 | (2R,3S,4R,5R)-2-((R)-bicyclo[4.2.0]octa-1(6),2,4-trien-3-yl(hydroxy)methyl)-5-(4-(chloromethyl)-7H-pyrrolo[2,3-d]pyrimidin-7-yl)tetrahydrofuran-3,4-diol |
| 52 | 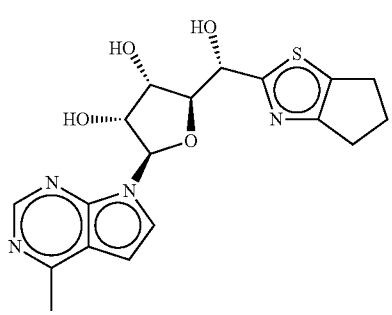 | 388.44 | (2S,3S,4R,5R)-2-((S)-(5,6-dihydro-4H-cyclopenta[d]thiazol-2-yl)(hydroxy)methyl)-5-(4-methyl-7H-pyrrolo[2,3-d]pyrimidin-7-yl)tetrahydrofuran-3,4-diol |

TABLE A-continued

| Example No. | Structure | MW | Chemical Name |
|---|---|---|---|
| 53 | 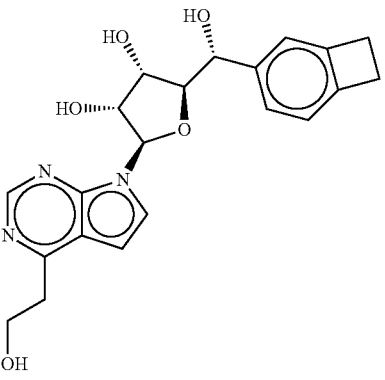 | 397.42 | (2R,3S,4R,5R)-2-((R)-bicyclo[4.2.0]octa-1,3,5-trien-3-yl(hydroxy)methyl)-5-(4-(2-hydroxyethyl)-7H-pyrrolo[2,3-d]pyrimidin-7-yl)tetrahydrofuran-3,4-diol |
| 54 | 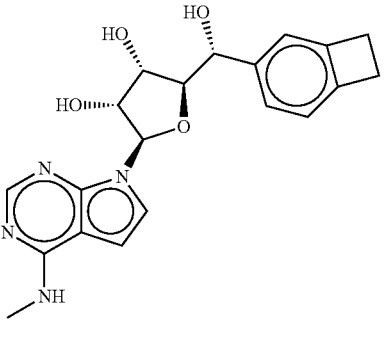 | 382.41 | (2R,3S,4R,5R)-2-((R)-bicyclo[4.2.0]octa-1(6),2,4-trien-3-yl(hydroxy)methyl)-5-(4-(methylamino)-7H-pyrrolo[2,3-d]pyrimidin-7-yl)tetrahydrofuran-3,4-diol |
| 55 | 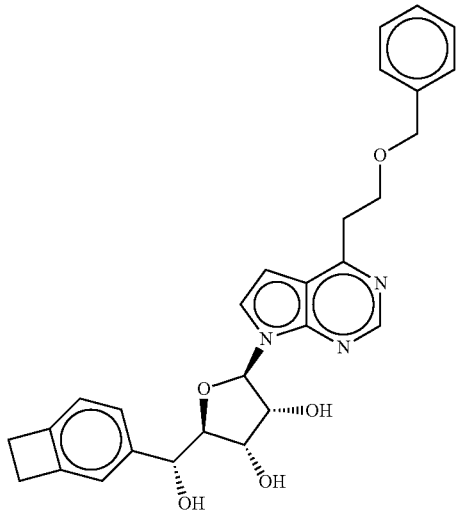 | 487.55 | (2R,3R,4S,5R)-2-(4-(2-(benzyloxy)ethyl)-7H-pyrrolo[2,3-d]pyrimidin-7-yl)-5-((R)-bicyclo[4.2.0]octa-1(6),2,4-trien-3-yl(hydroxy)methyl)tetrahydrofuran-3,4-diol |
| 56 | 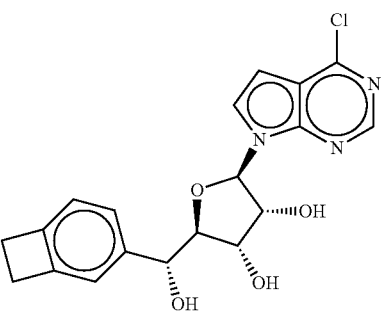 | 387.82 | (2R,3S,4R,5R)-2-((R)-bicyclo[4.2.0]octa-1(6),2,4-trien-3-yl(hydroxy)methyl)-5-(4-chloro-7H-pyrrolo[2,3-d]pyrimidin-7-yl)tetrahydrofuran-3,4-diol |

EXPERIMENTAL PROCEDURES

Examples

Example 1. (2R,3R,4S,5S)-2-(4-amino-7H-pyrrolo[2,3-d]pyrimidin-7-yl)-5-((R)-1-(bicyclo[4.2.0]octa-1,3,5-trien-3-yl)-1-hydroxyethyl)tetrahydrofuran-3,4-diol (1)

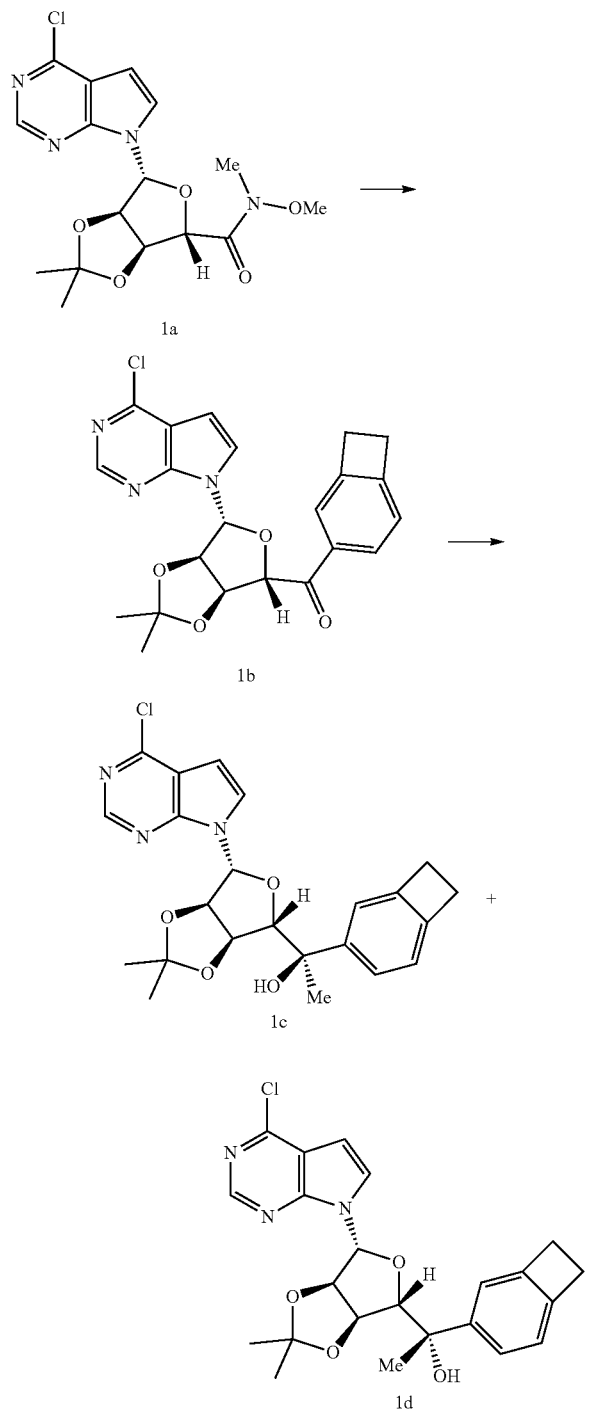

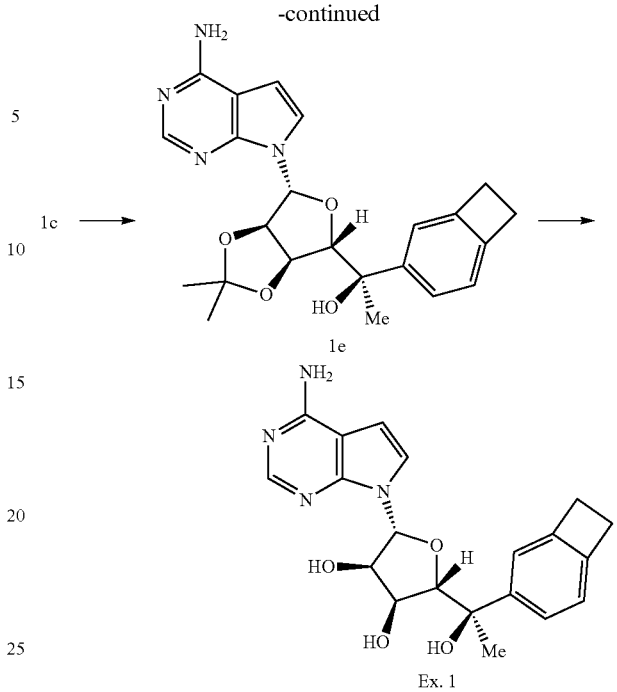

Step 1. Synthesis of bicyclo[4.2.0]octa-1,3,5-trien-3-yl((3aS,4S,6R,6aR)-6-(4-chloro-7H-pyrrolo[2,3-d]pyrimidin-7-yl)-2,2-dimethyltetrahydrofuro[3,4-d][1,3]dioxol-4-yl)methanone (1b)

A 50 mL RBF with septum containing Magnesium (208 mg, 8.56 mmol) was dried under high vacuum with a heat gun and cooled under Ar. The flask was charged with THF (3.4 mL), 4/10ths the portion of 4-bromobicyclo[4.2.0]octa-1(6),2,4-triene (1.01 mL, 8.11 mmol), and diisobutylaluminum hydride, 1 M in toluene (20 uL, 0.0200 mmol) at RT. Initiation of the magnesium was observed by self heating of the reaction solution after 1 minute of stirring. The reaction mixture was stirred for 10 additional min, diluted with THF (3 mL), then charged with the remaining 4-bromobicyclo[4.2.0]octa-1(6),2,4-triene in two portions over 10 min, and stirred at RT for 30 additional min (or until the reaction mixture returns to RT). A majority of the magnesium turnings were consumed by the Grignard reagent formation. A solution of 1a, (3aR,4R,6S,6aS)-4-(4-chloropyrrolo[2,3-d]pyrimidin-7-yl)-N-methoxy-N,2,2-trimethyl-3 a,4,6,6a-tetrahydrofuro[3,4-d][1,3]dioxole-6-carboxamide (2.21 g, 5.77 mmol) in THF (18 mL) was prepared in a heat-dried RBF. The ketone material was previously exhaustively dried under high vacuum with heat gun to remove a majority of the residual EtOAc solvent. The Grignard solution was transferred by cannula, dropwise over 2 min, and rinsed with THE (2 mL), to the ketone solution at 0° C. The solution was stirred at 0° C. for 5 min, then stirred at RT for 30 min. The reaction mixture was cooled to 0° C. in an ice-bath, quenched with EtOAc (1 mL), placed at RT, and stirred for 5 min. The reaction mixture was then neutralized with sat. NH$_4$Cl (10 mL), diluted with water (80 mL), and extracted with EtOAc (100 mL). The organic layer was separated, washed with sat. sodium potassium tartrate (10 mL), water (2×80 mL), brine (40 mL), dried over Na$_2$SO$_4$ and MgSO$_4$, filtered, and concentrated to a yellow foam. The crude mixture was purified by FCC (40 g SiO$_2$, 0→30% EtOAc in hexanes, wet-loaded in DCM+hexanes) to yield 1b [(3aR, 4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1(6),2,4-trienyl)methanone (2.32 g, 5.45 mmol, 94.4% yield) as a yellow foam. Rf=0.53 (1:2 EtOAc:hexanes); $^1$H NMR (600 MHz, Chloroform-d) δ 8.48 (s, 1H), 7.68 (dd, J=1.4, 7.7 Hz, 1H), 7.46 (s, 1H), 7.35 (d, J=3.7 Hz, 1H), 7.05 (dd, J=1.0, 7.6 Hz, 1H), 6.56 (d, J=3.7 Hz, 1H), 6.45 (d, J=1.3 Hz, 1H), 5.61 (dd, J=2.1, 6.1 Hz, 1H), 5.48 (d, J=2.1 Hz, 1H), 5.42 (dd, J=1.3, 6.0 Hz, 1H), 3.21-3.14 (m, 4H), 1.70 (s, 3H), 1.44 (s, 3H); LRMS (ESI) m/z calcd for [M+H]$^+$ $C_{22}H_{21}ClN_3O_4$: 426.12/426.12. Found: 426.0/428.0.

Step 2. Synthesis of (R)-1-(bicyclo[4.2.0]octa-1,3,5-trien-3-yl)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)ethan-1-ol (1c and 1d)

A 25 mL RBF with septum containing 1b, [(3aR,4R,6S, 6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanone (442.5 mg, 1.04 mmol) was evacuated and backfilled with Ar (×3). The flask was charged with THF (6 mL), placed in a RT water bath, and charged with methyl magnesium bromide, 3.2 M in MeTHF (0.81 mL, 2.6 mmol), dropwise over 10 min. The reaction was stirred at RT for 1 h. Reaction complete by TLC and LCMS, showing a ~5:1 ratio of diastereomers by LCMS. The reaction mixture was carefully quenched with sat. NH$_4$Cl (2 mL) (caution: gas evolution), diluted with water (40 mL), extracted with EtOAc (40 mL), washed with water (40 mL), brine (20 mL), and dried over Na$_2$SO$_4$. The mixture was filtered, concentrated under reduced pressure, and purified by FCC (40 g SiO$_2$, 0→30% EtOAc in hexanes, wet-loaded in DCM) to yield 1c (1R)-1-[(3aR,4R,6S,6aR)-4-(4-chloropyrrolo[2,3-d]pyrimidin-7-yl)-2,2-dimethyl-3a, 4,6,6a-tetrahydrofuro[3,4-d][1,3]dioxol-6-yl]-1-(4-bicyclo[4.2.0]octa-1,3,5-trienyl)ethanol (349.7 mg, 0.7913 mmol, 76.2% yield) as a white foam and 1d (1S)-1-[(3aR,4R,6S, 6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(4-bicyclo[4.2.0]octa-1,3,5-trienyl)ethanol (46.4 mg, 0.105 mmol, 10.1% yield) as clear pink glass.

(1c) Rf=0.58 (1:2 EtOAc:hexanes); $^1$H NMR (400 MHz, Chloroform-d) δ 8.74 (s, 1H), 7.41 (dd, J=1.5, 7.7 Hz, 1H), 7.35 (d, J=3.7 Hz, 1H), 7.27 (s, 1H), 7.09 (d, J=7.7 Hz, 1H), 6.66 (d, J=3.7 Hz, 1H), 6.38 (bs, 1H), 5.85 (d, J=5.5 Hz, 1H), 5.17 (t, J=5.7 Hz, 1H), 4.72 (dd, J=1.2, 6.0 Hz, 1H), 4.64 (d, J=1.2 Hz, 1H), 3.23-3.16 (m, 4H), 1.58 (s, 3H), 1.51 (s, 3H), 1.21 (s, 3H); LRMS (ESI) m/z calcd for [M+H]$^+$ $C_{23}H_{25}ClN_3O_4$: 442.15/444.15. Found: 442.0/444.0.

(1d) Rf=0.48 (1:2 EtOAc:hexanes); $^1$H NMR (400 MHz, Chloroform-d) δ 8.73 (dd, J=2.4, 6.8 Hz, 1H), 7.29-7.25 (m, 1H), 7.22 (bs, 1H), 7.17 (d, J=3.7 Hz, 1H), 7.13 (s, 1H), 6.95 (d, J=7.7 Hz, 1H), 6.54 (d, J=3.6 Hz, 1H), 5.75 (d, J=4.6 Hz, 1H), 5.31 (dd, J=2.4, 6.5 Hz, 1H), 5.14 (d, J=4.6, 6.7 Hz, 1H), 4.71 (d, J=2.4 Hz, 1H), 3.12-3.03 (m, 4H), 1.66 (s, 3H), 1.61 (s, 3H), 1.41 (s, 3H); LRMS (ESI) m/z calcd for [M+H]$^+$ $C_{23}H_{25}ClN_3O_4$: 442.15/444.15. Found: 442.1/444.1.

Step 3. Synthesis of (R)-1-((3aR,4S,6R,6aR)-6-(4-amino-7H-pyrrolo[2,3-d]pyrimidin-7-yl)-2,2-dimethyltetrahydrofuro[3,4-d][1,3]dioxol-4-yl)-1-(bicyclo[4.2.0]octa-1,3,5-trien-3-yl)ethan-1-ol (1e)

A 5 mL microwave vial with septum containing 1c (1R)-1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(4-bicyclo[4.2.0]octa-1,3,5-trienyl)ethanol (132.5 mg, 0.300 mmol) was evacuated and backfilled with Ar (×3). The vial was charged with 1,4-Dioxane (1 mL) and ammonium hydroxide (2 mL, 30 mmol), and briefly heated until a homogeneous solution formed. The reaction mixture was then microwaved at 120° C. for 12 h. The mixture was concentrated under reduced pressure to remove all volatiles and used crude in the next reaction. LRMS (ESI) m/z calcd for [M+H]$^+$ $C_{23}H_{27}N_4O_4$: 423.20. Found: 423.1.

Step 4. Synthesis of (2R,3R,4S,5S)-2-(4-amino-7H-pyrrolo[2,3-d]pyrimidin-7-yl)-5-((R)-1-(bicyclo[4.2.0]octa-1,3,5-trien-3-yl)-1-hydroxyethyl)tetrahydrofuran-3,4-diol (Ex. 1)

A 100 mL RBF with septum containing a solution of crude 1e ((1R)-1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-(4-bicyclo[4.2.0]octa-1,3,5-trienyl)ethanol) (0.30 mmol) in Methanol (2 mL) was purged with Ar for 1 min. The reaction mixture was charged with Hydrochloric acid, 1 M (2. mL, 2 mmol) and stirred at RT for 2 h. The reaction mixture was then charged with Hydrochloric acid, 1 M (2. mL, 2 mmol) and stirred at RT for 2 h. The mixture was concentrated under reduced pressure and purified by FCC (30 g C18, 5→40% MeCN in H$_2$O, wet-loaded in DMSO). One fraction containing product was lyophilized to yield the TFA salt of Ex. 1, (2R,3R,4S,5S)-2-(4-aminopyrrolo[2,3-d]pyrimidin-7-yl)-5-[(1R)-1-(4-bicyclo[4.2.0]octa-1,3,5-trienyl)-1-hydroxy-ethyl]tetrahydrofuran-3,4-diol; 2,2,2-trifluoroacetic acid (34.4 mg, 93.8% purity, 0.0650 mmol, 21.7% yield over two steps), as a fluffy white solid. Another fraction containing product was concentrated under reduced pressure, diluted with MeOH, neutralized with Amberlite IRA-67 resin, filtered through a cellulose acetate frit, and concentrated under reduced pressure and heat (50° C.) to yield Ex. 1 (2R,3R,4S,5S)-2-(4-aminopyrrolo[2,3-d]pyrimidin-7-yl)-5-[(1R)-1-(4-bicyclo[4.2.0]octa-1,3,5-trienyl)-1-hydroxy-ethyl]tetrahydrofuran-3,4-diol (51.2 mg, 95.5% purity, 0.128 mmol, 42.6% yield over two steps) as a beige powder.

(TFA salt of Ex. 1) $^1$H NMR (400 MHz, DMSO-d$_6$) δ 9.23-8.00 (m, 3H), 8.36 (s, 1H), 7.75 (d, J=3.6 Hz, 1H), 7.37 (dd, J=1.5, 7.8 Hz, 1H), 7.24 (s, 1H), 7.05 (d, J=7.7 Hz, 1H), 6.94 (d, J=3.4 Hz, 1H), 6.05 (d, J=8.0 Hz, 1H), 5.86 (bs, 1H), 5.19 (bs, 1H), 4.87 (bs, 1H), 4.47 (dd, J=5.0, 7.9 Hz, 1H), 4.09 (s, 1H), 3.73 (d, J=5.0 Hz, 1H), 3.12 (s, 4H), 1.41 (s, 3H); LRMS (ESI) m/z calcd for [M+H]$^+$ $C_{20}H_{23}N_4O_4$: 383.17. Found: 383.1.

(Ex. 1) $^1$H NMR (400 MHz, DMSO-d$_6$) δ 8.09 (s, 1H), 7.39 (dd, J=1.4, 7.8 Hz, 1H), 7.36 (d, J=3.6 Hz, 1H), 7.29 (bs, 2H), 7.25 (s, 1H), 7.04 (d, J=7.7 Hz, 1H), 6.86 (bs, 1H), 6.61 (d, J=3.6 Hz, 1H), 5.81 (d, J=8.1 Hz, 1H), 5.12 (d, J=7.2 Hz, 1H), 4.72 (d, J=3.5 Hz, 1H), 4.65 (td, J=5.0, 7.6 Hz, 1H), 4.11 (s, 1H), 3.68 (dd, J=3.2, 5.0 Hz, 1H), 3.12 (s, 4H), 1.37 (s, 3H); LRMS (ESI) m/z calcd for [M+H]$^+$$C_{20}H_{23}N_4O_4$: 383.17. Found: 383.1.

Example 2. (2R,3R,4S,5R)-2-(4-amino-7H-pyrrolo[2,3-d]pyrimidin-7-yl)-5-((R)-bicyclo[4.2.0]octa-1(6),2,4-trien-3-yl(hydroxy)methyl)tetrahydrofuran-3,4-diol (2)

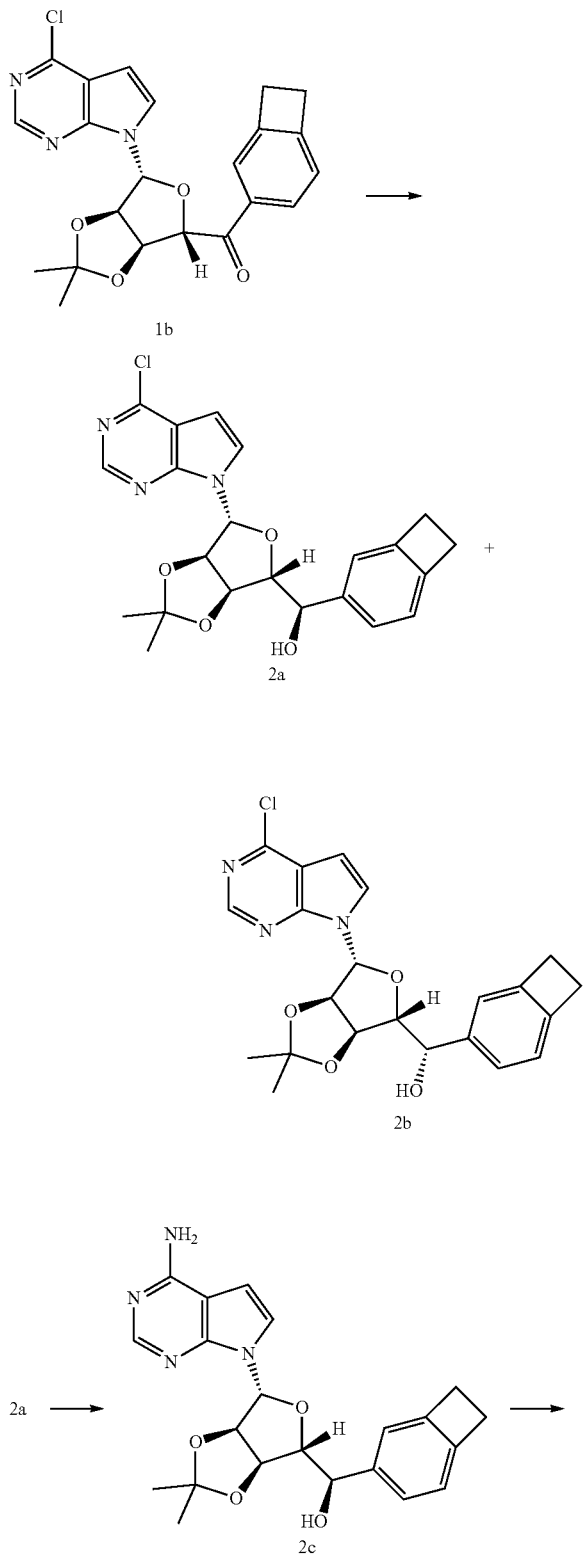

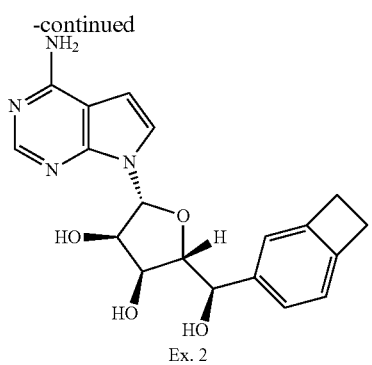

Ex. 2

Step 1. Synthesis of (R)-bicyclo[4.2.0]octa-1,3,5-trien-3-yl((3aR,4R,6R,6aR)-6-(4-chloro-7H-pyrrolo[2,3-d]pyrimidin-7-yl)-2,2-dimethyltetrahydrofuro[3,4-d][1,3]dioxol-4-yl)methanol (2a) and (R)-bicyclo[4.2.0]octa-1,3,5-trien-3-yl((3aR,4R,6R,6aR)-6-(4-chloro-7H-pyrrolo[2,3-d]pyrimidin-7-yl)-2,2-dimethyltetrahydrofuro[3,4-d][1,3]dioxol-4-yl)methanol (2b)

A 100 mL RBF with septum containing a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanone (1200. mg, 2.82 mmol) in toluene (25 mL) under argon was cooled to −76° C. in a acetone/dry-ice bath. Diisobutylaluminum hydride; DIBAL, 1 M in toluene (5.4 mL, 5.4 mmol) was added dropwise over 4 min. The reaction mixture was stirred at −76° C. for 1 h and TLC (hexane/EtOAc 70:30) showed completion. The reaction was placed in a 0° C. ice bath and quenched with the careful addition of water (0.04× 5.4 mL), 15% NaOH (0.04×5.4 mL) and water (0.1×5.4 mL) of water and stirred for 15 min. The reaction mixture was charged with $Na_2SO_4$, stirred for another 5 min and filtered through a pad of celite. The crude was concentrated under reduced pressure and purified on a 40 g silica gel column chromatography using hexane/EtOAc to give (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (2a) (800 mg, 1.87 mmol, 66.4% yield) and (S)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (2b) (370 mg, 0.86 mmol, 30.7% yield) as white solids.

For compound 2a $^1$H NMR (400 MHz, Chloroform-d) δ 8.71 (s, 1H), 7.35 (d, J=3.7 Hz, 1H), 7.30 (dd, J=1.3, 7.8 Hz, 1H), 7.18 (d, J=1.2 Hz, 1H), 7.09-7.05 (m, 1H), 6.65 (d, J=3.7 Hz, 1H), 5.86 (d, J=5.2 Hz, 1H), 5.26 (t, J=5.6 Hz, 1H), 5.08 (d, J=2.0 Hz, 1H), 5.02 (dd, J=1.4, 6.1 Hz, 1H), 4.59 (t, J=1.8 Hz, 1H), 3.18 (s, 4H), 1.58 (s, 3H), 1.29 (s, 3H).

Step 2. Synthesis of (R)-((3aR,4R,6R,6aR)-6-(4-amino-7H-pyrrolo[2,3-d]pyrimidin-7-yl)-2,2-dimethyltetrahydrofuro[3,4-d][1,3]dioxol-4-yl)(bicyclo[4.2.0]octa-1,3,5-trien-3-yl)methanol (2c)

To (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (600. mg, 1.4 mmol) in Methanol (5 mL) was added the ammonium hydroxide (1. mL, 2.8 mmol). The reaction was heated at 120° C. for 16 h. The reaction mixture was concentrated and the crude was extracted with ethyl acetate, washed with water, brine, dried over sodium sulfate, filtered and concentrated. The crude was purified by silica gel chromatography using 0-30% EtOAc in DCM to give (R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (2c) (320 mg, 0.78 mmol, 55.9% yield) and (R)-[(3aR,4R,6R,6aR)-4-(4-methoxypyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (140 mg, 0.33 mmol, 23.6% yield).

Step 3. Synthesis of (2R,3R,4S,5R)-2-(4-amino-7H-pyrrolo[2,3-d]pyrimidin-7-yl)-5-((R)-bicyclo[4.2.0]octa-1(6),2,4-trien-3-yl(hydroxy)methyl)tetrahydrofuran-3,4-diol (2)

To a stirred solution of crude (R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (122 mg, 0.300 mmol) in Methanol (2 mL) was added Hydrochloric acid, 1 M (4. mL, 4 mmol) and the reaction was stirred for 4 h at rt. LCMS showed completion and the reaction was cooled to 0° C. and neutralized by the careful addition of Amberlite IRA-67. The reaction was filtered through filter paper and concentrated under reduced pressure. The crude was dried loaded on celite and purified on a silica gel column chromatography using CH$_2$Cl$_2$/CH$_2$Cl$_2$:MeOH 20% to give (2R,3R,4S,5R)-2-(4-aminopyrrolo[2,3-d]pyrimidin-7-yl)-5-[(R)-4-bicyclo[4.2.0]octa-1,3,5-trienyl(hydroxy)methyl]tetrahydrofuran-3,4-diol (Ex 2) (70 mg, 0.18 mmol, 59% yield) as a white solid. $^1$H NMR (400 MHz, Methanol-d4) δ 8.09 (s, 1H), 7.33-7.24 (m, 1H), 7.21 (d, J=3.7 Hz, 1H), 7.17 (s, 1H), 7.03 (d, J=7.6 Hz, 1H), 6.60 (d, J=3.6 Hz, 1H), 5.89 (d, J=7.6 Hz, 1H), 4.97 (d, J=2.4 Hz, 1H), 4.81 (dd, J=5.2, 7.7 Hz, 1H), 4.25 (s, 1H), 4.24-4.23 (m, 1H), 3.17 (s, 4H). LCMS: [M+H] 369.0.

Example 6. (2R,3R,4S,5R)-2-(4-amino-5-fluoropyrrolo[2,3-d]pyrimidin-7-yl)-5-[(R)-4-bicyclo[4.2.0]octa-1,3,5-trienyl(hydroxy)methyl]tetrahydrofuran-3,4-diol hydrochloride (Ex. 6)

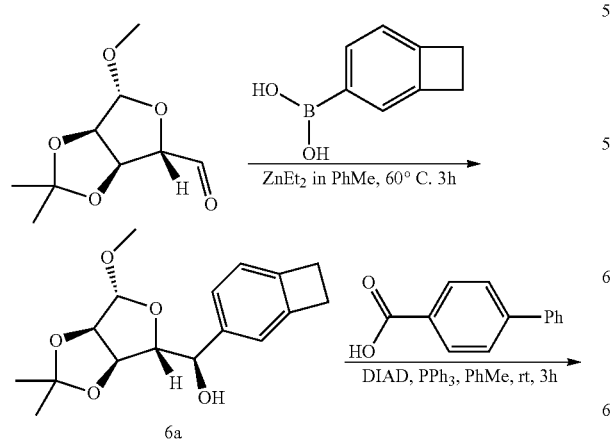

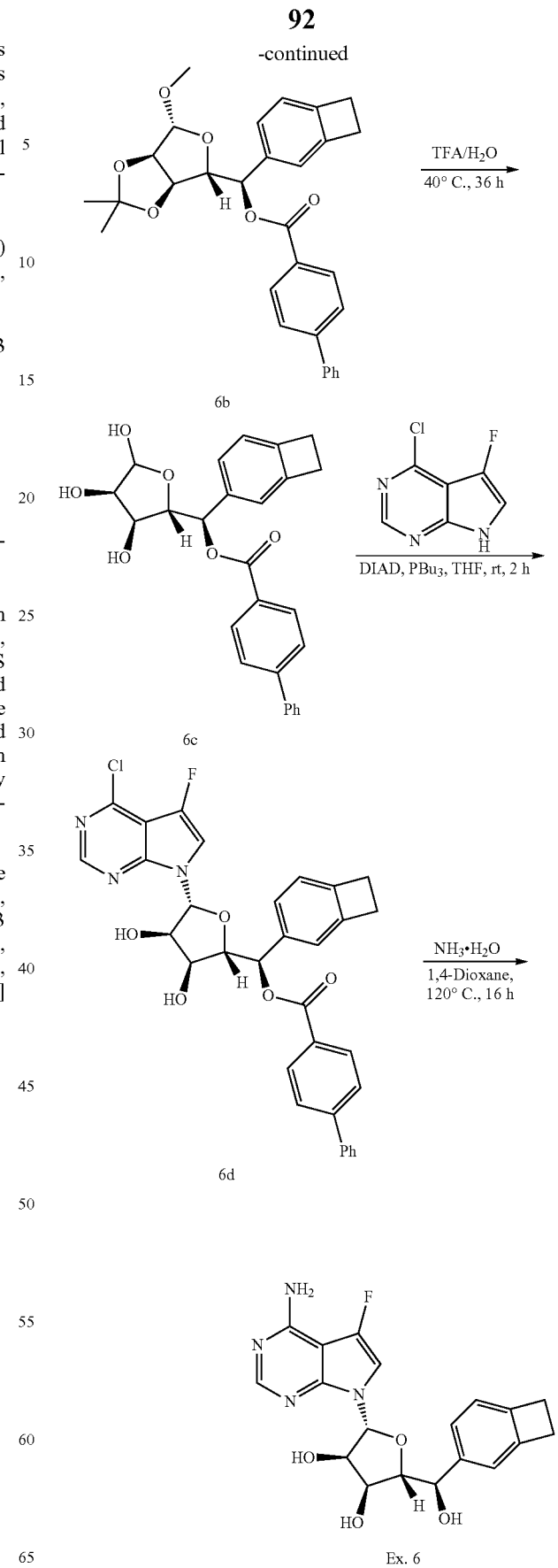

a) Synthesis of (S)-[(3aR,4R,6R,6aR)-4-methoxy-2,2-dimethyl-3a,4,6,6a-tetrahydrofuro[3,4-d][1,3]dioxol-6-yl]-(4-bicyclo[4.2.0]octa-1,3,5-trienyl)methanol (6a)

To a solution of 4-bicyclo[4.2.0]octa-1,3,5-trienylboronic acid (3500.0 mg, 23.65 mmol) in Toluene (90 mL), Diethylzinc (23.74 mL, 47.48 mmol) was added slowly at 25° C. The mixture was stirred at 60° C. for 1 hrs. (3aR,4R,6S,6aR)-4-methoxy-2,2-dimethyl-3a,4,6,6a-tetrahydrofuro[3,4-d][1,3]dioxole-6-carbaldehyde (3200.0 mg, 15.83 mmol) in Toluene (40 mL) was added slowly at 60° C. The mixture was stirred at 60° C. for 2 hrs. TLC (PE/EA=5/1) showed the reaction was completed. Water (10 ml) was added to quench the reaction. The mixture was filtered. The filtrate was concentrated and purified by combi-flash eluting with $CH_3CN/H_2O$ (neutral condition) from 5/95 to 85/15 to give (S)-[(3aR,4R,6R,6aR)-4-methoxy-2,2-dimethyl-3a,4,6,6a-tetrahydrofuro[3,4-d][1,3]dioxol-6-yl]-(4-bicyclo[4.2.0]octa-1,3,5-trienyl)methanol (6a) (2900 mg, 9.466 mmol, 55.8% yield) as a white solid.

b) Synthesis of [(R)-[(3aR,4R,6R,6aR)-4-methoxy-2,2-dimethyl-3a,4,6,6a-tetrahydrofuro[3,4-d] [1,3]dioxol-6-yl]-(4-bicyclo[4.2.0]octa-1,3,5-trienyl)methyl]4-phenylbenzoate (6b)

To a mixture of (S)-[(3aR,4R,6R,6aR)-4-methoxy-2,2-dimethyl-3a,4,6,6a-tetrahydrofuro[3,4-d][1,3]dioxol-6-yl]-(4-bicyclo[4.2.0]octa-1,3,5-trienyl)methanol (6a) (2900 mg, 9.47 mmol), 4-phenylbenzoic acid (2815 mg, 14.2 mmol) and Triphenylphosphine (3724 mg, 14.2 mmol) in Toluene (50 mL), DIAD (2.8 mL, 14.2 mmol) was added at 0° C. The mixture was stirred at 25° C. for 3 hrs. The mixture was concentrated and purified by combi-flash eluting with $CH_3CN/H_2O$ (neutral) from 5/95 to 95/5 to give [(R)-[(3aR,4R,6R,6aR)-4-methoxy-2,2-dimethyl-3a,4,6,6a-tetrahydrofuro[3,4-d] [1,3]dioxol-6-yl]-(4-bicyclo[4.2.0]octa-1,3,5-trienyl)methyl]4-phenylbenzoate (6b) (3700 mg, 7.604 mmol, 80.33% yield) as a white solid.

c) Synthesis of [(R)-4-bicyclo[4.2.0]octa-1,3,5-trienyl-[(2S,3S,4R)-3,4,5-trihydroxytetrahydro furan-2-yl]methyl]4-phenylbenzoate (6c)

A mixture of [(R)-[(3aR,4R,6R,6aR)-4-methoxy-2,2-dimethyl-3a,4,6,6a-tetrahydrofuro[3,4-d][1,3]dioxol-6-yl]-(4-bicyclo[4.2.0]octa-1,3,5-trienyl)methyl]4-phenylbenzoate (6b) (2421.41 mg, 4.98 mmol) in water (30.0 mL, 1664.8 mmol) and TFA (30.0 mL, 405.19 mmol) was heated to 40° C. and stirred for 36 h. TLC (PE/EA=1/1, Rf=0.3) showed the desired product. The mixture was concentrated and purified by purified by combi-flash eluting with $CH_3CN/H_2O$ (neutral) from 5/95 to 95/5 to give [(R)-4-bicyclo[4.2.0]octa-1,3,5-trienyl-[(2S,3S,4R)-3,4,5-trihydroxytetrahydro furan-2-yl]methyl]4-phenylbenzoate (6c) (1600 mg, 3.700 mmol, 74.34% yield) as white solid.

d) Synthesis of [(R)-4-bicyclo[4.2.0]octa-1,3,5-trienyl-[(2S,3S,4R,5R)-5-(4-chloro-5-fluoro-pyrrolo[2,3-d]pyrimidin-7-yl)-3,4-dihydroxy-tetrahydrofuran-2-yl]methyl]4-phenylbenzoate (6d)

To a solution of 4-chloro-5-fluoro-7H-pyrrolo[2,3-d]pyrimidine (79.34 mg, 0.46 mmol) in dry THF (10 mL) was added Pyridine (0.04 mL, 0.46 mmol), Then Tributylphosphane (0.23 mL, 0.92 mmol) and DIAD (0.2 mL, 1.02 mmol) was added at 25° C., [(R)-4-bicyclo[4.2.0]octa-1,3,5-trienyl-[(2S,3S,4R)-3,4,5-trihydroxytetrahydrofuran-2-yl]methyl]4-phenylbenzoate (6c) (200.0 mg, 0.46 mmol) in dry THF (5 mL) was added at once. The reaction mixture was stirred at 25° C. for 2 h. The reaction mixture was purified by reversed-phase combi-flash (neutral condition) eluting with $H_2O:CH_3CN$ from 90:10 to 5:95 to [(R)-4-bicyclo[4.2.0]octa-1,3,5-trienyl-[(2S,3S,4R,5R)-5-(4-chloro-5-fluoro-pyrrolo[2,3-d]pyrimidin-7-yl)-3,4-dihydroxy-tetrahydrofuran-2-yl]methyl]4-phenylbenzoate (6d) (111 mg, 0.189 mmol, 41.0% yield) as a pale yellow solid.

e) Synthesis of (2R,3R,4S,5R)-2-(4-amino-5-fluoro-pyrrolo[2,3-d]pyrimidin-7-yl)-5-[(R)-4-bicyclo[4.2.0]octa-1,3,5-trienyl(hydroxy)methyl]tetrahydrofuran-3,4-diol hydrochloride (Ex. 6)

To a mixture of [(R)-4-bicyclo[4.2.0]octa-1,3,5-trienyl-[(2S,3S,4R,5R)-5-(4-chloro-5-fluoro-pyrrolo [2,3-d]pyrimidin-7-yl)-3,4-dihydroxy-tetrahydrofuran-2-yl]methyl]4-phenylbenzoate (6d) (111.0 mg, 0.19 mmol) in 1,4-Dioxane (3 mL), Ammonium hydroxide (3.0 mL, 77.89 mmol) was added. The mixture was stirred at 120° C. for 16 hrs. LCMS (SYZ003-81-R1) showed the reaction has been completed. The mixture was concentrated and purified by prep-HPLC eluting with $CH_3CN/H_2O$ (0.1% TFA) from 5/95 to 95/5 to give the solution of desired product which was added 2 M HCl (4 mL) and lyophilizated to give (2R,3R,4S,5R)-2-(4-amino-5-fluoro-pyrrolo[2,3-d]pyrimidin-7-yl)-5-[(R)-4-bicyclo[4.2.0]octa-1,3,5-trienyl(hydroxy)methyl]tetrahydrofuran-3,4-diol hydrochloride (Ex. 6) (24.9 mg, 0.056 mmol, 69.7% yield) as a white solid. $^1$H NMR and $^{19}$F NMR verified the product. $^1$H NMR (400 MHz, DMSO-d6): δ 8.65 (brs, 2H), 8.35 (s, 1H), 7.63 (s, 1H), 7.20 (d, J=7.6 Hz, 1H), 7.10 (s, 1H), 7.01 (d, J=7.6 Hz, 1H), 6.11 (d, J=7.2 Hz, 1H), 4.71 (d, J=4.8 Hz, 1H), 4.39-4.43 (m, 1H), 4.09 (d, J=4.8 Hz, 1H), 3.99 (d, J=4.4 Hz, 1H), 3.09 (s, 4H). $^1$H NMR (400 MHz, DMSO-d6+D$_2$O): δ 8.33 (s, 1H), 7.60 (d, J=1.6 Hz, 1H), 7.20 (d, J=7.6 Hz, 1H), 7.10 (s, 1H), 7.02 (d, J=7.6 Hz, 1H), 6.12 (d, J=7.6 Hz, 1H), 4.71 (d, J=4.8 Hz, 1H), 4.39-4.43 (m, 1H), 4.10 (d, J=5.2 Hz, 1H), 4.01 (d, J=4.8 Hz, 1H), 3.10 (s, 4H). 19F NMR (376 MHz, DMSO-d6): δ −164.51 (s, 1F).

Example 11. (2R,3S,4R,5R)-2-((R)-bicyclo[4.2.0]octa-1(6),2,4-trien-3-yl(hydroxy)methyl)-5-(4-methyl-7H-pyrrolo[2,3-d]pyrimidin-7-yl)tetrahydrofuran-3,4-diol (11)

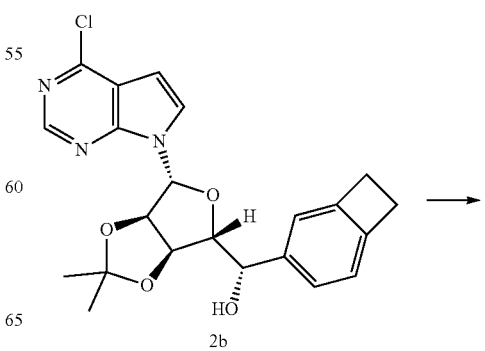

2b

-continued

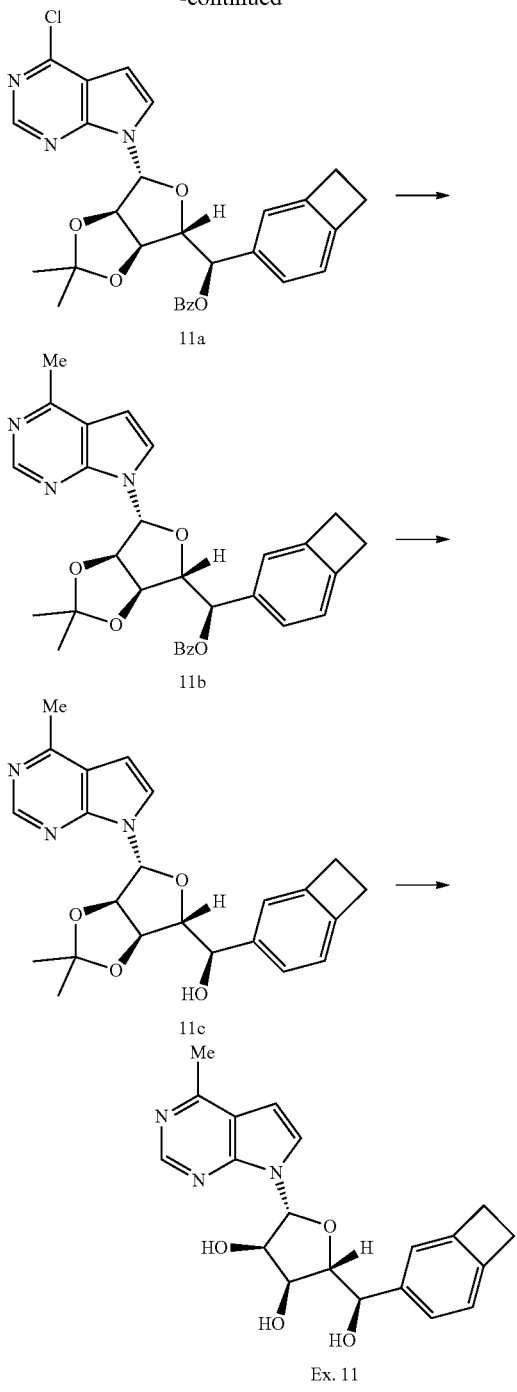

Step 1. Synthesize of [(R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1(6),2,4-trienyl)methyl]benzoate (11a)

Isopropyl (NE)-N-isopropoxycarbonyliminocarbamate (0.31 mL, 1.55 mmol) was added dropwise to a solution of (S)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1(6),2,4-trienyl)methanol (2b) (368. mg, 0.86 mmol) and triphenylphosphine (345 mg, 1.29 mmol) in THE (5 mL) at RT. The reaction became warm. The reaction mixture was stirred at RT overnight. TLC (3:1 hexane:EA) showed 2b was consumed. The reaction was concentrated under vacuum and the crude product was purified on a 20 g column to give [(R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1(6),2,4-trienyl)methyl]benzoate (11a) (290 mg, 0.545 mmol, 63.4% yield) as a white foamy solid.

Step 2. Synthesis of (R)-bicyclo[4.2.0]octa-1,3,5-trien-3-yl((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methyl benzoate (11b)

A 100 mL RBF with septum containing [(R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methyl]benzoate (272 mg, 0.51 mmol) and palladium; triphenylphosphane (30 mg, 0.030 mmol) under Ar was charged with THE (4 mL) and purged with Ar for 1 min (bright yellow sol'n). The vial was then charged with Dimethylzinc (1.0 mL, 2.0 mmol) (extreme care to avoid contact with air, pull back on syringe to fill needle volume with Ar/N2 before transferring between vessels, excess/residual reagent in syringe was diluted in test tube containing hexanes and let quench by air), and heated at 70° C. for 2.5 h. Complete by LCMS analysis. The reaction mixture was quenched by dropwise addition of sat. NaHCO$_3$(2 mL) at rt under Ar with vigorous stirring. The reaction mixture was diluted with EtOAc (30 mL) and vacuum filtered through a cellulose acetate filter. The salts were vigorously rinsed with water (20 mL) and EtOAc (20 mL). The filtrate was diluted with water (30 mL) and extracted with EtOAc (50 mL). The organic fraction was washed with water (70 mL), brine (40 mL), dried over Na$_2$SO$_4$, and filtered. The filtrate was concentrated under reduced pressure and purified by FCC (20 g SiO$_2$, 0→60% EtOAc in hexanes, wet-loaded in DCM). Fractions containing product were combined and concentrated under reduced pressure and heat (50° C.) to yield [(R)-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-(4-bicyclo[4.2.0]octa-1,3,5-trienyl)methyl]benzoate (197 mg, 0.381 mmol, 74.6% yield) as a yellow foam/gum. Rf=0.55 (2:1 EtOAc:hexanes); LCMS Found: 512.1; $^1$H NMR (400 MHz, Chloroform-d) δ 8.72 (s, 1H), 8.02-7.94 (m, 2H), 7.55 (tt, J=1.4, 7.5 Hz, 1H), 7.39 (tt, J=1.3, 7.6 Hz, 2H), 7.10 (d, J=3.7 Hz, 1H), 7.08-7.01 (m, 1H), 6.97-6.91 (m, 2H), 6.46 (d, J=3.7 Hz, 1H), 6.23 (d, J=2.6 Hz, 1H), 6.19 (d, J=5.9 Hz, 1H), 5.49 (dd, J=2.6, 6.4 Hz, 1H), 5.21 (dd, J=3.0, 6.4 Hz, 1H), 4.68 (dd, J=3.0, 5.9 Hz, 1H), 3.13-3.04 (m, 4H), 2.67 (s, 3H), 1.63 (s, 3H), 1.40 (s, 3H).

Step 3. Synthesis of (R)-bicyclo[4.2.0]octa-1,3,5-trien-3-yl((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanol (11c)

A 100 mL RBF containing a solution of [(R)-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-(4-bicyclo[4.2.0]octa-1,3,5-trienyl)methyl]benzoate (11b) (197. mg, 0.39 mmol) in Methanol (3 mL) was purged with Ar for 2 min. The solution was charged with sodium methoxide, 0.5 M in MeOH (2. mL, 1 mmol) and stirred at RT for 3 d. The reaction mixture was neutralized with NH$_4$Cl (20 mL), diluted with water (30 mL), and extracted with EtOAc (50 mL). The organic fraction was washed with brine (25 mL), dried over Na$_2$SO$_4$, filtered, and concentrated under reduced pressure and heat (50° C.) to give 257 mg crude product (11c). Rf=0.51 (2:1 EtOAc:hexanes). LCMS: [M+H]408.1

Step 4. Synthesis of (2R,3S,4R,5R)-2-((R)-bicyclo[4.2.0]octa-1(6),2,4-trien-3-yl(hydroxy)methyl)-5-(4-methyl-7H-pyrrolo[2,3-d]pyrimidin-7-yl)tetrahydrofuran-3,4-diol (11)

A 100 mL RBF with septum containing (R)-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-(4-bicyclo[4.2.0]octa-1,3,5-trienyl)methanol (11c) (156.9 mg, 0.39 mmol) under Ar was charged with Methanol (3 mL). The solution was purged with Ar for 1 min, then charged with 1 M Hydrochloric acid (aq) (3 mL, 3 mmol) and stirred at RT for 16 h. The reaction mixture was quenched with sat. sodium bicarbonate (3 mL), then diluted with water (20 mL) and brine (40 mL). The mixture was extracted with DCM (2×50 mL) then 20% MeOH in DCM (2×50 mL). The organic fractions were combined, dried over Na$_2$SO$_4$, filtered, and purified by FCC (20 g SiO$_2$, 0→8% MeOH in DCM, wet-loaded in DCM). Fractions containing pure product were combined and concentrated under reduced pressure and heat (50° C.) to yield (2R,3S,4R,5R)-2-[(R)-4-bicyclo[4.2.0]octa-1,3,5-trienyl(hydroxy)methyl]-5-(4-methylpyrrolo[2,3-d]pyrimidin-7-yl)tetrahydrofuran-3,4-diol (Ex 11) (150 mg, 100% yield) as a white foam/powder. Crystalline under microscope. $^1$H NMR (400 MHz, DMSO-d$_6$) δ 8.65 (s, 1H), 7.77 (d, J=3.8 Hz, 1H), 7.21 (dd, J=1.3, 7.6 Hz, 1H), 7.10 (s, 1H), 7.00 (d, J=7.5 Hz, 1H), 6.78 (d, J=3.7 Hz, 1H), 6.14 (d, J=7.8 Hz, 1H), 5.96 (d, J=4.1 Hz, 1H), 5.26 (d, J=7.0 Hz, 1H), 5.07 (d, J=4.0 Hz, 1H), 4.74 (t, J=4.5 Hz, 1H), 4.58 (td, J=5.0, 7.5 Hz, 1H), 4.10 (t, J=4.6 Hz, 1H), 4.00 (d, J=4.7 Hz, 1H), 3.08 (s, 4H), 2.66 (s, 3H); $^1$H NMR (400 MHz, DMSO-d$_6$+D$_2$O) δ 8.58 (s, 1H), 7.62 (t, J=4.1 Hz, 1H), 7.14 (d, J=7.6 Hz, 1H), 7.03 (s, 1H), 6.97 (d, J=7.6 Hz, 1H), 6.77 (d, J=2.2 Hz, 1H), 6.10-6.04 (m, 1H), 4.68 (d, J=4.7 Hz, 1H), 4.54 (dd, J=5.2, 7.6 Hz, 1H), 4.02 (d, J=4.9 Hz, 1H), 3.03 (s, 4H), 2.63 (s, 3H). LCMS [M+H]: 368.1

Example 20. 7-((2R,3R,4S,5R)-5-((R)-bicyclo[4.2.0]octa-1(6),2,4-trien-3-yl(hydroxy)methyl)-3,4-dihydroxytetrahydrofuran-2-yl)-3,7-dihydro-4H-pyrrolo[2,3-d]pyrimidin-4-one O-Methyl Oxime (20)

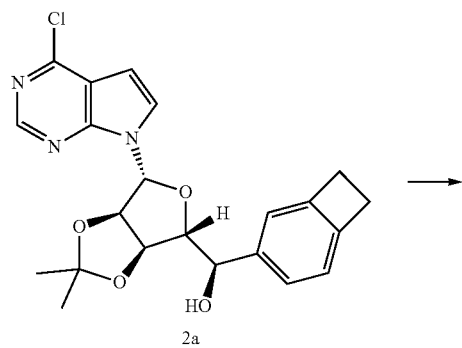

2a

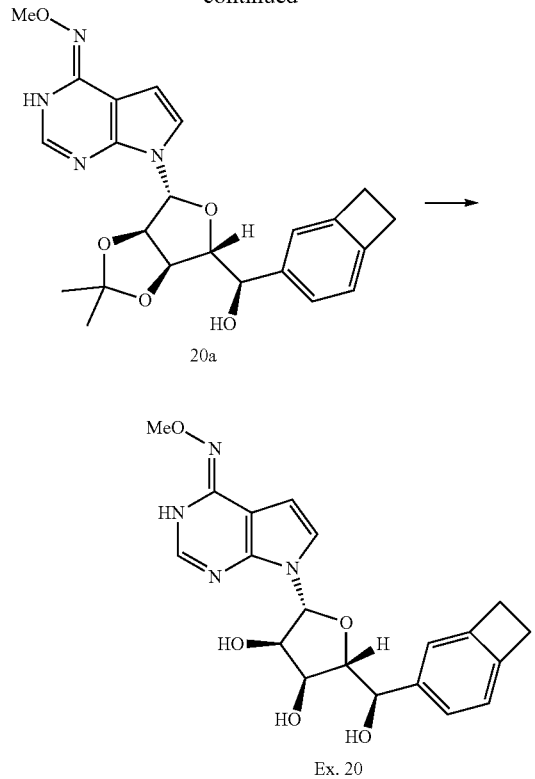

20a

Ex. 20

Step 1. Synthesis of (R)-[(3aR,4R,6R,6aR)-4-[(4E)-4-methoxyimino-1H-pyrrolo[2,3-d]pyrimidin-7-yl]-2,2-dimethyl-3a,4,6,6a-tetrahydrofuro[3,4-d][1,3]dioxol-6-yl]-(4-bicyclo[4.2.0]octa-1,3,5-trienyl)methanol (20a)

To (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (2a) (138. mg, 0.320 mmol) in 1-Butanol (2.7 mL) was added N-ethyl-N-isopropyl-propan-2-amine (0.40 mL, 2.26 mmol), and O-Methylhydroxylamine hydrochloride (135 mg, 1.61 mmol). The reaction was heated at 120° C. After 24 h LCMS showed 1:1 ratio of starting material and product. Another portion of O-Methylhydroxylamine hydrochloride (135 mg, 1.61 mmol) and N-ethyl-N-isopropyl-propan-2-amine (0.40 mL, 2.26 mmol) were added and the reaction was stirred for further 16 h at 120° C. LCMS showed almost completion and the reaction was concentrated under reduced pressure, dissolved in EtOAc and washed with water. The aqueous was back extracted with EtOAc and the combined organic layers were washed with brine, dried over Na$_2$SO$_4$ and concentrated under reduced pressure. The crude was purified on a 12 g silica gel column chromatography using EtOAc in CH$_2$Cl$_2$ (first 1 min only DCM followed by ramp up for 11 min until 40% of EtOAc and 5 min at 40%) to give 11 mg of recovered starting material and (R)-[(3aR,4R,6R,6aR)-4-[(4E)-4-methoxyimino-1H-pyrrolo[2,3-d]pyrimidin-7-yl]-2,2-dimethyl-3a,4,6,6a-tetrahydrofuro[3,4-d][1,3]dioxol-6-yl]-(4-bicyclo[4.2.0]octa-1,3,5-trienyl)methanol (20a) (50 mg, 0.11 mmol, 35% yield)

Step 2. Synthesis of 7-((2R,3R,4S,5R)-5-((R)-bicyclo[4.2.0]octa-1(6),2,4-trien-3-yl(hydroxy)methyl)-3,4-dihydroxytetrahydrofuran-2-yl)-3,7-dihydro-4H-pyrrolo[2,3-d]pyrimidin-4-one O-Ethyl Oxime (20)

To a 100 mL RBF with septum containing a solution of (R)-[(3aR,4R,6R,6aR)-4-[3-[(Z)-methoxyiminomethyl]pyrrol-1-yl]-2,2-dimethyl-3a,4,6,6a-tetrahydrofuro[3,4-d][1,3]dioxol-6-yl]-(4-bicyclo[4.2.0]octa-1,3,5-trienyl)methanol (20a) (40. mg, 0.090 mmol) in Methanol (0.70 mL) was added Hydrochloric acid, 1 M (1.4 mL, 1.4 mmol) dropwise and the reaction mixture was stirred at rt for 3 h. The reaction was cooled to 0° C. (ice bath) neutralized with aqueous NaHCO$_3$, concentrated under reduced pressure and extracted with CH$_2$Cl$_2$. The organic layer was dried over Na$_2$SO$_4$, filtered, and concentrated under reduced pressure. The crude was purified on a 4 g silica gel column chromatography using CH$_2$Cl$_2$/CH$_2$Cl$_2$: MeOH 20% (1 min only CH$_2$Cl$_2$ then ramp up for 7 min until 50% of solvent B) to give (2R,3S,4R,5R)-2-[(R)-4-bicyclo[4.2.0]octa-1,3,5-trienyl(hydroxy)methyl]-5-[(4Z)-4-methoxyimino-1H-pyrrolo[2,3-d]pyrimidin-7-yl]tetrahydrofuran-3,4-diol (Ex 20) (12.9 mg, 0.0323 mmol, 38.0% yield) as a white solid. $^1$H NMR (400 MHz, Methanol-d4) δ 8.38 (br s, 1H), 7.57 (br s, 1H), 7.26 (d, J=7.6 Hz, 1H), 7.14 (s, 1H), 7.02 (d, J=7.7 Hz, 1H), 6.43 (br s, 1H), 5.87 (br s, 1H), 4.93 (d, J=2.9 Hz, 1H), 4.65 (br, 1H), 4.22 (m, 2H), 3.83 (s, 3H), 3.15 (s, 4H). LCMS [M+H]: 399.04

Example 21. 7-((2R,3R,4S,5R)-5-((R)-bicyclo[4.2.0]octa-1(6),2,4-trien-3-yl(hydroxy)methyl)-3,4-dihydroxytetrahydrofuran-2-yl)-3,7-dihydro-4H-pyrrolo[2,3-d]pyrimidin-4-one O-Ethyl Oxime (21)

Example 21 was prepared via similar procedures to those of preparing Ex 20 except for substituting O-Methylhydroxylamine hydrochloride with O-Ethylhydroxylamine hydrochloride. $^1$H NMR (400 MHz, Methanol-d4) (possible tautomers) δ 8.19 (br s, 1H), 7.58 (s, 1H), 7.28-7.04 (m, 3H), 6.66 (br s, 0.4H), 6.42 (br s, 0.6H), 5.9 (br s, 0.4H), 5.85 (d, J=7.6 Hz, 0.6H), 4.9 (br s, 1H), 4.82 (br s, 0.4H), 4.64 (br s, 0.6H), 4.25 (m, 2H), 4.07 (q, J=7.2 Hz, 2H), 3.18 (s, 4H), 1.35 (m, 3H). LCMS [M+H]: 413.1.

Example 22. 7-((2R,3R,4S,5S)-5-((R)-1-(bicyclo[4.2.0]octa-1(6),2,4-trien-3-yl)-1-hydroxyethyl)-3,4-dihydroxytetrahydrofuran-2-yl)-3,7-dihydro-4H-pyrrolo[2,3-d]pyrimidin-4-one O-Ethyl Oxime (22)

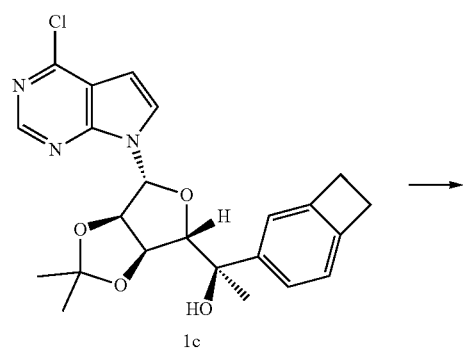

1c

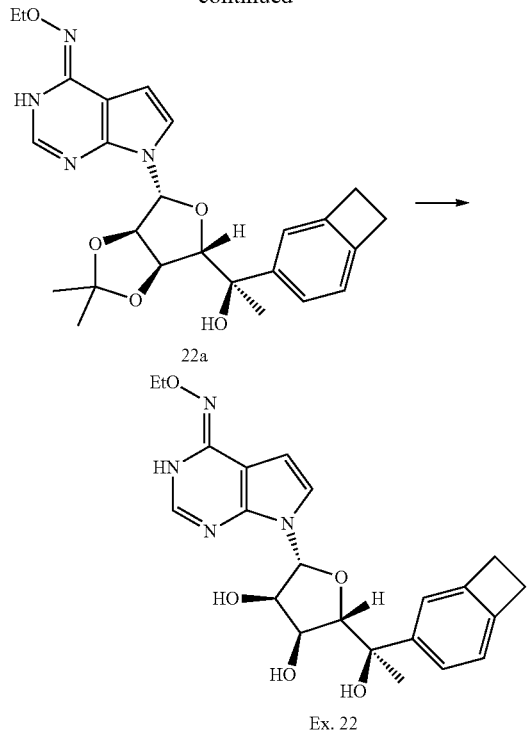

22a

Ex. 22

Step 1. Synthesis of 7-((3aR,4R,6S,6aR)-6-((R)-1-(bicyclo[4.2.0]octa-1,3,5-trien-3-yl)-1-hydroxyethyl)-2,2-dimethyltetrahydrofuro[3,4-d][1,3]dioxol-4-yl)-3,7-dihydro-4H-pyrrolo[2,3-d]pyrimidin-4-one O-Ethyl Oxime (22a)

To (1R)-1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(4-bicyclo[4.2.0]octa-1,3,5-trienyl)ethanol (1c) (210. mg, 0.48 mmol) in 1-Butanol (4 mL) was added ethoxyaminehydrochloride (239 mg, 2.38 mmol), and N-ethyl-N-isopropyl-propan-2-amine (0.59 mL, 3.33 mmol). The reaction was heated at 120° C. for 16 h. The reaction mixture was concentrated and the crude was extracted with ethyl acetate, washed with water, brine, dried over sodium sulfate, filtered and concentrated. The crude was purified by silica gel chromatography using 0-30% EtOAc in DCM to give 125 mg of the acetal oxime product (22a).

Step 2. Synthesis of 7-((2R,3R,4S,5S)-5-((R)-1-(bicyclo[4.2.0]octa-1(6),2,4-trien-3-yl)-1-hydroxyethyl)-3,4-dihydroxytetrahydrofuran-2-yl)-3,7-dihydro-4H-pyrrolo[2,3-d]pyrimidin-4-one O-Ethyl Oxime (22)

The acetal 22a was dissolved in 2 mL of methanol and treated with 2 mL of 1 N HCl and stirred for 16 h. The reaction mixture was cooled in an ice water bath and treated with dropwise addition of saturated sodium bicarbonate to pH 8. The reaction was extracted with ethyl acetate, washed with water, brine, dried over sodium sulfate, filtered and concentrated. The crude was purified by silica gel chromatography using 0-10% methanol in DCM on a 12 g Agela column to give (2S,3S,4R,5R)-2-[(1R)-1-(4-bicyclo[4.2.0]octa-1,3,5-trienyl)-1-hydroxy-ethyl]-5-[4-(ethoxyamino)

pyrrolo[2,3-d]pyrimidin-7-yl]tetrahydrofuran-3,4-diol (Ex 22) (94 mg, 0.22 mmol, 46% yield). ¹H NMR (400 MHz, Methanol-d4) (possible tautomers) δ 8.22 (br s, 1H), 7.60 (s, 0.6H), 7.39-7.13 (m, 3.4H), 6.64 (br s, 0.4H), 6.40 (d, J=3.4 Hz, 0.6H), 5.87 (d, J=8.0, 0.4H), 5.75 (d, J=8.0 Hz, 0.6H), 4.83 (m, 0.4H), 4.64 (m, 0.6H), 4.29-4.25 (m, 1H), 4.05 (q, J=7.0 Hz, 2H), 3.92 (m, 1H), 3.16 (s, 4H), 1.51 (s, 3H), 1.33 (m, 3H).

Example 23. 3-[7-[(2R,3R,4S,5R)-5-[(R)-4-bicyclo[4.2.0]octa-1,3,5-trienyl(hydroxy)methyl]-3,4-dihydroxy-tetrahydrofuran-2-yl]pyrrolo[2,3-d]pyrimidin-4-yl]-1,1-dimethyl-urea (Ex. 23)

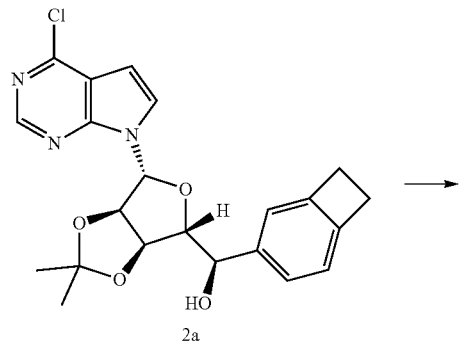

2a

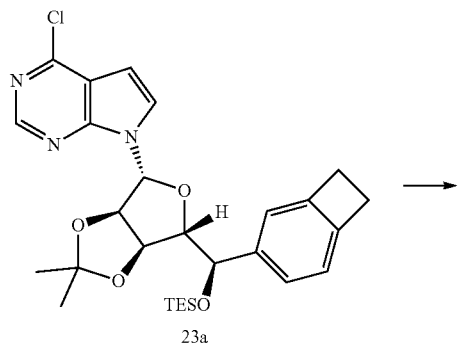

23a

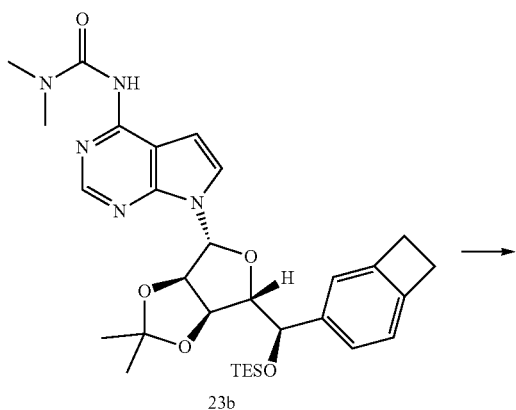

23b

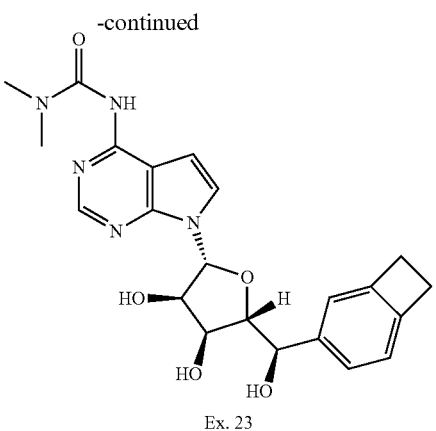

Ex. 23 a) Synthesis of [(R)-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methoxy]-triethyl-silane (23a)

To a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (2a) (400.0 mg, 0.93 mmol) and Imidazole (636.44 mg, 9.35 mmol) in DMF (5 mL) was added TESCl (704.5 mg, 4.67 mmol), the reaction mixture was stirred at 25° C. for 18h. LCMS showed the reaction was completed and the desired product was the main peak. The reaction mixture was purified by reversed-phase combi-flash (neutral condition) eluting with H₂O:CH₃CN from 40:60 to 0:100 to give [(R)-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methoxy]-triethyl-silane (23a) (484 mg, 0.8749 mmol, 93.588% yield) as an oil.

b) 3-[7-[(3aR,4R,6S,6aR)-6-[(R)-4-bicyclo[4.2.0]octa-1,3,5-trienyl(triethylsilyloxy)methyl]-2,2-dimethyl-3a,4,6,6a-tetrahydrofuro[3,4-d][1,3]dioxol-4-yl]pyrrolo[2,3-d]pyrimidin-4-yl]-1,1-dimethyl-urea (23b)

To a solution of [(R)-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methoxy]-triethyl-silane (23a) (3.77 g, 6.81 mmol), 1,1-dimethylurea (1.2 g, 13.63 mmol) and K₂CO₃ (2.35 g, 17.04 mmol) in 1,4-Dioxane (30 mL) was added Pd₂(dba)₃ (249.62 mg, 0.27 mmol) and xantphos (591.48 mg, 1.02 mmol) under N2, the reaction mixture was heated to 80° C. and stirred for 18 h. LCMS showed the reaction was completed, the reaction mixture was filtered through celite, and the filtrate was concentrated under reduced pressure to give crude product, which was purified by silica gel column chromatography (PE:EA=2:1) to give 3-[7-[(3aR,4R,6S,6aR)-6-[(R)-4-bicyclo[4.2.0]octa-1,3,5-trienyl(triethylsilyloxy)methyl]-2,2-dimethyl-3a,4,6,6a-tetrahydrofuro[3,4-d][1,3]dioxol-4-yl]pyrrolo[2,3-d]pyrimidin-4-yl]-1,1-dimethyl-urea (23b) (3.2 g, 4.3 mmol, 63% yield) as a solid.

c) Synthesis of 3-[7-[(2R,3R,4S,5R)-5-[(R)-4-bicyclo[4.2.0]octa-1,3,5-trienyl(hydroxy)methyl]-3,4-dihydroxy-tetrahydrofuran-2-yl]pyrrolo[2,3-d]pyrimidin-4-yl]-1,1-dimethyl-urea (Ex. 23)

To a solution of 3-[7-[(3aR,4R,6S,6aR)-6-[(R)-4-bicyclo[4.2.0]octa-1,3,5-trienyl(triethylsilyloxy)methyl]-2,2-dimethyl-3a,4,6,6a-tetrahydrofuro[3,4-d][1,3]dioxol-4-yl]pyrrolo[2,3-d]pyrimidin-4-yl]-1,1-dimethyl-urea (23b) (1.6 g, 2.16 mmol) in Water (12 mL) and TFA (8.0 mL, 107.7 mmol) was stirred at 25° C. for 1.5 h. LCMS showed the reaction was completed. The solvent was concentrated under reduced pressure, the residue was dissolved in DMSO and purified by prep-HPLC (0.1% NH$_3$.H$_2$O) eluting with H$_2$O:CH$_3$CN from 90:10 to 5:95 to give 3-[7-[(2R,3R,4S,5R)-5-[(R)-4-bicyclo[4.2.0]octa-1,3,5-trienyl(hydroxy)methyl]-3,4-dihydroxy-tetrahydrofuran-2-yl]pyrrolo[2,3-d]pyrimidin-4-yl]-1,1-dimethyl-urea (Ex. 23) (600 mg, 1.3503 mmol, 62.64% yield) as a white solid. $^1$H NMR (400 MHz, DMSO-d6) δ 9.45 (s, 1H), 8.39 (s, 1H), 7.53 (d, J=3.6 Hz, 1H), 7.21 (d, J=8.0 Hz, 1H), 7.10 (s, 1H), 7.00 (d, J=7.2 Hz, 1H), 6.57 (d, J=3.2 Hz, 1H), 6.10 (d, J=7.6 Hz, 1H), 6.00 (s, 1H), 5.22 (d, J=7.2 Hz, 1H), 5.01 (d, J=3.6 Hz, 1H), 4.72 (t, J=4.0 Hz, 1H), 4.53-4.56 (m, 1H), 4.09 (t, J=4.4 Hz, 1H), 3.99 (d, J=4.4 Hz, 1H), 3.09 (s, 4H), 2.99 (s, 6H). $^1$H NMR (400 MHz, DMSO-d6+D$_2$O) δ 8.39 (s, 1H), 7.50 (d, J=3.6 Hz, 1H), 7.21 (d, J=7.6 Hz, 1H), 7.10 (s, 1H), 7.02 (d, J=7.2 Hz, 1H), 6.60 (d, J=4.0 Hz, 1H), 6.09 (d, J=7.6 Hz, 1H), 4.73 (d, J=4.8 Hz, 1H), 4.55-4.58 (m, 1H), 4.12 (d, J=5.6 Hz, 1H), 4.03-4.04 (m, 1H), 3.10 (s, 4H). 3.00 (s, 6H).

Example 40. (2R,3S,4R,5R)-2-[(R)-4-bicyclo[4.2.0]octa-1,3,5-trienyl(hydroxy)methyl]-5-(4-isopropenylpyrrolo[2,3-d]pyrimidin-7-yl)tetrahydrofuran-3,4-diol (Ex. 40)

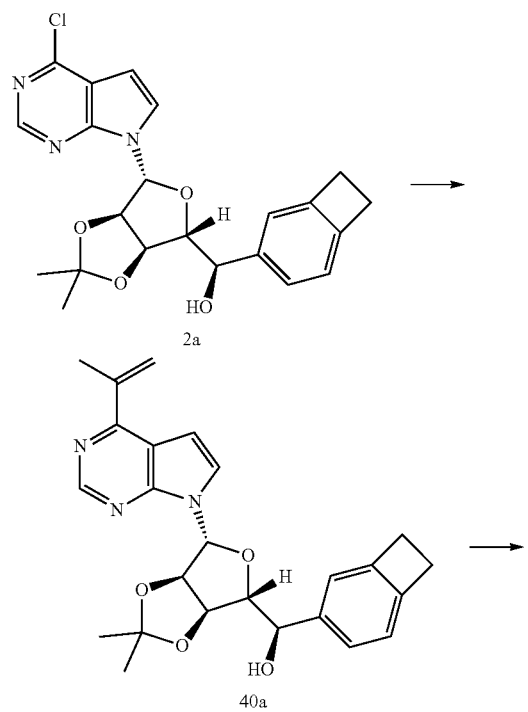

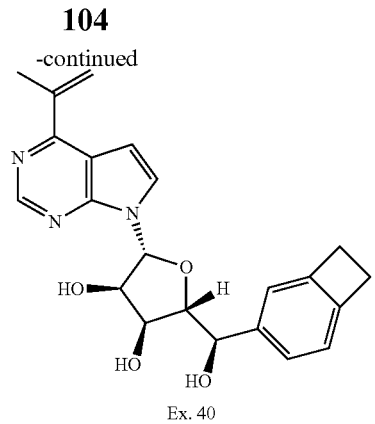

Ex. 40 a) Synthesis of (R)-[(3aR,4R,6R,6aR)-4-(4-isopropenylpyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (40a)

A mixture of 1,1'-Bis(diphenylphosphino)ferrocene-palladium(II)dichloride dichloromethane complex (95.43 mg, 0.12 mmol), Potassium carbonate (403.76 mg, 2.92 mmol), (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (2a) (500.0 mg, 1.17 mmol), 1,4-Dioxane (30 mL) and Water (6 mL) were degassed with N2, was added. The mixture was stirred at 90° C. for 16 hrs. LCMS showed the desired mass was detected. The mixture was filtered and concentrated, the residue was purified by combi-flash eluting with CH$_3$CN/H$_2$O (neutral) from 5/95 to 95/5 to give (R)-[(3aR,4R,6R,6aR)-4-(4-isopropenylpyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (40a) (440 mg, 1.02 mmol, 86.9% yield) as a yellow solid.

b) (2R,3S,4R,5R)-2-[(R)-4-bicyclo[4.2.0]octa-1,3,5-trienyl(hydroxy)methyl]-5-(4-isopropenylpyrrolo[2,3-d]pyrimidin-7-yl)tetrahydrofuran-3,4-diol (Ex. 40)

To a solution of (R)-[(3aR,4R,6R,6aR)-4-(4-isopropenylpyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (90.0 mg, 0.21 mmol) in CH$_3$CN (2 mL), TFA (0.8 mL, 11.6 mmol) and water (1.2 mL, 66.59 mmol) were added. The mixture was stirred at 40° C. for 1 h. LCMS showed the reaction has been completed. The mixture was purified by prep-HPLC eluting with CH$_3$CN/H$_2$O (0.1% TFA) from 5/95 to 95/5 to give (2R,3S,4R,5R)-2-[(R)-4-bicyclo[4.2.0]octa-1,3,5-trienyl(hydroxy)methyl]-5-(4-isopropenylpyrrolo[2,3-d]pyrimidin-7-yl)tetrahydrofuran-3,4-diol (Ex. 40) (44.5 mg, 0.1116 mmol, 53.755% yield) as a white solid. $^1$H NMR verified the product. $^1$H NMR (400 MHz, DMSO-d6): δ 8.82 (s, 1H), 7.92 (d, J=3.6 Hz, 1H), 7.22 (d, J=8.0 Hz, 1H), 7.11 (s, 1H), 7.00 (d, J=7.6 Hz, 1H), 6.93 (d, J=3.6 Hz, 1H), 6.23 (d, J=7.6 Hz, 1H), 6.04 (s, 1H), 5.74 (s, 1H), 4.75 (d, J=4.4 Hz, 1H), 4.56-4.60 (m, 1H), 4.14 (d, J=4.8 Hz, 1H), 4.03 (d, J=4.4 Hz, 1H), 3.09 (s, 4H), 2.28 (s, 3H). $^1$H NMR (400 MHz, DMSO-d6+D$_2$O): δ 8.84 (s, 1H), 7.91 (d, J=3.6 Hz, 1H), 7.17 (d, J=7.2 Hz, 1H), 7.07 (s, 1H), 6.97-7.01 (m, 2H), 6.21 (d, J=7.6 Hz, 1H), 6.03 (s, 1H), 5.82 (s, 1H), 4.71 (d, J=4.8

Hz, 1H), 4.53-4.56 (m, 1H), 4.14 (d, J=5.2 Hz, 1H), 4.05 (d, J=4.8 Hz, 1H), 3.06 (s, 4H), 2.28 (s, 3H).

Example 41. (2R,3S,4R,5R)-2-[(R)-4-bicyclo[4.2.0]
octa-1,3,5-trienyl(hydroxy)methyl]-5-(4-isopropylpyrrolo[2,3-d]pyrimidin-7-yl)tetrahydrofuran-3,4-diol (Ex. 41)

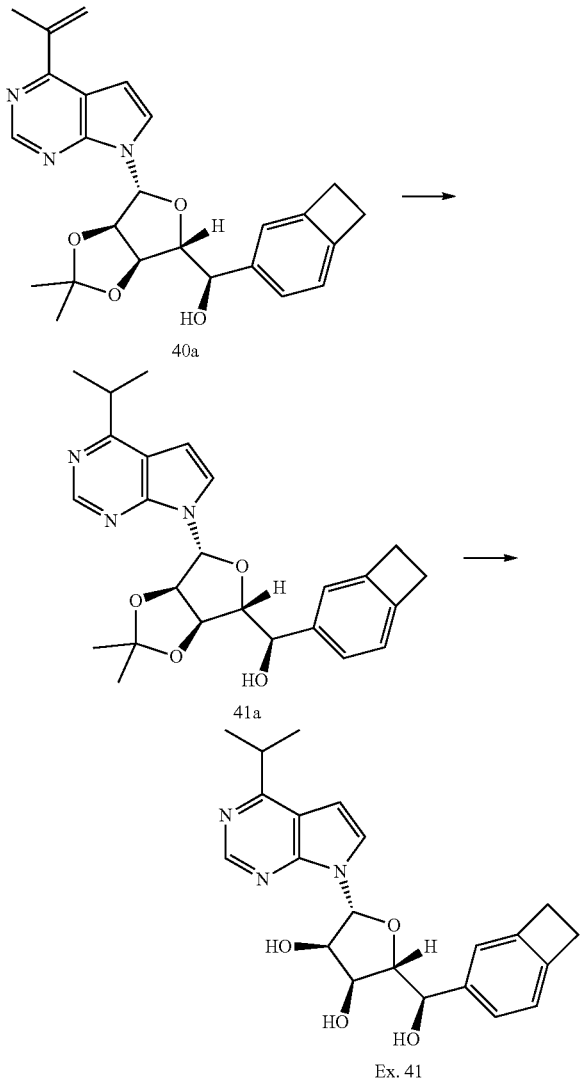

a) Synthesis of (R)-[(3aR,4R,6R,6aR)-4-(4-isopropylpyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (41a)

To a solution of (R)-[(3aR,4R,6R,6aR)-4-(4-isopropenylpyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (40a) (340.0 mg, 0.78 mmol) in Methanol (50 mL), Pd/C (340.0 mg, 0.32 mmol) was added. The mixture was stirred at 25° C. under a H2 balloon for 16 h. LCMS showed the reaction has been completed. The mixture was filtered through a pad of celite, the filtrate was concentrated to give the crude (R)-[(3aR,4R,6R,6aR)-4-(4-isopropylpyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (41a) (340 mg, 0.781 mmol, 99.5% yield) which was used directly for the next step.

b) (2R,3S,4R,5R)-2-[(R)-4-bicyclo[4.2.0]octa-1,3,5-trienyl(hydroxy)methyl]-5-(4-isopropylpyrrolo[2,3-d]pyrimidin-7-yl)tetrahydrofuran-3,4-diol (Ex. 41)

To a solution of (R)-[(3aR,4R,6R,6aR)-4-(4-isopropylpyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methanol (41a) (340.0 mg, 0.78 mmol) in CH$_3$CN (3 mL), TFA (1.2 mL, 17 mmol) and water (1.8 mL) were added. The mixture was stirred at 40° C. for 1 h. LCMS showed the reaction has been completed. The mixture was purified by prep-HPLC eluting with CH$_3$CN/H$_2$O (0.1% TFA) from 5/95 to 95/5 to give (2R,3S,4R,5R)-2-[(R)-4-bicyclo[4.2.0]octa-1,3,5-trienyl(hydroxy)methyl]-5-(4-isopropylpyrrolo[2,3-d]pyrimidin-7-yl)tetrahydrofuran-3,4-diol (Ex. 41) (167.2 mg, 0.416 mmol, 53.3% yield) as a white solid. $^1$H NMR verified the product. $^1$H NMR (400 MHz, DMSO-d6): δ 8.87 (s, 1H), 7.94 (d, J=3.6 Hz, 1H), 7.22 (d, J=7.6 Hz, 1H), 7.12 (s, 1H), 6.99-7.02 (m, 2H), 6.21 (d, J=7.6 Hz, 1H), 4.75 (d, J=4.8 Hz, 1H), 4.56-4.60 (m, 1H), 4.14 (d, J=4.8 Hz, 1H), 4.03 (d, J=4.8 Hz, 1H), 3.49-3.56 (m, 1H), 3.09 (s, 4H), 1.38 (d, J=6.8 Hz, 6H). $^1$H NMR (400 MHz, DMSO-d6+D$_2$O): δ 8.96 (s, 1H), 8.03 (d, J=3.6 Hz, 1H), 7.22 (d, J=3.6 Hz, 1H), 7.17 (d, J=4.0 Hz, 1H), 7.11 (s, 1H), 7.02 (d, J=7.6 Hz, 1H), 6.25 (d, J=7.6 Hz, 1H), 4.75 (d, J=4.8 Hz, 1H), 4.56-4.59 (m, 1H), 4.17 (d, J=4.8 Hz, 1H), 4.08 (d, J=4.8 Hz, 1H), 3.56-3.63 (m, 1H), 3.10 (s, 4H), 1.43 (d, J=7.2 Hz, 6H).

Example 43. (2R,3S,4R,5R)-2-[(R)-4-bicyclo[4.2.0]octa-1,3,5-trienyl(hydroxy)methyl]-5-[4-(hydroxymethyl)pyrrolo[2,3-d]pyrimidin-7-yl]tetrahydrofuran-3,4-diol (Ex. 43)

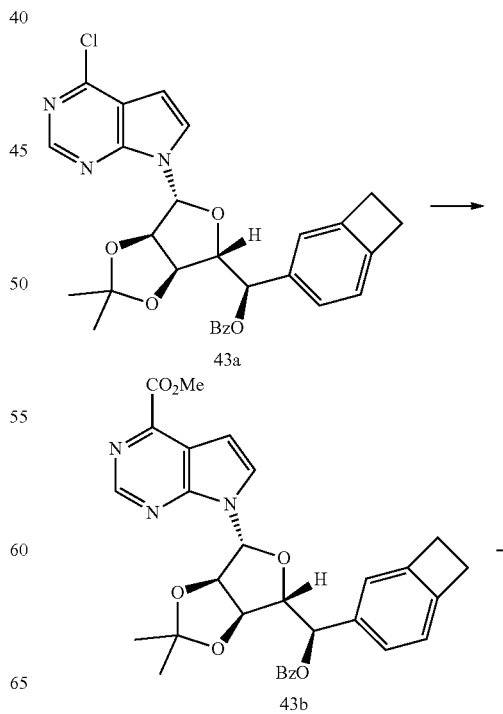

-continued

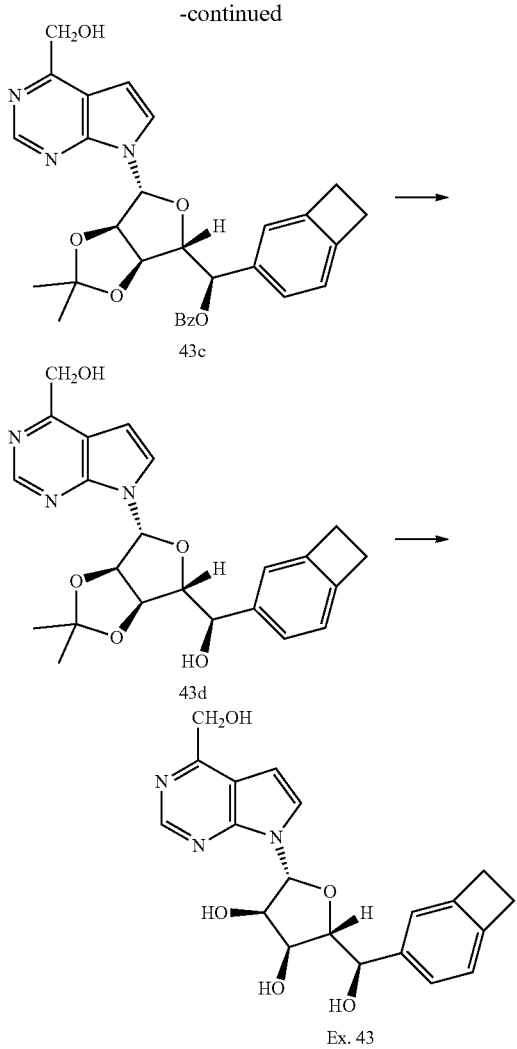

a) Synthesis of methyl 7-[(3aR,4R,6R,6aR)-6-[(R)-benzoyloxy(4-bicyclo[4.2.0]octa-1,3,5-trienyl)methyl]-2,2-dimethyl-3a,4,6,6a-tetrahydrofuro[3,4-d][1,3]dioxol-4-yl]pyrrolo[2,3-d]pyrimidine-4-carboxylate (43b)

To a solution of [(R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-bicyclo[4.2.0]octa-1,3,5-trienyl)methyl]benzoate (43a, prepared by procedures similar to that of 11a) (1.0 g, 1.88 mmol) in Methanol (250 mL) was added Pd(dppf)$_2$C$_{12}$ (153.51 mg, 0.19 mmol) under CO (5000 mg, 188 mmol), the reaction mixture was stirred at 50° C. for 18 h. LCMS showed the starting material was consumed and the desired product was the main peak. The reaction mixture was combined with previous reactions and purified. The solvent was removed in vacuo. The reaction mixture was diluted with H$_2$O (100 mL) and the mixture was extracted with EA (150 mL × 3), then the organic layer was washed with saturated NaCl (100 mL). The resulting organic layer was dried over anhydrous Na$_2$SO$_4$ and the solvent was removed in vacuo. The crude product was purified by column chromatography on silica gel (100-200 mesh size) using petroleum ether/EtOAc (50:1-1:1) as eluent to give methyl 7-[(3aR,4R,6R,6aR)-6-[(R)-benzoyloxy(4-bicyclo[4.2.0]octa-1,3,5-trienyl)methyl]-2,2-dimethyl-3a,4,6,6a-tetrahydrofuro[3,4-d][1,3]dioxol-4-yl]pyrrolo[2,3-d]pyrimidine-4-carboxylate (900 mg, 1.52 mmol, 80.7% yield) as a yellow oil. LCMS [M+H]: 556.2.

b) Synthesis of [(R)-[(3aR,4R,6R,6aR)-4-[4-(hydroxymethyl)pyrrolo[2,3-d]pyrimidin-7-yl]-2,2-dimethyl-3a,4,6,6a-tetrahydrofuro[3,4-d][1,3]dioxol-6-yl]-(4-bicyclo[4.2.0]octa-1,3,5-trienyl)methyl] benzoate (43c)

To a solution of methyl 7-[(3aR,4R,6R,6aR)-6-[(R)-benzoyloxy(4-bicyclo[4.2.0]octa-1,3,5-trienyl)methyl]-2,2-dimethyl-3a,4,6,6a-tetrahydrofuro[3,4-d][1,3]dioxol-4-yl]pyrrolo[2,3-d]pyrimidine-4-carboxylate (43b) (200.0 mg, 0.36 mmol) in THF (20 mL) was added under N$_2$ LiAlH$_4$ (20.49 mg, 0.54 mmol), the reaction mixture was stirred at 0° C. for 2 h. LCMS showed the starting material was consumed and the desired product was the main peak. The reaction mixture was combined with previous reactions and purified. The reaction was quenched with NH$_4$Cl (aq, 20.0 mL) and water (20.0 mL). The aqueous layer was extracted with EA (200.0 mL×3). The organic layers were concentrated in vacuum, The crude product was purified by column chromatography on silica gel (100-200 mesh size) using petroleum ether/ EtOAc (50:1-10:1) as eluent to give [(R)-[(3aR,4R,6R,6aR)-4-[4-(hydroxymethyl)pyrrolo[2,3-d]pyrimidin-7-yl]-2,2-dimethyl-3a,4,6,6a-tetrahydrofuro[3,4-d][1,3]dioxol-6-yl]-(4-bicyclo[4.2.0]octa-1,3,5-trienyl)methyl]benzoate (43c) (100 mg, 0.190 mmol, 52.7% yield) as a pale yellow solid.

c) Synthesis of (R)-[(3aR,4R,6R,6aR)-4-[4-(hydroxymethyl)pyrrolo[2,3-d]pyrimidin-7-yl]-2,2-dimethyl-3a,4,6,6a-tetrahydrofuro[3,4-d][1,3]dioxol-6-yl]-(4-bicyclo[4.2.0]octa-1,3,5-trienyl)methanol (43d)

A solution of [(R)-[(3aR,4R,6R,6aR)-4-[4-(hydroxymethyl)pyrrolo[2,3-d]pyrimidin-7-yl]-2,2-dimethyl-3a,4,6, 6a-tetrahydrofuro[3,4-d][1,3]dioxol-6-yl]-(4-bicyclo[4.2.0] octa-1,3,5-trienyl)methyl]benzoate (43c) (70.0 mg, 0.13 mmol) in Ethanol (3.5 mL) and Hydrazinium hydroxide (3.0 mL, 0.13 mmol) was stirred at 25° C. for 1 h. LCMS showed the starting material was consumed and the desired product was the main peak. The residue was purified by flash column chromatography (Eluent of 10-90% H$_2$O/CH$_3$CN on C-18). Then the resulting product was concentrated in vacuum to give (R)-[(3aR,4R,6R,6aR)-4-[4-(hydroxymethyl)pyrrolo [2,3-d]pyrimidin-7-yl]-2,2-dimethyl-3a,4,6,6a-tetrahydrofuro[3,4-d][1,3]dioxol-6-yl]-(4-bicyclo[4.2.0]octa-1,3,5-trienyl)methanol (43d) (35 mg, 0.083 mmol, 62% yield) as a pale yellow solid.

d) Synthesis of (2R,3S,4R,5R)-2-[(R)-4-bicyclo[4.2.0]octa-1,3,5-trienyl(hydroxy)methyl]-5-[4-(hydroxymethyl)pyrrolo[2,3-d]pyrimidin-7-yl]tetrahydrofuran-3,4-diol (Ex. 43)

A solution of (R)-[(3aR,4R,6R,6aR)-4-[4-(hydroxymethyl)pyrrolo[2,3-d]pyrimidin-7-yl]-2,2-dimethyl-3a,4,6, 6a-tetrahydrofuro[3,4-d][1,3]dioxol-6-yl]-(4-bicyclo[4.2.0] octa-1,3,5-trienyl)methanol (43d) (35.0 mg, 0.08 mmol) in Water (2 mL) and TFA (2.0 mL, 22.21 mmol) was stirred at 25° C. for 2 hrs. LCMS showed the starting material was consumed and the desired product was the main peak. The solvent was removed in vacuo and the crude product was purified by prep-HPLC (eluting with H₂O:CH₃CN (1% NH₃.H₂O) from 90:10 to 5:95) to obtain (2R,3S,4R,5R)-2-[(R)-4-bicyclo[4.2.0]octa-1,3,5-trienyl(hydroxy)methyl]-5-[4-(hydroxymethyl)pyrrolo[2,3-d]pyrimidin-7-yl]tetrahydrofuran-3,4-diol (Ex. 43) (18.3 mg, 0.0460 mmol, 55.6% yield) as a white solid. LCMS [M+H]: 384.2. ¹H NMR (400 MHz, DMSO-d6) δ 8.69 (s, 1H), 7.76-7.77 (d, J=3.6 Hz, 1H), 7.20-7.22 (m, 1H), 7.11 (s, 1H), 6.99-7.01 (s, 1H), 6.89-6.90 (d, J=3.6 Hz, 1H), 6.17-6.19 (d, J=7.6 Hz, 1H), 5.90-5.91 (d, J=4.0 Hz, 1H), 5.58-5.61 (m, 1H), 5.22-5.24 (d, J=7.2 Hz, 1H), 5.04-5.05 (d, J=4.0 Hz, 1H), 4.82-4.83 (d, J=6.0 Hz, 2H), 4.73-4.75 (m, 1H), 4.57-4.58 (m, 1H), 4.11-4.13 (m, 1H), 4.01-4.02 (m, 1H), 3.09 (s, 4H). ¹H NMR (400 MHz, DMSO-d6+D₂O) δ 8.69 (s, 1H), 7.74-7.75 (d, J=4.0 Hz, 1H), 7.20-7.22 (m, 1H), 7.10 (s, 1H), 7.00-7.02 (s, 1H), 6.89-6.90 (d, J=3.6 Hz, 1H), 6.17-6.19 (d, J=7.6 Hz, 1H), 4.83 (s, 2H), 4.73-4.74 (m, 1H), 4.56-4.59 (m, 1H), 4.12-4.13 (m, 1H), 4.02-4.03 (m, 1H), 3.09 (s, 4H).

Example 48. (2R,3S,4R,5R)-2-[(R)-4-bicyclo[4.2.0]octa-1,3,5-trienyl(hydroxy)methyl]-5-[4-(2-methoxyethyl)pyrrolo[2,3-d]pyrimidin-7-yl]tetrahydrofuran-3,4-diol (Ex. 48)

To a solution of [(R)-[(3aR,4R,6S,6aR)-2,2-dimethyl-4-(4-vinylpyrrolo[2,3-d]pyrimidin-7-yl)-3a,4,6,6a-tetrahydrofuro[3,4-d][1,3]dioxol-6-yl]-(4-bicyclo[4.2.0]octa-1,3,5-trienyl)methoxy]-triethyl-silane (prepared similarly to that of 40a) (50.0 mg, 0.09 mmol) in Methanol (3 mL) was added Potassium bisulfate (63.78 mg, 0.47 mmol). the mixture was stirred at 80° C. 4 hours. LC-MS showed the reaction was completed. The reaction mixture was filtered, the filtrate was purified by prep-HPLC, eluted with CH₃CN in H₂O (0.1% NH₄OH) from 5.0% to 95.0% to give (2R,3S,4R,5R)-2-[(R)-4-bicyclo[4.2.0]octa-1,3,5-trienyl(hydroxy)methyl]-5-[4-(2-methoxyethyl)pyrrolo[2,3-d]pyrimidin-7-yl]tetrahydrofuran-3,4-diol (Ex. 48) (10 mg, 0.024 mmol, 26% yield) as a white solid. ¹H NMR (400 MHz, DMSO-d6+D₂O): δ 8.69 (s, 1H), 7.75-7.76 (m, 1H), 7.20-7.22 (m, 1H), 7.10 (s, 1H), 7.00-7.01 (m, 1H), 6.81-6.82 (m, 1H), 6.15-6.17 (m, 1H), 4.72-4.74 (m, 1H), 4.56-4.60 (m, 1H), 4.11-4.12 (m, 1H), 4.01-4.03 (m, 1H), 3.80-3.83 (m, 2H), 3.20-3.24 (m, 5H), 3.06-3.10 (m, 4H).

Example 49. (2R,3S,4R,5R)-2-[(R)-4-bicyclo[4.2.0]octa-1,3,5-trienyl(hydroxy)methyl]-5-[4-(fluoromethyl)pyrrolo[2,3-d]pyrimidin-7-yl]tetrahydrofuran-3,4-diol (Ex. 49)

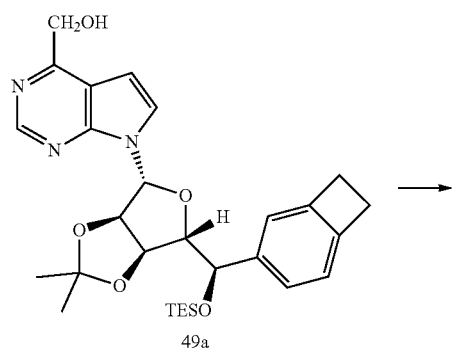

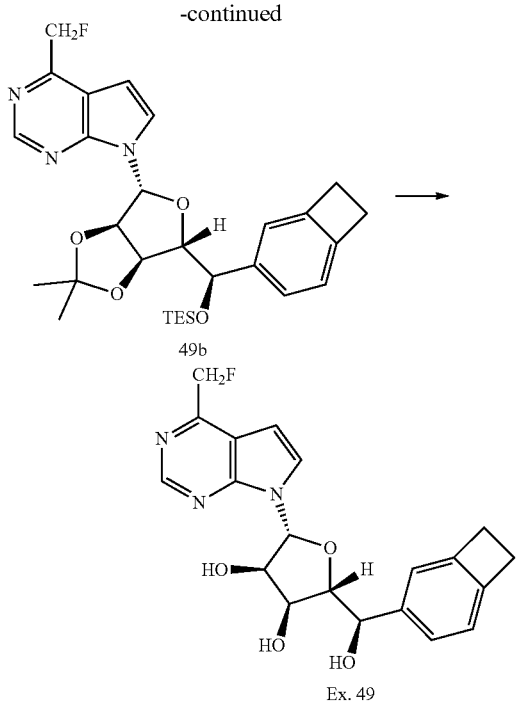

a) Synthesis of [(R)-[(3aR,4R,6S,6aR)-4-[4-(fluoromethyl)pyrrolo[2,3-d]pyrimidin-7-yl]-2,2-dimethyl-3a,4,6,6a-tetrahydrofuro[3,4-d][1,3]dioxol-6-yl]-(4-bicyclo[4.2.0]octa-1,3,5-trienyl)methoxy]-triethyl-silane (49b)

To a solution of N'-[1-[(3aR,4R,6S,6aR)-6-[(R)-4-bicyclo[4.2.0]octa-1,3,5-trienyl(triethylsilyloxy)methyl]-2,2-dimethyl-3a,4,6,6a-tetrahydrofuro[3,4-d][1,3]dioxol-4-yl]-3-(2-hydroxyethyl)pyrrol-2-yl]-N-methylene-formamidine (49a) (150.0 mg, 0.27 mmol) in DCM (20 mL) was added under DAST (218 mg, 1.35 mmol), the reaction mixture was stirred at 25° C. for 2 h. LCMS showed the reaction was completed. The reaction was combined with another batch and added to water (10 ml), extracted with DCM (20 ml*2). All of the DCM was concentrated and the residue was purified by gel chromatography (SiO2 200-300 mesh, PE:EA=10:1 to 3:1) to give [(R)-[(3aR,4R,6S,6aR)-4-[4-(fluoromethyl)pyrrolo[2,3-d]pyrimidin-7-yl]-2,2-dimethyl-3a,4,6,6a-tetrahydrofuro[3,4-d][1,3]dioxol-6-yl]-(4-bicyclo[4.2.0]octa-1,3,5-trienyl)methoxy]-triethyl-silane (49b) (55 mg, 0.096 mmol, 35% yield) as a yellow oil; LCMS M+H⁺ 540.3.

b) Synthesis of (2R,3S,4R,5R)-2-[(R)-4-bicyclo[4.2.0]octa-1,3,5-trienyl(hydroxy)methyl]-5-[4-(fluoromethyl)pyrrolo[2,3-d]pyrimidin-7-yl]tetrahydrofuran-3,4-diol (Ex. 49)

To a solution of TFA (1.0 mL, 13.46 mmol) and Water (1.5 mL) was added N'-[1-[(3aR,4R,6S,6aR)-6-[(R)-4-bicyclo[4.2.0]octa-1,3,5-trienyl(triethylsilyloxy)methyl]-2,2-dimethyl-3a,4,6,6a-tetrahydrofuro[3,4-d][1,3]dioxol-4-yl]-3-(2-fluoroethyl)pyrrol-2-yl]-N-methylene-formamidine (55.0 mg, 0.10 mmol), the reaction mixture was stirred at 40° C. for 1 h. LCMS showed the reaction was completed. The mixture was concentrated and purified by prep-HPLC eluting with CH₃CN/H₂O (0.1% TFA) from 5/95 to 95/5 to give the prepared solution which was lyophilized to give (2R,3S,4R,5R)-2-[(R)-4-bicyclo[4.2.0]octa-1,3,5-trienyl(hydroxy)methyl]-5-[4-(fluoromethyl)pyrrolo[2,3-d]pyrimidin-7-yl]tetrahydrofuran-3,4-diol (Ex. 49) (21.7 mg, 0.0557 mmol, 56.3% yield) as a white solid. $^1$H NMR (DMSO-d6, 400 MHz) δ 8.82 (s, 1H), 7.92 (s, 1H), 7.21 (d, J=8.0 Hz, 1H), 7.10 (s, 1H), 7.00 (d, J=7.2 Hz, 1H), 6.84 (s, 1H), 6.23 (d, J=8.0 Hz, 1H), 5.87 (s, 1H), 5.76 (s, 1H), 4.74-4.75 (m, 1H), 4.56-4.59 (m, 1H), 4.13-4.14 (m, 1H), 4.01-4.03 (m, 1H), 3.08 (s, 4H). $^1$H NMR (DMSO-d6+D₂O, 400 MHz) δ 8.84 (s, 1H), 7.92 (s, 1H), 7.21 (d, J=7.6 Hz, 1H), 7.10 (s, 1H), 7.00 (d, J=7.2 Hz, 1H), 6.85 (s, 1H), 6.23 (d, J=7.6 Hz, 1H), 5.80 (d, J=44 Hz, 2H), 4.73-4.75 (m, 1H), 4.56-4.59 (m, 1H), 4.13-4.14 (m, 1H), 4.02-4.04 (m, 1H), 3.08 (s, 4H).

Example 50 and 51. (2R,3R,4S,5R)-2-[4-(ethoxymethyl)pyrrolo[2,3-d]pyrimidin-7-yl]-5-[rac-(R)-3-bicyclo[4.2.0]octa-1,3,5-trienyl(hydroxy)methyl]tetrahydrofuran-3,4-diol (Ex. 50) (2R,3R,4S,5R)-2-[4-(chloromethyl)pyrrolo[2,3-d]pyrimidin-7-yl]-5-[rac-(R)-3-bicyclo[4.2.0]octa-1,3,5-trienyl(hydroxy)methyl]tetrahydrofuran-3,4-diol (Ex. 51)

a) Synthesis of triethyl-[(R)-3-bicyclo[4.2.0]octa-1,3,5-trienyl-[(3aR,4R,6S,6aR)-4-[4-(chloromethyl)pyrrolo[2,3-d]pyrimidin-7-yl]-2,2-dimethyl-3a,4,6,6a-tetrahydrofuro[3,4-d][1,3]dioxol-6-yl]methoxy]silane (50a)

To a solution of N'-[1-[(3aR,4R,6S,6aR)-6-[(R)-4-bicyclo[4.2.0]octa-1,3,5-trienyl(triethylsilyloxy)methyl]-2,2-dimethyl-3a,4,6,6a-tetrahydrofuro[3,4-d][1,3]dioxol-4-yl]-3-(2-hydroxyethyl)pyrrol-2-yl]-N-methylene-formamidine (49a) (100.0 mg, 0.18 mmol) in DCM (10 mL) was added TsCl (68.86 mg, 0.36 mmol), DMAP (4.41 mg, 0.04 mmol) and Triethylamine (0.08 mL, 0.54 mmol). The reaction mixture was stirred at 25° C. for 2 h. LCMS showed the reaction was completed but no tosylate was formed. The mixture was concentrated, the residue was purified by pre-TLC (PE: EA=2:1) to give triethyl-[(R)-3-bicyclo[4.2.0]octa-1,3,5-trienyl-[(3aR,4R,6S,6aR)-4-[4-(chloromethyl)pyrrolo[2,3-d]pyrimidin-7-yl]-2,2-dimethyl-3a,4,6,6a-tetrahydrofuro[3,4-d][1,3]dioxol-6-yl]methoxy]silane (50a) (30 mg, 0.05394 mmol, 29.871% yield) as a yellow oil. LCMS M+H⁺ 556.3/558.3.

b) Synthesis of triethyl-[rac-(R)-3-bicyclo[4.2.0]octa-1,3,5-trienyl-[rac-(3aR,4R,6S,6aR)-4-[4-(ethoxymethyl)pyrrolo[2,3-d]pyrimidin-7-yl]-2,2-dimethyl-3a,4,6,6a-tetrahydrofuro[3,4-d][1,3]dioxol-6-yl]methoxy]silane (50b)

To 50% Ethanol (10 mL) was added Na (2.49 mg, 0.11 mmol), until Na was dissolved. The solution was added to triethyl-[(R)-3-bicyclo[4.2.0]octa-1,3,5-trienyl-[(3aR,4R,

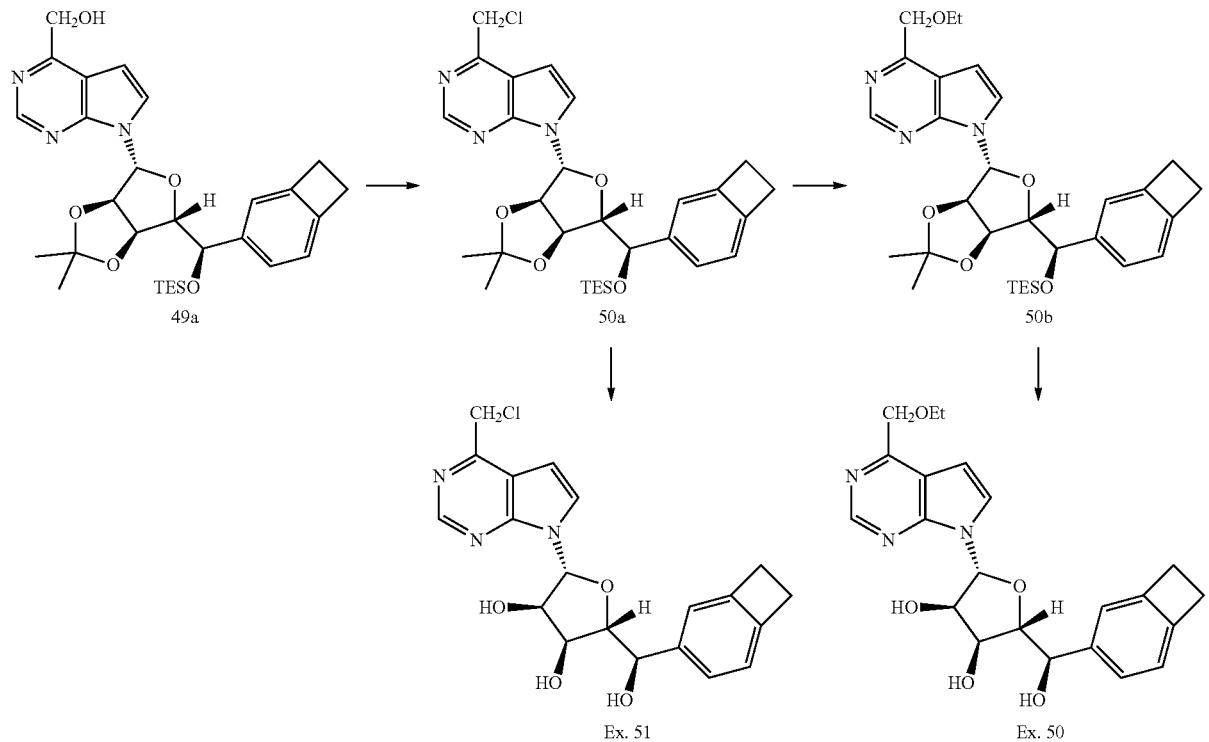

6S,6aR)-4-[4-(chloromethyl)pyrrolo[2,3-d]pyrimidin-7-yl]-2,2-dimethyl-3a,4,6,6a-tetrahydrofuro[3,4-d][1,3]dioxol-6-yl]methoxy]silane (50a) (30.0 mg, 0.05 mmol) in 50% Ethanol (10 mL) under 0° C. The mixture was stirred at 25° C. for 1 h. The mixture was added to a mixture of water (20 ml) and EA (20 ml). Extracted with EA (15 ml*2), washed brine (5 ml), dried by Na₂SO₄, concentrated to give triethyl-[rac-(R)-3-bicyclo[4.2.0]octa-1,3,5-trienyl-[rac-(3aR,4R,6S,6aR)-4-[4-(ethoxymethyl)pyrrolo[2,3-d]pyrimidin-7-yl]-2,2-dimethyl-3a,4,6,6a-tetrahydrofuro[3,4-d][1,3]dioxol-6-yl]methoxy]silane (30 mg, 0.053 mmol, 98% yield) together with unreacted 50a as a yellow oil.

c) Synthesis of (2R,3R,4S,5R)-2-[4-(ethoxymethyl)pyrrolo[2,3-d]pyrimidin-7-yl]-5-[rac-(R)-3-bicyclo[4.2.0]octa-1,3,5-trienyl(hydroxy)methyl]tetrahydrofuran-3,4-diol (Ex. 50) (2R,3R,4S,5R)-2-[4-(chloromethyl)pyrrolo[2,3-d]pyrimidin-7-yl]-5-[rac-(R)-3-bicyclo[4.2.0]octa-1,3,5-trienyl(hydroxy)methyl]tetrahydrofuran-3,4-diol (Ex. 51)

To a solution of TFA (1.0 mL, 13.46 mmol) and Water (1.5 mL) was a mixture of 50a and 50b (30.0 mg, 0.05 mmol), the reaction mixture was stirred at 40° C. for 1 h. LCMS showed the reaction was completed. The mixture was concentrated and purified by prep-HPLC eluting with $CH_3CN/H_2O$ (0.1% $NH_4OH$) from 5/95 to 95/5 to give the prepared solution which was lyophilized to give (2R,3R,4S,5R)-2-[4-(ethoxymethyl)pyrrolo[2,3-d]pyrimidin-7-yl]-5-[rac-(R)-3-bicyclo[4.2.0]octa-1,3,5-trienyl(hydroxy)methyl]tetrahydrofuran-3,4-diol (Ex. 50) (2 mg, 0.0048 mmol, 8.9% yield) as a white solid and (2R,3R,4S,5R)-2-[4-(chloromethyl)pyrrolo[2,3-d]pyrimidin-7-yl]-5-[rac-(R)-3-bicyclo[4.2.0]octa-1,3,5-trienyl(hydroxy)methyl]tetrahydrofuran-3,4-diol (10.1 mg, 0.024 mmol, 45% yield) as a yellow solid.

Ex. 50: $^1H$ NMR (DMSO-d6, 400 MHz) δ 8.75 (s, 1H), 7.84 (s, 1H), 7.21 (d, J=7.6 Hz, 1H), 7.10 (s, 1H), 7.00 (d, J=7.6 Hz, 1H), 6.85 (s, 1H), 6.20 (d, J=8.0 Hz, 1H), 4.83 (s, 2H), 4.73-4.74 (m, 1H), 4.56-4.59 (m, 1H), 4.12-4.13 (m, 1H), 4.01-4.02 (m, 1H), 3.56-3.61 (m, 2H), 3.08 (s, 4H), 1.19-1.23 (m, 3H); (DMSO-d6+$D_2O$, 400 MHz) δ 8.77 (s, 1H), 7.85 (s, 1H), 7.21 (d, J=7.6 Hz, 1H), 7.10 (s, 1H), 7.00 (d, J=7.6 Hz, 1H), 6.87 (s, 1H), 6.20 (d, J=7.6 Hz, 1H), 4.85 (s, 2H), 4.73-4.74 (m, 1H), 4.56-4.59 (m, 1H), 4.12-4.13 (m, 1H), 4.02-4.03 (m, 1H), 3.57-3.62 (m, 2H), 3.09 (s, 4H), 1.20-1.23 (m, 3H).

Ex. 51: $^1HNMR$ (DMSO-d6, 400 MHz) δ 8.80 (s, 1H), 7.92 (s, 1H), 7.21 (d, J=7.6 Hz, 1H), 7.10 (s, 1H), 7.00 (d, J=7.6 Hz, 1H), 6.93 (s, 1H), 6.20 (d, J=8.0 Hz, 1H), 5.01-5.05 (m, 2H), 4.73-4.75 (m, 1H), 4.56-4.59 (m, 1H), 4.12-4.14 (m, 1H), 4.01-4.02 (m, 1H), 3.08 (s, 4H); $^1H$ NMR (DMSO-d6+D2O, 400 MHz) δ 8.80 (s, 1H), 7.92 (s, 1H), 7.21 (d, J=7.6 Hz, 1H), 7.10 (s, 1H), 7.00 (d, J=7.6 Hz, 1H), 6.93 (s, 1H), 6.20 (d, J=8.0 Hz, 1H), 5.01-5.05 (m, 2H), 4.73-4.74 (m, 1H), 4.56-4.59 (m, 1H), 4.12-4.14 (m, 1H), 4.02-4.03 (m, 1H), 3.08 (s, 4H).

TABLE 1

Examples prepared using procedures analogous to those described above.

| Ex. # | Structure | Prepared as in Ex. # | Spectral data |
|---|---|---|---|
| 9 | 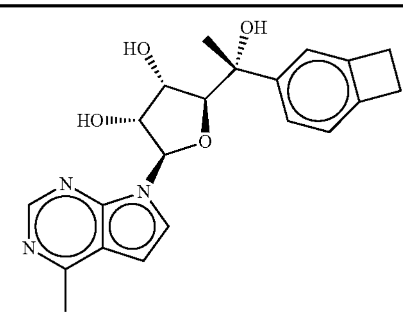 | 11 | $^1H$ NMR (400 MHz, DMSO-$d_6$) δ 8.67 (s, 1H), 7.84 (d, J = 3.7 Hz, 1H), 7.39 (d, J = 7.8 Hz, 1H), 7.26 (s, 1H), 7.05 (d, J = 7.8 Hz, 1H), 6.79 (d, J = 3.7 Hz, 1H), 6.09 (d, J = 8.1 Hz, 1H), 6.04 (s, 1H), 5.17 (d, J = 7.1 Hz, 1H), 4.80 (d, J = 3.6 Hz, 1H), 4.56 (dd, J = 7.7, 12.7 Hz, 1H), 4.11 (s, 1H), 3.73 (t, J = 4.4 Hz, 1H), 3.12 (s, 4H), 2.68 (s, 3H), 1.40 (s, 3H). |
| 14 | 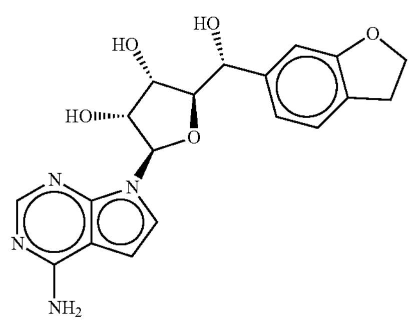 | 1, 2 | LCMS [M + H]: 385.1. $^1H$ NMR (600 Hz, DMSO-d6) δ 8.05 (s, 1H), 7.32 (d, J = 3.6 Hz, 1H), 7.15 (d, J = 7.6 Hz, 1H), 7.08 (s, 2H), 6.86 (d, J = 7.5 Hz, 1H), 6.79 (s, 1H), 6.59 (d, J = 3.6 Hz, 1H), 6.52 (d, J = 3.4 Hz, 1H), 5.89 (d, J = 7.9 Hz, 1H), 5.15 (d, J = 7.1 Hz, 1H), 4.92 (d, J = 3.8 Hz, 1H), 4.73 (t, J = 3.5 Hz, 1H), 4.62 (td, J = 5.0, 7.5 Hz, 1H), 4.50 (t, J = 8.7 Hz, 2H), 4.02 (t, J = 4.4 Hz, 1H), 4.00 (dd, J = 1.0, 4.0 Hz, 1H), 3.13 (t, J = 8.6 Hz, 2H). $^1H$ NMR (600 MHz, DMSO-d6 + $D_2O$) δ 8.03 (s, 1H), 7.29 (d, J = 3.7 Hz, 1H), 7.14 (d, J = 7.6 Hz, 1H), 6.84 (d, J = 7.5 Hz, 1H), 6.75 (s, 1H), 6.58 (d, J = 3.6 Hz, 1H), 5.87 (d, J = 7.9 Hz, 1H), 4.70 (d, J = 4.0 Hz, 1H), 4.59 (dd, J = 5.0, 7.9 Hz, 1H), 4.47 (t, J = 8.7 Hz, 2H), 4.02 (dd, J = 1.1, 5.1 Hz, 1H), 3.99 (dd, J = 0.7, 4.1 Hz, 1H), 3.11 (t, J = 8.7 Hz, 2H). |
| 35 | 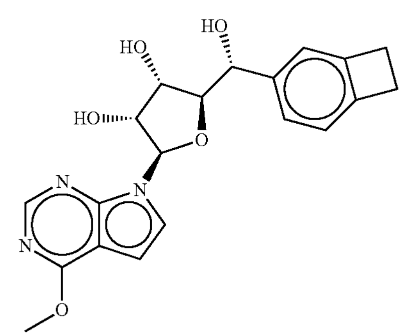 | 2 | $^1H$ NMR (400 MHz, Methanol-d4) δ 8.39 (s, 1H), 7.39 (d, J = 3.6 Hz, 1H), 7.28 (d, J = 7.6 Hz, 1H), 7.16 (s, 1H), 7.02 (d, J = 7.6 Hz, 1H), 6.57 (d, J = 3.6 Hz, 1H), 6.02 (d, J = 7.5 Hz, 1H), 4.96 (d, J = 2.1 Hz, 2H), 4.78 (dd, J = 5.1, 7.4 Hz, 1H), 4.26 (m, 2H), 4.12 (s, 3H), 3.16 (s, 4H). |

TABLE 1-continued

Examples prepared using procedures analogous to those described above.

| Ex. # | Structure | Prepared as in Ex. # | Spectral data |
|---|---|---|---|
| 36 | 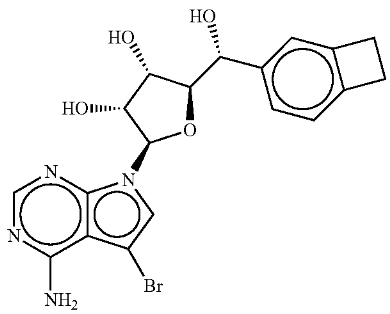 | 6 | LCMS [M + H]: 447.1/449.1. ¹H NMR (400 MHz, DMSO-d6): δ 8.10 (s, 1 H), 7.52 (s, 1 H), 7.21 (d, J = 7.6 Hz, 1 H), 7.11 (s, 1 H), 7.01 (d, J = 7.6 Hz, 1 H), 6.83 (brs, 2 H), 6.07 (d, J = 3.6 Hz, 1 H), 5.99 (d, J = 7.6 Hz, 1 H), 5.24 (d, J = 6.4 Hz, 1 H), 4.99 (d, J = 3.6 Hz, 1 H), 4.72-4.75 (m, 1 H), 4.44-4.49 (m, 1 H), 4.02-4.04 (m, 1 H), 4.00 (d, J = 4.0 Hz, 1 H), 3.10 (s, 4 H).<br>¹H NMR (400 MHz, DMSO-d6 + D₂O): δ 8.11 (s, 1 H), 7.41 (s, 1 H), 7.20 (d, J = 7.6 Hz, 1 H), 7.10 (s, 1 H), 7.03 (d, J = 7.6 Hz, 1 H), 5.99 (d, J = 7.6 Hz, 1 H), 4.74 (d, J = 4.0 Hz, 1 H), 4.43-4.46 (m, 1 H), 4.04-4.07 (m, 2 H), 3.11 (s, 4 H). |
| 37 | 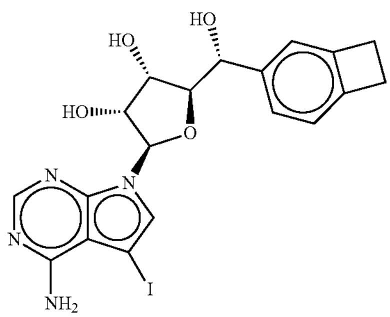 | 6 | LCMS [M + H]: 495.0. ¹H NMR (400 MHz, DMSO-d6): δ 8.10 (s, 1 H), 7.51 (s, 1 H), 7.21 (d, J = 7.2 Hz, 1 H), 7.11 (s, 1 H), 7.02 (d, J = 7.6 Hz, 1 H), 6.70 (brs, 2 H), 6.09 (d, J = 4.0 Hz, 1 H), 5.97 (d, J = 7.6 Hz, 1 H), 5.23 (d, J = 6.8 Hz, 1 H), 4.99 (d, J = 4.0 Hz, 1 H), 4.73-4.75 (m, 1 H), 4.43-4.48 (m, 1 H), 4.00-4.03 (m, 2H), 3.11 (s, 4H).<br>¹H NMR (400 MHz, DMSO-d6 + D₂O): δ 8.11 (s, 1 H), 7.44 (s, 1 H), 7.20 (d, J = 7.6 Hz, 1 H), 7.10 (s, 1 H), 7.03 (d, J = 7.6 Hz, 1 H), 5.97 (d, J = 7.6 Hz, 1 H), 4.74 (d, J = 3.6 Hz, 1 H), 4.42-4.45 (m, 1 H), 4.03-4.05 (m, 2 H), 3.12 (s, 4 H). |
| 38 | 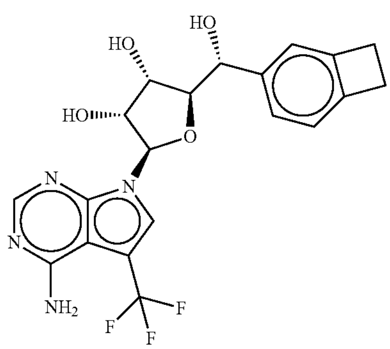 | 6 | LCMS [M + H]: 437.3. ¹H NMR (400 MHz, DMSO-d6): δ 8.26 (s, 1 H), 8.10 (s, 1 H), 7.22 (d, J = 7.2 Hz, 1 H), 7.11 (s, 1 H), 7.01 (d, J = 7.6 Hz, 1H), 6.07 (d, J = 7.6 Hz, 1 H), 4.78 (d, J = 4.0 Hz, 1 H), 4.54-4.58 (m, 1 H), 4.07 (d, J = 4.0 Hz, 1 H), 4.03 (d, J = 4.0 Hz, 1 H), 3.09 (s, 4 H).<br>¹H NMR (400 MHz, DMSO-d6 + D₂O): δ 8.31 (s, 1 H), 8.10 (s, 1 H), 7.21 (d, J = 7.6 Hz, 1 H), 7.11 (s, 1 H), 7.02 (d, J = 7.6 Hz, 1 H), 6.09 (d, J = 7.6 Hz, 1 H), 4.78 (d, J = 3.6 Hz, 1 H), 4.52-4.56 (m, 1 H), 4.09 (d, J = 4.8 Hz, 1 H), 4.06 (d, J = 4.0 Hz, 1 H), 3.10 (s, 4 H).<br>¹⁹F NMR (376 MHz, DMSO-d6): δ −53.74 (s, 3 F) |
| 39 | 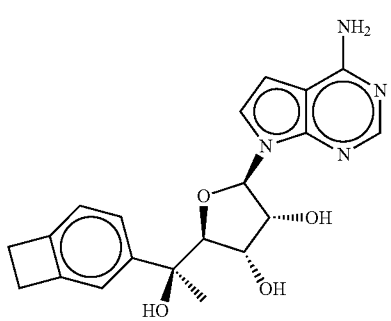 | 1 | ¹H NMR (500 MHz, DMSO-d6 + D₂O) δ 8.07 (s, 1H), 7.25 (dd, J = 1.5, 7.8 Hz, 1H), 7.14 (d, J = 3.6 Hz, 1H), 7.10 (s, 1H), 6.90 (d, J = 7.8 Hz, 1H), 6.51 (d, J = 3.5 Hz, 1H), 5.68 (d, J = 7.8 Hz, 1H), 4.40 (dd, J = 5.3, 7.8 Hz, 1H), 4.24-4.18 (m, 2H), 3.01 (s, 4H), 1.38 (s, 3H). |

TABLE 1-continued

Examples prepared using procedures analogous to those described above.

| Ex. # | Structure | Prepared as in Ex. # | Spectral data |
|---|---|---|---|
| 42 | 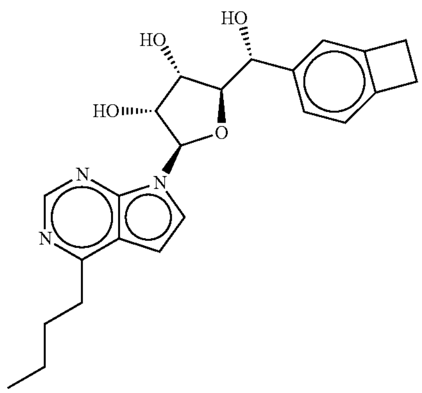 | 11 | 1H NMR (400 MHz, DMSO-d6): δ 8.72 (s, 1 H), 7.79-7.80 (d, J = 3.6 Hz, 1 H), 7.20-7.22 (m, 1 H), 7.10 (s, 1 H), 7.00-7.01 (m, 1 H), 6.82-6.83 (d, J = 3.6 Hz, 1 H), 6.15-6.17 (d, J = 8.00 Hz, 1 H), 5.94 (s, 1 H), 5.28 (s, 1 H), 5.08 (s, 1 H), 4.73-4.74 (d, J = 4.8 Hz, 1 H), 4.57-4.60(m, 1 H), 4.11-4.12 (d, J = 4.8 Hz, 1 H), 4.01-4.02 (d, J = 4.4 Hz, 1 H), 3.09 (m, 4 H), 2.98-3.02 (m, 2 H), 1.72-1.78 (m, 2 H), 1.31-1.37 (m, 2 H), 0.89-0.93 (m, 3 H) <br> 1H NMR (400 MHz, DMSO-d6 + D$_2$O): δ 8.71 (s, 1 H), 7.77-7.78 (d, J = 4.0 Hz, 1 H), 7.20-7.22 (m, 1 H), 7.10 (s, 1 H), 7.00-7.02 (m, 1 H), 6.83 (d, J = 3.6 Hz, 1 H), 6.15-6.17 (d, J = 7.6 Hz, 1 H), 4.73-4.74 (m, 1 H), 4.57-4.60 (m, 1 H), 4.12-4.13 (d, J = 3.6 Hz, 1 H), 4.02-4.03 (d, J = 4.8 Hz, 1 H), 3.09 (m, 4 H), 2.98-3.02 (m, 2 H), 1.72-1.78 (m, 2 H), 1.31-1.37 (m, 2 H), 0.89-0.93 (m, 3 H) |
| 44 | 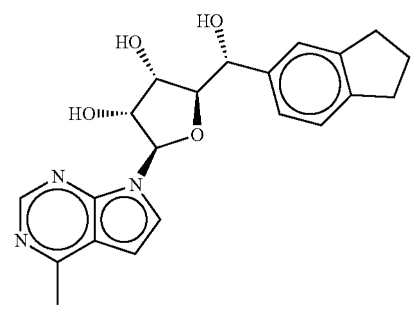 | 11 | LCMS [M + H]: 382.0. $^1$H NMR (500 MHz, DMSO-d6) δ 8.69 (s, 1H), 7.79 (d, J = 3.5 Hz, 1H), 7.29 (s, 1H), 7.18 (s, 2H), 6.81 (d, J = 3.5 Hz, 1H), 6.19 (d, J = 7.8 Hz, 1H), 5.97 (d, J = 3.5 Hz, 1H), 5.26 (d, J = 6.8 Hz, 1H), 5.16-5.02 (m, 1H), 4.79 (s, 1H), 4.62 (q, J = 6.8 Hz, 1H), 4.15 (s, 1H), 4.07 (d, J = 4.2 Hz, 1H), 2.85 (t, J = 7.2 Hz, 4H), 2.70 (s, 3H), 2.03 (p, J = 7.2 Hz, 2H). |
| 45 | 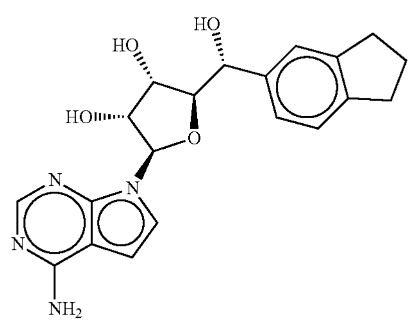 | 2 | LCMS [M + H]: 383.0. $^1$H NMR (500 MHz, DMSO-d6) δ 8.09 (s, 1H), 7.39-7.26 (m, 2H), 7.26-7.08 (m, 4H), 6.63 (d, J = 3.5 Hz, 1H), 6.56 (d, J = 2.6 Hz, 1H), 5.94 (d, J = 7.9 Hz, 1H), 5.20 (d, J = 7.1 Hz, 1H), 4.96 (d, J = 3.7 Hz, 1H), 4.80 (s, 1H), 4.66 (q, J = 7.4 Hz, 1H), 4.15-4.05 (m, 2H), 2.93-2.79 (m, 4H), 2.04 (p, J = 7.3 Hz, 2H). |
| 46 | 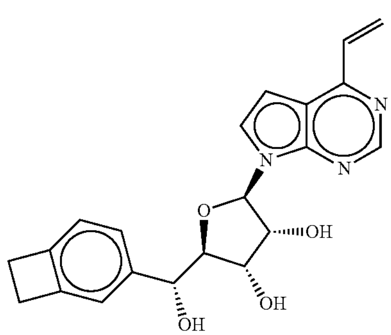 | 40 | 1HNMR (DMSO-d6 + D$_2$O, 400 MHz): δ 8.75 (s, 1H), 7.83-7.84 (m, 1H), 7.19-7.26 (m, 2H), 7.10 (s, 1H), 6.96-7.01 (m, 2H), 6.61-6.66 (m,1H), 6.17-6.19 (m,1H), 5.82-5.85 (m,1H), 4.73-4.74 (m,1H), 4.57-4.60 (m,1H), 4.12-4.14 (m,1H), 4.02-4.04 (m,1H), 3.06-3.10 (m, 4H) |

TABLE 1-continued

Examples prepared using procedures analogous to those described above.

| Ex. # | Structure | Prepared as in Ex. # | Spectral data |
|---|---|---|---|
| 47 | 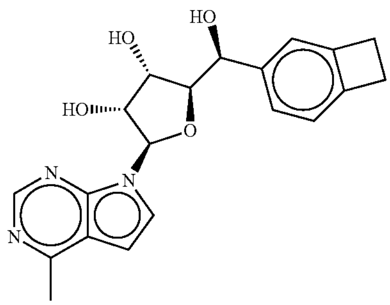 | 11 | LCMS [M + H]: 368.2. ¹H NMR (400 MHz, DMSO-d6) δ8.92 (s, 1 H), 8.11-8.12 (d, J = 3.6 Hz, 1 H), 7.17-7.19 (d, J = 7.2 Hz,1H), 7.07-7.08 (d, J = 3.2 Hz, 2 H), 6.98-7.00 (d, J = 7.2 Hz, 1 H), 6.20-6.21(d, J = 6.4 Hz,1H), 4.79-4.80(d, J = 3.2 Hz, 1 H), 4.37-4.40 (m, 1 H), 4.15-4.17 (m, 1 H), 44.07-4.08 (m, 1 H), 3.07 (s, 4 H), 2.81 (s, 3 H).<br>¹H NMR (400 MHz, DMSO-d6 + D2O) δ8.98(s,1H), 8.21 (s, 1 H), 7.18 (s,2H), 7.08 (s,1H), 6.99-7.01 (d, J = 7.6 Hz,1H), 6.23-6.24 (d, J = 6.8 Hz, 1 H), 4.71(s,1H), 4.40-4.43 (m,1H), 4.20 (s, 1 H), 4.11(s, 1 H), 3.06 (s,4H), 2.87 (s, 3 H). |
| 52 | 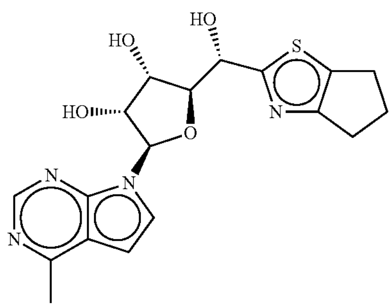 | 11 | LCMS [M + H]: 389.0. ¹H NMR (500 MHz, DMSO-d6) δ 8.65 (s, 1H), 7.66 (d, J = 3.7 Hz, 1H), 6.91 (d, J = 4.9 Hz, 1H), 6.77 (d, J = 3.7 Hz, 1H), 6.17 (d, J = 7.5 Hz, 1H), 5.29 (d, J = 6.9 Hz, 1H), 5.13 (d, J = 4.3 Hz, 1H), 5.03-4.90 (m, 1H), 4.53 (td, J = 5.0, 7.2 Hz, 1H), 4.30 (dd, J = 1.5, 3.4 Hz, 1H), 4.15-4.01 (m, 1H), 2.83 (t, J = 7.2 Hz, 2H), 2.72 (t, J = 6.9 Hz, 2H), 2.65 (s, 3H), 2.41 (p, J = 7.2 Hz, 2H). |
| 53 | 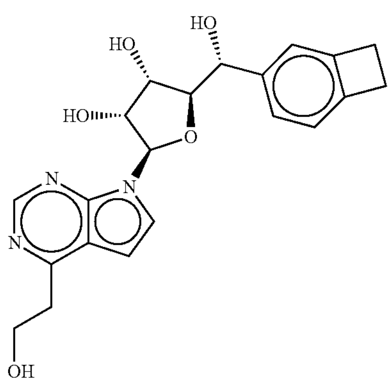 | 48 | ¹H NMR (400 MHz, DMSO-d6 + D2O): δ 8.69 (s, 1H), 7.74-7.75 (m, 1H), 7.20-7.22 (m, 1H), 7.10 (s, 1H), 7.00-7.01 (m, 1H), 6.78-6.79 (m, 1H), 6.14-6.16 (m, 1H), 4.73-4.74 (m, 1H), 4.56-4.60 (m, 1H), 4.11-4.12 (m, 1H), 4.01-4.03 (m, 1H), 3.84-3.88 (m, 2H), 3.12-3.15 (m, 2H), 3.06-3.10 (m, 4H) |
| 54 | 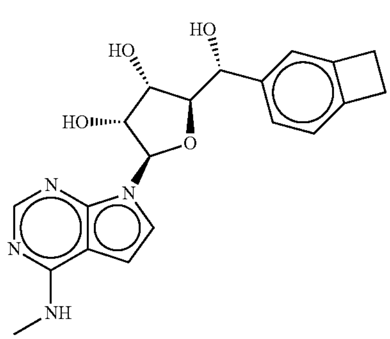 | 2 | LCMS [M + H]: 383.1. ¹H NMR (400 MHz, DMSO-d6 + D2O) δ8.14(s,1H), 7.30 (d, J = 3.6 Hz,1H), 7.22 (d, J = 7.6 Hz,1H), 7.11(s,1H),7.03 (d, J = 7.6 Hz,1H), 6.58 (d, J = 3.6 Hz, 1 H), 5.91 (d, J = 7.6 Hz, 1 H), 4.75(d, J = 4.0 Hz,1H), 4.60-4.63 (m,1H), 4.03-4.06 (m, 2 H), 3.10 (s,4H), 2.96 (s, 3 H). |

TABLE 1-continued

Examples prepared using procedures analogous to those described above.

| Ex. # | Structure | Prepared as in Ex. # | Spectral data |
|---|---|---|---|
| 55 | 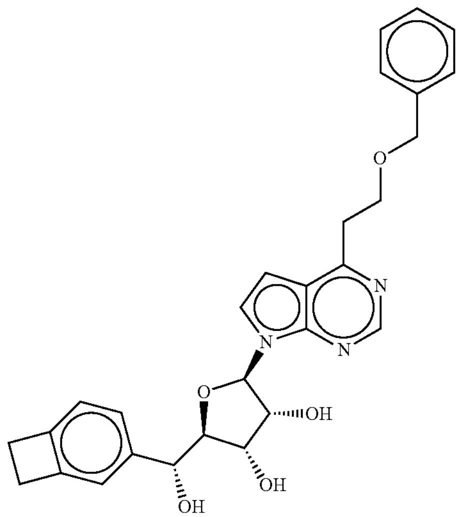 | 48 | $^1$H NMR (400 MHz, DMSO-d$_6$ + D$_2$O): δ 8.69 (s, 1H), 7.75-7.76 (m, 1H), 7.29-7.33 (m, 2H), 7.20-7.27 (m, 4H), 7.10 (s, 1H), 7.00-7.01 (m, 1H), 6.82-6.83 (m, 1H), 6.15-6.17 (m, 1H), 4.73-4.74 (m, 1H), 4.56-4.60 (m, 1H), 4.48 (s, 2H), 4.11-4.12 (m, 1H), 4.01-4.03 (m, 1H), 3.91-3.94 (m, 2H), 3.26-3.29 (m, 2H), 3.06-3.10 (m, 4H). |
| 56 | 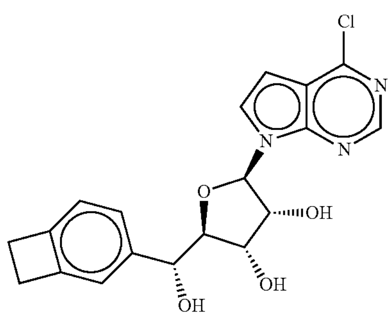 | 2 | LCMS [M + H]: 388.3. $^1$H NMR (400 MHz, DMSO-d6) δ 8.66 (s, 1 H), 7.98 (d, J = 3.6 Hz,1H), 7.20 (d, J = 7.2 Hz,1H), 7.10 (s, 1 H), 7.00 (d, J = 7.6 Hz,1H), 6.78 (d, J = 3.6 Hz,1H), 6.20 (d, J = 7.6 Hz,1H), 5.82 (s, 1 H), 5.31(s, 1 H), 5.10 (s, 1 H), 4.74 (s, 1 H), 4.55-4.58 (m, 1 H), 4.14 (d, J = 3.6 Hz,1H), 4.03 (d, J = 4.4 Hz,1H), 3.08 (s, 4 H). $^1$H NMR (400 MHz, DMSO-d6 + D2O) δ8.66(s,1H), 7.92 (d, J = 4.0 Hz,1H), 7.20 (d, J = 7.6 Hz,1H), 7.09(s,1H),7.00 (d, J = 7.2 Hz,1H), 6.78 (d, J = 3.6 Hz, 1 H), 6.19 (d, J = 7.2 Hz, 1 H), 4.73(d, J = 4.8 Hz, 1H), 4.55-4.59 (m,1H), 4.16 (d, J = 4.8 Hz, 1 H), 4.05 (d, J = 4.8 Hz, 1 H), 3.09 (s, 4 H). |

X-Ray Structure Determination of Example 11

Compound of Example 11 was recrystallized from ethanol. Crystals suitable for X-ray diffraction studies were obtained as clear colorless prisms. A clear colourless block-like specimen of C$_{20}$H$_{21}$N$_3$O$_4$, approximate dimensions 0.071 mm×0.081 mm×0.353 mm, was used for the X-ray crystallographic analysis. Table 1 shows crystal data details.

The total exposure time was 20.12 hours. The frames were integrated with the Bruker SAINT software package using a narrow-frame algorithm. The integration of the data using an orthorhombic unit cell yielded a total of 20159 reflections to a maximum θ angle of 75.420 (0.80 Å resolution), of which 3565 were independent (average redundancy 5.655, completeness=99.8%, R$_{int}$=5.73%, R$_{sig}$=5.24%) and 3401 (95.40%) were greater than 2σ(F$^2$). The final cell constants of a=7.7138(3) Å, b=13.4258(6) Å, c=16.6573(7) Å, volume=1725.10(13) Å$^3$, are based upon the refinement of the XYZ-centroids of 9173 reflections above 20 σ(I) with 8.458°<2θ<150.7°. Data were corrected for absorption effects using the Multi-Scan method (SADABS). The ratio of minimum to maximum apparent transmission was 0.843. The calculated minimum and maximum transmission coefficients (based on crystal size) are 0.7600 and 0.9440.

FIG. 1 show an ORTEP representation of the compound of Example 11. The structure was solved and refined using the Bruker SHELXTL Software Package, using the space group P 21 21 21, with Z=4 for the formula unit, C$_{20}$H$_{21}$N$_3$O$_4$. The final anisotropic full-matrix least-squares refinement on F$^2$ with 328 variables converged at R1=3.27%, for the observed data and wR2=9.03% for all data. The goodness-of-fit was 1.113. The largest peak in the final difference electron density synthesis was 0.235 e$^-$/Å$^3$ and the largest hole was −0.165 e$^-$/Å$^3$ with an RMS deviation of 0.039 e$^-$/Å$^3$. On the basis of the final model, the calculated density was 1.415 g/cm$^3$ and F(000), 776 e$^-$.

TABLE 2

Sample and crystal data for compound of Example 11

| | |
|---|---|
| Chemical formula | C$_{20}$H$_{21}$N$_3$O$_4$ |
| Chemical formula | C20H21N3O4 |
| Formula weight | 367.40 g/mol |
| Temperature | 200(2) K |
| Wavelength | 1.54178 Å |
| Crystal size | 0.071 × 0.081 × 0.353 mm |
| Crystal system | orthorhombic |
| Space group | P 21 21 21 |
| Unit cell dimensions | a = 7.7138(3) Å α = 90° |
| b = 13.4258(6) Å | β = 90° |
| c = 16.6573(7) Å | γ = 90° |
| Volume | 1725.10(13) Å3 |
| Z | 4 |
| Density (calculated) | 1.415 g/cm3 |
| Absorption coefficient | 0.822 mm−1 |
| F(000) | 776 |

Additional information on the crystal structure of compound of Example 11 is listed in Tables 3 to 6.

TABLE 3

Data collection and structure refinement for compound of Example 11

| | |
|---|---|
| Theta range for data collection | 4.23 to 75.42° |
| Index ranges | −9 <= h <= 9, −16 <= k <= 16, −20 <= l <= 20 |
| Reflections collected | 20159 |
| Independent reflections | 3565 [R(int) = 0.0573] |
| Coverage of independent reflections | 99.8% |
| Absorption correction | Multi-Scan |
| Max. and min. transmission | 0.9440 and 0.7600 |
| Structure solution technique | direct methods |
| Structure solution program | SHELXT 2014/5 (Sheldrick, 2014) |
| Refinement method | Full-matrix least-squares on F2 |
| Refinement program | SHELXL-2017/1 (Sheldrick, 2017) |
| Function minimized | Σ w(Fo2 − Fc2)2 |
| Data/restraints/parameters | 3565/0/328 |
| Goodness-of-fit on F2 | 1.113 |
| Final R indices | 3401 data; I > 2σ(I)R1 = 0.0327, wR2 = 0.0893 |
| | all data R1 = 0.0341, wR2 = 0.0903 |
| Weighting scheme where P = (Fo2 + 2Fc2)/3 | w = 1/[σ2(Fo2) + (0.0456P)2 + 1.1670P] |
| Absolute structure parameter | −0.02(12) |
| Largest diff. peak and hole | 0.235 and −0.165 eÅ−3 |
| R.M.S. deviation from mean | 0.039 eÅ−3 |

TABLE 4

Atomic coordinates and equivalent isotropic atomic displacement parameters (Å$^2$) for compound of Example 11

| | x/a | y/b | z/c | U(eq) |
|---|---|---|---|---|
| O1 | 0.35067(19) | 0.51192(11) | 0.50048(9) | 0.0239(3) |
| O2 | 0.7564(2) | 0.56138(12) | 0.52052(9) | 0.0255(3) |
| O3 | 0.6275(2) | 0.69670(10) | 0.41234(9) | 0.0220(3) |
| O4 | 0.0702(2) | 0.65445(13) | 0.48013(11) | 0.0313(4) |
| N1 | 0.4819(2) | 0.36100(13) | 0.46699(10) | 0.0224(4) |
| N2 | 0.4867(2) | 0.39430(12) | 0.32441(10) | 0.0217(4) |
| N3 | 0.4028(2) | 0.25394(14) | 0.24387(11) | 0.0256(4) |
| C1 | 0.4433(3) | 0.27695(16) | 0.51247(13) | 0.0281(5) |
| C2 | 0.4023(3) | 0.19886(16) | 0.46548(13) | 0.0288(5) |
| C3 | 0.4108(3) | 0.23408(15) | 0.38424(13) | 0.0222(4) |
| C4 | 0.3806(3) | 0.19501(15) | 0.30821(13) | 0.0232(4) |
| C5 | 0.4557(3) | 0.34869(16) | 0.25531(13) | 0.0245(4) |
| C6 | 0.4617(3) | 0.33532(14) | 0.38774(12) | 0.0196(4) |
| C7 | 0.3210(4) | 0.09047(18) | 0.29500(16) | 0.0341(5) |
| C8 | 0.5105(3) | 0.45907(15) | 0.50091(12) | 0.0200(4) |
| C9 | 0.6481(3) | 0.52374(15) | 0.45895(11) | 0.0191(4) |
| C10 | 0.5383(2) | 0.60494(14) | 0.41844(11) | 0.0174(4) |
| C11 | 0.3763(3) | 0.61100(14) | 0.47102(11) | 0.0193(4) |
| C12 | 0.2135(3) | 0.64621(16) | 0.42613(13) | 0.0223(4) |
| C13 | 0.1624(3) | 0.57846(16) | 0.35770(12) | 0.0217(4) |
| C14 | 0.0761(2) | 0.48835(16) | 0.37308(12) | 0.0227(4) |
| C15 | 0.0377(3) | 0.43064(16) | 0.30696(13) | 0.0237(4) |
| C16 | 0.9541(3) | 0.33320(18) | 0.28065(15) | 0.0302(5) |
| C17 | 0.0003(3) | 0.36463(18) | 0.19238(14) | 0.0320(5) |
| C18 | 0.0817(3) | 0.45753(18) | 0.22887(13) | 0.0268(4) |
| C19 | 0.1695(3) | 0.54464(19) | 0.21257(13) | 0.0289(5) |
| C20 | 0.2071(3) | 0.60495(17) | 0.27913(13) | 0.0254(4) |

U(eq) is defined as one third of the trace of the orthogonalized Uij tensor

TABLE 5

Bond lengths (Å) for compound of Example 11

| | | | | | |
|---|---|---|---|---|---|
| O1—C8 | 1.422(2) | | | O1—C11 | 1.432(2) |
| O2—C9 | 1.416(2) | | | O2—H1 | 0.83(4) |
| O3—C10 | 1.415(2) | | | O3—H2 | 0.83(3) |
| O4—C12 | 1.429(2) | | | O4—H3 | 0.90(3) |
| N1—C6 | 1.373(3) | | | N1—C1 | 1.392(3) |
| N1—C8 | 1.450(3) | | | N2—C5 | 1.325(3) |
| N2—C6 | 1.333(3) | | | N3—C4 | 1.343(3) |
| N3—C5 | 1.350(3) | | | C1—C2 | 1.346(3) |
| C1—H4 | 0.99(3) | | | C2—C3 | 1.435(3) |
| C2—H5 | 1.03(3) | | | C3—C4 | 1.390(3) |
| C3—C6 | 1.416(3) | | | C4—C7 | 1.493(3) |
| C5—H6 | 1.03(3) | | | C7—H7 | 0.96(4) |
| C7—H8 | 0.96(4) | | | C7—H9 | 0.95(5) |
| C8—C9 | 1.539(3) | | | C8—H10 | 0.96(2) |
| C9—C10 | 1.537(3) | | | C9—H11 | 0.99(3) |
| C10—C11 | 1.528(3) | | | C10—H12 | 0.98(2) |
| C11—C12 | 1.536(3) | | | C11—H13 | 0.96(3) |
| C12—C13 | 1.511(3) | | | C12—H14 | 1.00(2) |
| C13—C20 | 1.399(3) | | | C13—C14 | 1.404(3) |
| C14—C15 | 1.379(3) | | | C14—H15 | 0.97(3) |
| C15—C18 | 1.392(3) | | | C15—C16 | 1.523(3) |
| C16—C17 | 1.571(3) | | | C16—H16 | 0.98(3) |
| C16—H17 | 0.98(3) | | | C17—C18 | 1.523(3) |
| C17—H18 | 1.01(4) | | | C17—H19 | 0.99(3) |
| C18—C19 | 1.379(3) | | | C19—C20 | 1.403(3) |
| C19—H20 | 0.96(3) | | | C20—H21 | 0.97(3) |

TABLE 6

Hydrogen atomic coordinates and isotropic atomic displacement parameters (Å2) for compound of Example 11

| | x/a | y/b | z/c | U(eq) |
|---|---|---|---|---|
| H1 | 0.831(5) | 0.597(3) | 0.4992(19) | 0.047(9) |
| H2 | 0.628(5) | 0.715(2) | 0.365(2) | 0.039(8) |
| H3 | 0.085(4) | 0.704(2) | 0.5158(17) | 0.029(7) |
| H4 | 0.453(4) | 0.280(2) | 0.5714(17) | 0.037(8) |
| H5 | 0.374(4) | 0.127(2) | 0.4831(17) | 0.037(7) |
| H6 | 0.471(4) | 0.389(2) | 0.2034(15) | 0.026(6) |
| H7 | 0.307(4) | 0.055(3) | 0.344(2) | 0.049(9) |
| H8 | 0.404(5) | 0.054(3) | 0.263(2) | 0.057(10) |
| H9 | 0.213(6) | 0.087(3) | 0.267(3) | 0.085(14) |
| H10 | 0.546(3) | 0.4494(17) | 0.5555(13) | 0.013(5) |
| H11 | 0.717(4) | 0.484(2) | 0.4205(17) | 0.030(7) |
| H12 | 0.505(3) | 0.5811(16) | 0.3651(13) | 0.009(5) |
| H13 | 0.397(4) | 0.657(2) | 0.5144(15) | 0.024(6) |
| H14 | 0.237(3) | 0.7155(18) | 0.4062(13) | 0.015(5) |
| H15 | 0.049(3) | 0.469(2) | 0.4275(16) | 0.023(6) |
| H16 | 0.004(4) | 0.272(2) | 0.3028(16) | 0.028(7) |
| H17 | −0.170(5) | 0.329(3) | 0.2927(19) | 0.044(9) |
| H18 | 0.088(5) | 0.319(3) | 0.1660(19) | 0.052(9) |

TABLE 6-continued

Hydrogen atomic coordinates and isotropic atomic displacement parameters (Å2) for compound of Example 11

| | x/a | y/b | z/c | U(eq) |
|---|---|---|---|---|
| H19 | −0.098(4) | 0.376(2) | 0.1548(17) | 0.039(8) |
| H20 | 0.203(4) | 0.561(2) | 0.1587(18) | 0.031(7) |
| H21 | 0.269(4) | 0.667(2) | 0.2701(18) | 0.036(7) |

Biochemical Assay Protocol

HotSpot Assay. Compounds were solubilized and 3-fold diluted in 100% DMSO. These diluted compounds were further diluted in the assay buffer (50 mM Tris-HCl, pH 8.5, 50 mM NaCl, 5 mM MgCl2, 0.01% Brij35, 1 mM DTT, 1% DMSO) for 10-dose $IC_{50}$ mode at a concentration 10-fold greater than the desired assay concentration. Standard reactions were performed in a total volume of 50 µl in assay buffer, with histone H2A (5 µM final) as substrate. To this was added the PRMT5/MEP50 complex diluted to provide a final assay concentration of 5 nM and the compounds were allowed to preincubate for 15 to 20 minutes at room temperature. The reaction was initiated by adding S-[3H-methyl]-adenosyl-L-methionine (PerkinElmer) to final concentration of 1 µM. Following a 60 minutes incubation at 30° C., the reaction was stopped by adding 100 µL of 20% TCA. Each reaction was spotted onto filter plate (Multi-Screen FB Filter Plate, Millipore), and washed 5 times with PBS buffer, Scintillation fluid was added to the filter plate and read in a scintillation counter. $IC_{50}$ values were determined by fitting the data to the standard 4 parameters with Hill Slope using GraphPad Prism software. This procedure generated the HotSpot data in Table 7.

Flash plate assay. Compounds were solubilized, and 3-fold diluted in 100% DMSO. These diluted compounds were further diluted in the assay buffer (20 mM Tris-HCl, pH 8.0, 50 mM NaCl, 0.002% Tween20, 1 mM TCEP, 1% DMSO) for 10-dose IC50 mode at a concentration 10-fold greater than the desired assay concentration. Standard reactions were performed in a total volume of 30 µl in assay buffer, with 300 nM histone H4 based AcH4-23 (Anaspec: AS-65002) as substrate. To this was added the PRMT5/MEP50 complex diluted to provide a final assay concentration of 2.5 nM and the compounds were allowed to preincubate for 20 minutes at 37° C. The reaction was initiated by adding S-[3H-methyl]-adenosyl-L-methionine (PerkinElmer: NET155001MC) to final concentration of 1 µM. Following a 30 minutes incubation at 37° C., the reaction was stopped by adding 25 µL of 8M Guanidine HCl. Prepare streptavidin YSI SPA beads (Perkinelmer: RPNQ0012) at 0.3 mg/mL in assay buffer. To each reaction, add 150 µL of SPA beads suspension, and incubated while shaking at room temperature for 30 minutes. The plate was centrifuged at 100×g for 30 second before reading in a scintillation counter. IC50 values were determined by fitting the data to the standard 4 parameters with Hill Slope using GraphPad Prism software. This procedure produced the Flash Plate data in Table 7.

Cellular Assay Protocol

Cell Treatment and Western Blotting for Detecting Symmetric Di-Methyl Arginine (sDMA) and Histone H3R8 Dimethyl Symmetric (H3R8me2s) Marks Initial compounds screening in A549 cells: Compounds can be dissolved in DMSO to make 10 mM stock and can be further diluted to 0.1, and 1 mM. A549 cells are maintained in PRMI 1640 (Corning Cellgro, Catalog #: 10-040-CV) medium supplemented with 10% v/v FBS (GE Healthcare, Catalog #: SH30910.03). One day before experiment, 1.25× $10^5$ cells are seeded in 6 well plate in 3 mL medium and incubated overnight. The next day, medium is changed and 3 uL of compound solution is added (1:1,000 dilution, 0.1 and 1 uM final concentration; DMSO concentration: 0.1%), and incubated for 3 days. Cells incubated with DMSO are used as a vehicle control. Cells are washed once with PBS, trypsinized in 150 uL 0.25% Trypsin (Corning, Catalog #: 25-053-CI), neutralized with 1 mL complete medium, transferred to microCentrifuge tubes and collected. Cell pellet are then resuspended in 15 uL PBS, lysed in 4% SDS, and homogenized by passing through homogenizer column (Omega Biotek, Catalog #: HCR003). Total protein concentrations are determined by BCA assay (ThermoFisher Scientific, Catalog #: 23225). Lysates are mixed with 5× Laemmli buffer and boiled for 5 min. Forty ug of total protein is separated on SDS-PAGE gels (Bio-Rad, catalog #: 4568083, 4568043), transferred to PVDF membrane, blocked with 5% dry milk (Bio-Rad, Catalog #: 1706404) in TBS with 0.1% v/v Tween 20 (TBST) for 1 hour at room temperature (RT), and incubated with primary antibodies (sDMA: Cell signaling, Catalog #: 13222, 1:3,000; H3R8me2s: Epigentek, Catalog #: A-3706-100, 1:2,000; β-Actin: Abcam, Catalog #: ab8227, 1:10,000) in 5% dry milk in TBST at 4° C. for overnight. The next day, membranes are washed with TBST, 5×5 min, and incubated with HRP conjugated seconded antibody (GE Healthcare; Catalog #: NA934-1ML; 1:5,000) for 2 hours at RT, followed by 5×5 min washes with TBST, and incubation with ECL substrates (Bio-Rad, Catalog #: 1705061, 1705062). Chemiluminescent signal is captured with Fluochem HD2 imager (Proteinsimple) and analyzed by ImageJ.

To determine enzyme inhibition $IC_{50}$ values using Western Blot analysis, Granta cells can be seeded at density of 5×$10^5$ cells/mL in 3 mL medium (PRMI+10% v/v FBS). Nine-point 3-fold serial dilutions of compound are added to cells (3 ul, 1:1,000 dilution, DMSO concentration was 0.1%; final top concentration was 10 or 1 uM, depending on compounds potency) and incubated for 3 days. Cells incubated with DMSO are used as a vehicle control. Cells are harvested and subjected to western blot analysis as described above. SmD3me2s and H3R8me2s bands can be quantified by ImageJ. Signals can be normalized to β-Actin and DMSO control. $IC_{50}$ values can be calculated using Graphpad Prism.

Cell Treatment and Western Blotting for Detecting Symmetric Di-Methyl Arginine (sDMA) Marks (in Granta-519 and U-87 MG Cell Lines)

Compound titration and cell culture: Compounds were dissolved in DMSO to make 10 mM stock and 3-fold series dilutions were further conducted to make working stocks top at 1 mM. Granta-519 cells were maintained in PRMI 1640 (Corning Cellgro, Catalog #: 10-040-CV) supplemented with 10% v/v FBS (GE Healthcare, Catalog #: SH30910.03) and U-87 MG cells were maintained in DMEM (Corning Cellgro, Catalog #: 10-013-CV) with 10% FBS and 2 mM Glutamin (Corning Cellgro, Catalog #25005CV).

To determine enzyme inhibition $IC_{50}$ values in Granta-519 and U-87 MG cells using Western Blot analysis. One day before experiment, Granta-519 cells were passaged to a density of 0.5×$10^6$ cells/ml. U-87 MG cells were trypsinized and 4×$10^5$ cells were seeded into 6-well plates and allow to grow overnight. The next day, Granta-519 cells were spun down at 1,500 rpm for 4 min, resuspend in fresh medium at 0.5×$10^6$ cells/ml and 3 mL of culture (1.5×$10^6$ cells) were seeded into 6 well plate. Eight-point, 3-fold serial dilutions of compound working stocks were added to cells (3 ul, 1:1,000 dilution, DMSO concentration was 0.1%; final top concentration at 1 uM) and incubated for 3 days. Cells incubated with DMSO was used as a vehicle control.

Cells were harvested 3 days later, resuspended in 15 uL PBS, lysed in 4% SDS, and homogenized by passing through homogenizer column (Omega Biotek, Catalog #: HCR003). Total protein concentrations were determined by BCA assay (ThermoFisher Scientific, Catalog #: 23225). Lysates were mixed with 5× Laemmli buffer and boiled for 5 min. Forty ug of total protein was separated on SDS-PAGE gels (Bio-Rad, catalog #: 4568083, 4568043), transferred to PVDF membrane, blocked with 5% dry milk (Bio-Rad, Catalog #: 1706404) in TBS with 0.1% v/v Tween 20 (TBST) for 1 hour at room temperature (RT), and incubated with primary antibodies (sDMA: Cell signaling, Catalog #: 13222, 1:3,000; β-Actin: sigma, Catalog #: 1:5,000) in 5% dry milk in TBST at 4° C. overnight. The next day, membranes were washed with TBST, 5×5 min, and incubated with HRP conjugated seconded antibody (GE Healthcare; Catalog #: NA934-1ML, NA931-1ML; 1:5,000) for 2 hours at RT, followed by 5×5 min washes with TBST, and incubation with ECL substrates (Bio-Rad, Catalog #: 1705061, 1705062). Chemiluminescent signal was captured with Fluochem HD2 imager (Proteinsimple). SmD3me2s bands were quantified by ImageJ. Signals were normalized to β-Actin and DMSO control. $IC_{50}$ values were calculated using Graphpad Prism ([Inhibitor]vs. normalized response–Variable slope).

sDMA In Cell Western procedure (ICW): Granta-519 cells were passaged to a density of $0.5 \times 10^6$ cells/ml one day before experiments and allowed to grow overnight. The next day (day 0), cells were spun down at 1,500 rpm for 4 min, resuspended in fresh medium to $0.2 \times 10^6$ cells/ml and 100 uL of cells were added to 384-well plates using a Multidrop Combi Dispenser (ThermoFisher). A series of 9-point, 3-fold serial dilutions of compounds were prepared and dispensed into wells from a 1 mM stock solution using a TECAN digital dispenser (D300e) and the DMSO % concentration was normalized in each well to 0.1%. DMSO and 3 uM of reference compounds were used as negative (minimum inhibition) and positive (maximum inhibition) controls, respectively. After 3 days of incubation, cells were first resuspended and then 80 ul of cells were transferred to a Poly-D-lysine 384-well plate (Corning, Catalog #354663), followed by 30 minutes incubation at room temperature (RT) and 5 additional hours of incubation at 37° C. Cells were then fixed with 4% paraformaldehyde (Electron Microscopy, Catalog #15710) for 30 minutes at RT and permeabilized by washing the plate 5 times with 50 ul/well of wash buffer (1×PBS with 0.1% Triton X-100), blocked with 30 ul/well of Odyssey blocking buffer (Li—COR, Catalog #927-40000) for 1 hour at RT with gentle rocking, and incubated with 20 ul/well of primary antibody (sDMA: Cell signaling, Catalog #: 13222, 1:800 in Odyssey blocking buffer) overnight at 4° C. The following day, cells were washed 5 times with 50 ul/well of wash buffer, incubated with 20 ul/well of secondary antibody (800CW goat anti-rabbit IgG (H+L), Li—COR, Catalog #926-32211, 1:500; DRAQ5 (Abcam, Catalog #ab108410), 1:1000; in Odyssey blocking buffer) for 1 hour at RT, washed again 5 times with 50 ul/well wash buffer, followed by 1 last wash with water. The plate was left to dry at RT and scanned on Licor Odyssey CLx imaging system to acquire integrated intensities at 700 nm and 800 nm channels.

U87-MG cells were trypsinized one day before the experiment, seeded into a 384-well plate at 2500 cells/well using a Multidrop Combi Dispenser (ThermoFisher) and allowed to grow overnight. The next day (day 0), a series of 9-point, 3-fold serial dilutions of compounds were prepared and dispensed into wells from a 1 mM stock solution using a TECAN digital dispenser (D300e) and the DMSO % concentration was normalized to 0.1%. Three days later, media was removed, and cells were processed as described above.

To determine $IC_{50}$ values, the ratio for each well was calculated (sDMA 800 nm value/DRAQ5 700 nm value). Each plate included 28 negative control wells (DMSO only, minimum inhibition) and 18 positive control wells for maximum inhibition (treated with 3 uM of a reference compounds, background wells). The average ratios of minimum and maximum inhibition controls were calculated and used to determine the percentage of sDMA, relative to DMSO, for each well in the plate.

These procedures generated the sDMA data in Table 7.

Cell Proliferation Assay to Determine $IC_{50}$ in Granta-519 and U-87 MG Cells

Cell Proliferation Assay to Determine $IC_{50}$ on Granta-519 Cells—Procedure 1

Granta-519 cells were maintained in PRMI 1640 (Corning Cellgro, Catalog #: 10-040-CV) medium supplemented with 10% v/v FBS (GE Healthcare, Catalog #: SH30910.03). Compounds were dissolved in DMSO to make 10 mM stocks and stored at −20° C. Nine-point, 3-fold serial dilutions were made with DMSO with top concentration at 1 mM (working stocks).

On day of experiment, compound working stocks were further diluted at 1:50 with fresh medium in 96 well plate, and 10 μL of diluted drugs were added to a new 96 well plate for proliferation assay. Cells growing at exponential phase were spun down at 1500 rpm for 4 min and resuspend in fresh medium to reach a density of $0.5 \times 10^6$ cells/ml. 200 ul of cells were added to 96 well plate containing diluted drugs and incubated for 3 days. DMSO was used a vehicle control.

On day 3, 10 μL of Cell Counting Kit-8 (CCK-8, Jojindo, CK04-13) solution was added to a new 96 well plate. Cells incubated with drugs for 3 days were resuspended by pipetting up and down, and 100 μL of cells were transferred to 96 well plate containing CCK-8 reagent to measure viable cells. Plates were incubated in CO2 incubator for 2 hours and OD450 values were measured with a microplate reader (iMark microplate reader, Bio-Rad).

For re-plating, compound working stocks were diluted at 1:50 with fresh medium and 10 μL of diluted drugs were added to a new 96 well plate. Cells from Day 3 plate (50 ul) were added to 96 well plate containing fresh drug and additional 150 μL of fresh medium was added to reach 200 μL volume. Plate was returned to $CO_2$ incubator and incubated for 3 more days. Viable cells measurement and re-plating were repeated on day 6, and the final viable cells measurement was taken on day 10.

Percentage of viable cells, relative to DMSO vehicle control, were calculated and plotted in Graphpad Prism ([Inhibitor]vs. normalized response–Variable slope) to determine proliferation $IC_{50}$ values on day 10.

Cell Proliferation Assay to Determine $IC_{50}$ in Granta-519 and U-87 MG Cells—Procedure 2

One day before experiment, Granta-519 cells were passaged to a density of $0.5 \times 10^6$ cells/ml. U-87 MG cells were trypsinized and 2,000 cells were seeded into 96-well plates and allow to grow overnight. On the day of experiment (day 0), Granta-519 Cells were spun down at 1,500 rpm for 4 min, resuspended in fresh medium to $0.5 \times 10^6$ cells/ml and 190 ul of cells were added to 96 well plates. For U-87 MG cells, old medium was removed and replaced with 190 uL fresh medium. Compound working stocks were first diluted at 1:50 with fresh medium in 96 well plate and 10 μL of diluted drugs were added to 96 well plates containing cells and incubated for 3 days. DMSO was used a vehicle control.

One day 3, 50 uL of Granta-519 cells were transferred to a new 96-well plate and 140 uL fresh medium was added. For U-87 MG cells, old medium was removed and replaced with 190 uL fresh medium. Compound working stocks were freshly diluted at 1:50 with medium and 10 μL of diluted drugs were added to cells and grow for 3 additional days.

The same process was repeated on day 6. Cells were allowed to grow for additional 4 days.

On day 10, 100 uL Granta-519 cells were transferred to a new 96 well plate and 10 μL of Cell Counting Kit-8 (CCK-8, Jojindo, CK04-13) solution was added. For U-87 MG cells, old medium was removed and replaced with 100 uL fresh medium and 10 uL CCK-8 solution was added. Plates were incubated in $CO_2$ incubator for 2 hours (Granta-519 cells) or 30 min (U-87 MG cells) and OD450 values were measured with a microplate reader (iMark microplate reader, Bio-Rad). Percentage of viable cells, relative to DMSO vehicle control, were calculated and plotted in Graphpad Prism ([Inhibitor]vs. normalized response–Variable slope) to determine proliferation $IC_{50}$ values on day 10.

These cell proliferation procedures produced the data in Table 7.

3 compounds via oral gauge (p.o.) (N=2 per sex). It showed average $T_{1/2}$ of 0.46 hr, Vss of 1.81 L/kg, blood clearance of 59.2 mL/min/kg in the i.v. male group; It showed average $T_{1/2}$ of 1.69 hr, Vss of 1.91 L/kg, blood clearance of 21.6 mL/min/kg in the i.v. female group; it showed average dose normalized AUC of 144 ng*h*kg/mL/mg and 51.1% of oral bioavailability in the male p.o. group; it showed average dose normalized AUC of 1143 ng*h*kg/mL/mg and >100% of oral bioavailability in the female p.o. group.

In a rat (SD, male and female, non-fasted) non-crossover PK study, Example 11 was dosed at 1 mg/kg (DMA: 20% HPBCD=5:95, solution) via i.v. administration (N=3 per sex) and 3 mg/kg (0.5% Na CMC+0.5% Tween80, suspension) via oral gauge (p.o.) (N=3 per sex). It showed average $T_{1/2}$ of 1.06 hr, Vss of 2.85 L/kg, blood clearance of 77.5 mL/min/kg in the i.v. male group; It showed average $T_{1/2}$ of

TABLE 7

Biochemical and cellular potency (in Granta-519 and U87 MG cell line) *

| Ex. No | Flash Plate $IC_{50}$ μM | N | HotSpot $IC_{50}$ μM | N | sDMA_Granta $IC_{50}$ μM | N | Prolif_Granta $IC_{50}$ μM | N | sDMA_U87 $IC_{50}$ μM | N | Prolif_U87 $IC_{50}$ μM | N |
|---|---|---|---|---|---|---|---|---|---|---|---|---|
| 1 | 0.0062 | 4 | 0.003 | 1 | 0.022 | 3 | 0.038 | 2 | | | | |
| 2 | 0.0041 | 3 | 0.002 | 1 | 0.02 | 2 | 0.035 | 1 | | | | |
| 6 | 0.0028 | 2 | 0.0007 | 1 | 0.038 | 2 | 0.067 | 2 | 0.094 | 1 | 0.115 | 1 |
| 9 | 0.0243 | 2 | 0.005 | 2 | | | | | 0.11 | 1 | 0.388 | 1 |
| 11 | 0.0068 | 14 | 0.003 | 1 | 0.033 | 2 | 0.092 | 2 | 0.053 | 2 | 0.206 | 2 |
| 14 | 0.0044 | 1 | 0.006 | 2 | 0.203 | 1 | | | | | | |
| 20 | 0.121 | 1 | 0.032 | 1 | | | | | | | | |
| 21 | 0.148 | 1 | 0.153 | 1 | | | | | | | | |
| 22 | 0.189 | 1 | 0.057 | 1 | | | | | | | | |
| 23 | 0.697 | 1 | | | | | | | | | | |
| 35 | 0.287 | 1 | 0.046 | 1 | | | | | | | | |
| 36 | 0.02 | 1 | 0.011 | 1 | 3.78 | 1 | 1.1 | 1 | | | | |
| 37 | 0.031 | 1 | 0.012 | 1 | | | | | | | | |
| 38 | 0.221 | 1 | 0.368 | 1 | | | | | | | | |
| 39 | 1.24 | 1 | | | | | | | | | | |
| 40 | 1.03 | 1 | | | | | | | | | | |
| 41 | 0.23 | 1 | | | | | | | | | | |
| 42 | 0.392 | 1 | | | | | | | | | | |
| 43 | 0.181 | 1 | | | | | | | | | | |
| 44 | 0.0237 | 1 | | | | | | | | 0.113 | 1 | 1.16 | 1 |
| 45 | 0.0066 | 1 | | | | | | | | 0.054 | 1 | 0.547 | 1 |
| 46 | 2.06 | 1 | | | | | | | | | | |
| 47 | 0.274 | 1 | | | | | | | | | | |
| 48 | 0.074 | 1 | | | 0.337 | 1 | | | 0.758 | 2 | 10 | 1 |
| 49 | 0.078 | 1 | | | 0.375 | 1 | | | 0.625 | 2 | 10 | 1 |
| 50 | 2.52 | 1 | | | | | | | | | | |
| 51 | 0.051 | 1 | | | | | | | | | | |
| 52 | 0.0093 | 1 | 0.009 | 1 | 1.7 | 1 | 0.396 | 1 | | | | |
| 53 | 0.134 | 1 | 0.164 | 1 | 5.24 | 2 | 10 | 1 | | | | |
| 54 | 0.0376 | 1 | | | 0.759 | 1 | 1.01 | 1 | | | | |
| 55 | 0.2 | 1 | | | | | | | | | | |
| 56 | 0.0176 | 1 | | | 0.923 | 1 | 50 | 1 | | | | |

* Initial testing of Example 1 gave an $IC_{50}$ of 0.0063 μM (N = 3; flash plate); sDMS (Granta) $IC_{50}$ of 0.009 μM (N = 1), and Prolif_(Granta) $IC_{50}$ uM of 0.028 (N = 1). Initial testing of Example 2 gave an $IC_{50}$ of 0.0042 μM (N = 1; flash plate). Initial testing of Example 11 gave an $IC_{50}$ of 0.0059 μM (N = 1; flash plate).

In Vivo Pharmacokinetic Properties of Example 1, 6 and 11

In a rat (SD, male, non-fasted) non-crossover cassette (n=2) PK study, Example 1 was dosed at 0.5 mg/kg (DMA: 200% HPBCD=5:95, solution) with another compound via i.v. administration (N=3) and 2 mg/kg (0.5% o Na CMC+ 0.50% Tween80, suspension) with another compound via oral gauge (p.o.) (N=3). It showed average $T_{1/2}$ of 0.35 hr, Vss of 1.36 L/kg, blood clearance of 56.2 mL/min/kg in the i.v. group; it showed average dose normalized AUC of 145 ng*h*kg/mL/mg and 4800 of oral bioavailability in the p.o. group.

In a rat (SD, male and female, non-fasted) non-crossover cassette (n=4) PK study, Example 6 was dosed at 0.2 mg/kg (DMA: 200% HPBCD=5:95, solution) with other 3 compounds via i.v. administration (N=2 per sex) and 2 mg/kg (0.5% o Na CMC+0.50% Tween80, suspension) with other 1.84 hr, Vss of 2.71 L/kg, blood clearance of 37.2 mL/min/kg in the i.v. female group; it showed average dose normalized AUC of 33 ng*h*kg/mL/mg and 13% of oral bioavailability in the male p.o. group; it showed average dose normalized AUC of 434 ng*h*kg/mL/mg and 97% of oral bioavailability in the female p.o. group.

In Vivo Brain Exposure of Example 2,6 and 11.

In a mouse (CD-1, male) brain exposure cassette study, Examples 2 and 6 were dosed together at 10 mg/kg each (0.5% Na CMC+0.5% Tween80, solution) via oral gauge (p.o.). At 3 time points (N=3), 2h, 4h and 8h, plasma and brain samples were analyzed for average drug concentrations.

| CMPD | Plasma-2 h ng/mL | Plasma-4 h ng/mL | Plasma-8 h ng/mL | Brain-2 h ng/g | Brain-4 h ng/g | Brain-8 h ng/g |
|---|---|---|---|---|---|---|
| Ex. 2 | 1610 | 802 | 178 | 244 | 174 | 76.2 |
| Ex. 6 | 380 | 138 | 33.7 | 183 | 45.9 | 50.5 |

In a mouse (CD-1, male) brain exposure study, Examples 11 was dosed at 10 mg/kg each (0.5% Na CMC+0.5% Tween80, solution) via oral gauge (p.o.). At 3 time points (N=3), 1 h, 2h and 4h, plasma and brain samples were analyzed for average drug concentrations.

| CMPD | Plasma-1 h ng/mL | Plasma-2 h ng/mL | Plasma-4 h ng/mL | Brain-1 h ng/g | Brain-2 h ng/g | Brain-4 h ng/g |
|---|---|---|---|---|---|---|
| Ex. 11 | 207 | 148 | 53.6 | 188 | 85.7 | 50.2 |

In Vivo Tumor Growth Inhibition of Example 1 in Granta-519 Mouse Xenograft Model.

Granta-519 cells was maintained in DMEM medium supplemented with 10% fetal bovine serum and 2 mM L-Glutamine at 37° C. in an atmosphere of 5% $CO_2$ in air. Cells in exponential growth phase were harvested and $1 \times 10^7$ cells in 0.1 mL of PBS with Matrigel (1:1) were injected subcutaneously at the right lower flank region of each mouse for tumor development. The treatments were started when the mean tumor size reaches approximately 300-400 $mm^3$. Mice were assigned into groups using StudyDirector™ software (Studylog Systems, Inc. CA, USA) and one optimal randomization design (generated by either Matched distribution or Stratified method) that shows minimal group to group variation in tumor volume was selected for group allocation. Example 1 or vehicle (0.5% Na CMC+0.5% Tween80, suspension) were administered orally (BID or QD for Example 1, QD for vehicle) at a dose of 25 mg/kg BID and 50 mg/kg QD for 16 and 20 days, respectively. Body weights and tumor size were measured every 3 to 4 days after randomization. Animals were euthanized 12 hours after last dosing, and blood and tumor samples were collected for analysis.

Following this protocol, Example 1 showed an average of 76.7% (N=5) tumor growth inhibition at 25 mg/kg BID with body weight loss of 6.75%; an average of 5.8% tumor growth inhibition at 50 mg/kg QD with body weight gain of 10.1%.

In Vivo Tumor Growth Inhibition of Example 11 in U87 MG Mouse Orthotopic Model.

U87MG-luc3 human glioblastoma cells were grown to mid-log phase in Eagle's Minimum Essential Medium containing 10% fetal bovine serum, 2 mM glutamine, 1× non-essential amino acids, 0.075% sodium bicarbonate, 1 mM sodium pyruvate, 100 units/mL sodium penicillin G, g/mL gentamicin, and 100 µg/mL streptomycin sulfate. The tumor cells were cultured in tissue culture flasks in a humidified incubator at 37° C., in an atmosphere of 5% $CO_2$ and 95% air. Cells were cultured in 2 µg/mL puromycin until the second to last passage before implant, grown to mid-log phase and harvested. Post-implant verification of luciferase-expressing cells was performed by maintaining cells in culture for three passages after implant to ensure stable doubling time. Limiting dilution was used to verify and quantitate light production in the presence of luciferin. Cells were harvested at mid-log phase and resuspended at a concentration of $1 \times 10^8$ cells/mL in PBS. Each mouse (Female athymic nude mice (Crl:NU(NCr)-Foxn1nu, Charles River)) received an intracranial injection of $1 \times 10^6$ U87MG-luc3 cells (0.01 mL cell suspension) and tumor growth was monitored through whole body bioluminescent imaging. Four days post cell implant, designated as Day 1 of the study, the animals were sorted into five groups based on flux values before treatment starts. Ex. 11 or vehicle (0.5% Na CMC+0.5% Tween80) was administered orally BID. Ex. 11 was dosed at 10, 20 mg/kg BID and 50 mg/kg BID, 7-day on/7-day off for 22 days. Animals were continued to be observed to obtain overall survival data.

In Vivo bioluminescence images (dorsal) were captured to monitor tumor progression. Luciferase activity was measured in live animals using IVIS SpectrumCT (Perkin Elmer, Mass.) equipped with a CCD camera (cooled at −90° C.), mounted on a light-tight specimen chamber. Regions of interest were drawn around each mouse image, and flux was quantified and reported as $10^6$ photons per second (p/s). For overall survival, animals were monitored individually to an endpoint of moribundity due to progression of systemic lymphoma. Full hind limb paralysis, severe ocular proptosis or moribundity all called for euthanasia.

Ex. 11 showed an average (N=6-8) of 10%, 61%, and 85% of tumor growth inhibition at 10, 20, and 50 (7-day on/7-day off) mg/kg BID on day 29. The median survival for vehicle and the three treated groups are 31.5, 41, 37.5, and 39 days, respectively.

The present disclosure is also directed to the following aspects:

Aspect 1. A compound of Formula I or Formula II:

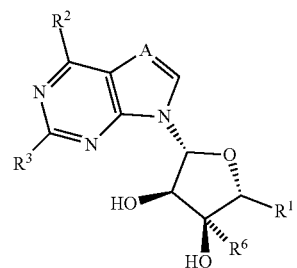

I

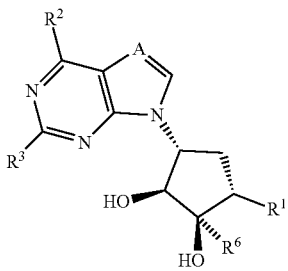

or a pharmaceutically acceptable salt or solvate thereof;
wherein
A is N, C—H or C—R$^4$ wherein R$^4$ is halo;
R$^1$ is —C$_1$-C$_6$alk-fused aryl, or —C$_1$-C$_6$alk-fused heteroaryl
R$^2$ is halo, —C$_1$-C$_6$alkyl, —C$_1$-C$_6$alk-O—C$_1$-C$_6$alkyl, —NR$^5$R$^{5'}$, —NHC(O)NR$^5$R$^{5'}$, —NHC(S)NR$^5$R$^{5'}$, —NH—O—R$^5$, or —NH—NR$^5$R$^{5'}$;
R$^3$ is H, halo, NH$_2$, or —C$_1$-C$_6$alkyl;
R$^5$ and R$^{5'}$ are each independently H, C$_1$-C$_6$alkyl, or —C$_1$-C$_6$alk-OC$_1$-C$_6$alkyl; or R$^5$ and R$^{5'}$, together with the atom to which they are attached, form a C$_2$-C$_6$heterocycloalkyl ring; and
R$^6$ is H or —C$_1$-C$_6$alkyl.

Aspect 2. The compound of aspect 1 wherein R$^1$ is —C$_1$-C$_6$alk-fused aryl.

Aspect 3. The compound of aspect 2 wherein the fused aryl is bicyclo[4.2.0]octa-1(6),2,4-trien-3-yl, 7-fluorobicyclo[4.2.0]octa-1(6),2,4-trien-3-yl, or 7,7-difluorobicyclo[4.2.0]octa-1(6),2,4-trien-3-yl.

Aspect 4. The compound of aspect 2 wherein R$^1$ is —CH$_2$-bicyclo[4.2.0]octa-1(6),2,4-trien-3-yl, —CH$_2$-7-fluorobicyclo[4.2.0]octa-1(6),2,4-trien-3-yl, —CH$_2$-7,7-difluorobicyclo[4.2.0]octa-1(6),2,4-trien-3-yl, —CH(OH)-bicyclo[4.2.0]octa-1(6),2,4-trien-3-yl, —CH(OH)-7-fluorobicyclo[4.2.0]octa-1(6),2,4-trien-3-yl, —CH(OH)-7,7-difluorobicyclo[4.2.0]octa-1(6),2,4-trien-3-yl, —CH(F)-bicyclo[4.2.0]octa-1(6),2,4-trien-3-yl, —CH(F)-7-fluorobicyclo[4.2.0]octa-1(6),2,4-trien-3-yl, —CH(F)-7,7-difluorobicyclo[4.2.0]octa-1(6),2,4-trien-3-yl, —CH(NH$_2$)-bicyclo[4.2.0]octa-1(6),2,4-trien-3-yl, —CH(NH$_2$)-7-fluorobicyclo[4.2.0]octa-1(6),2,4-trien-3-yl, —CH(NH$_2$)-7,7-difluorobicyclo[4.2.0]octa-1(6),2,4-trien-3-yl, —CH(Me)-bicyclo[4.2.0]octa-1(6),2,4-trien-3-yl, —CH(Me)-7-fluorobicyclo[4.2.0]octa-1(6),2,4-trien-3-yl, —CH(Me)-7,7-difluorobicyclo[4.2.0]octa-1(6),2,4-trien-3-yl, —C(Me)(OH)-bicyclo[4.2.0]octa-1(6),2,4-trien-3-yl, —C(Me)(OH)-7-fluorobicyclo[4.2.0]octa-1(6),2,4-trien-3-yl, or —C(Me)(OH)-7,7-difluorobicyclo[4.2.0]octa-1(6),2,4-trien-3-yl.

Aspect 5. The compound of aspect 1 wherein R$^1$ is —C$_1$-C$_6$alk-fused heteroaryl.

Aspect 6. The compound of aspect 5 wherein the fused heteroaryl is 2,3-dihydrobenzofuran-6-yl.

Aspect 7. The compound of aspect 5, wherein R$^1$ is —CH$_2$-2,3-dihydrobenzofuran-6-yl, —CH(OH)-2,3-dihydrobenzofuran-6-yl, —CH(F)-2,3-dihydrobenzofuran-6-yl, —CH(NH$_2$)-2,3-dihydrobenzofuran-6-yl, —CH(Me)-2,3-dihydrobenzofuran-6-yl, or —C(Me)(OH)-2,3-dihydrobenzofuran-6-yl.

Aspect 8. The compound of any one of aspects 1 to 7 wherein R$^2$ is —C$_1$-C$_6$alkyl, preferably methyl.

Aspect 9. The compound of any one of aspects 1 to 7, wherein R$^2$ is —NR$^5$R$^{5'}$, and R$^5$ and R$^{5'}$ are both H.

Aspect 10. The compound of any one of aspects 1 to 7, wherein R$^2$ is —NH—O—R$^5$, and R$^5$ is H or C$_1$-C$_6$alkyl.

Aspect 11. The compound of any one of aspects 1 to 7, wherein R$^2$ is —NHC(O)NR$^5$R$^{5'}$, and R$^5$ and R$^{5'}$ are each C$_1$-C$_6$alkyl.

Aspect 12. The compound of any one of aspects 1 to 7, wherein R$^2$ is —NHC(O)NR$^5$R$^{5'}$, and R$^5$ and R$^{5'}$ together with the atom to which they are attached, form a C$_2$-C$_6$heterocycloalkyl ring.

Aspect 13. The compound of any one of aspects 1 to 12 wherein R$^3$ is H.

Aspect 14. The compound of any one of aspects 1 to 13, wherein A is N.

Aspect 15. The compound of any one of aspects 1 to 13, wherein A is C—R$^4$ and R$^4$ is H or F.

Aspect 16. The compound of any one of aspects 1 to 15, wherein R$^6$ is H.

Aspect 17. The compound of any one of aspects 1 to 15, wherein R$^6$ is —CH$_3$.

Aspect 18. The compound of any one of aspects 1 to 17, which is a compound of Formula I.

Aspect 19. The compound of any one of aspects 1 to 17, which is a compound of Formula II.

Aspect 20. A pharmaceutical composition comprising a compound according to any one of aspects 1 to 19 and a pharmaceutically acceptable excipient.

Aspect 21. A method of inhibiting a protein arginine methyltransferase 5 (PRMT5) enzyme, comprising: contacting the PRMT5 enzyme with an effective amount of a compound of any one of any one of aspects 1 to 19.

Aspect 22. A method of treating a disease or disorder associated with aberrant PRMT5 activity in a subject comprising administering to the subject, a compound of any one of aspects 1 to 19.

Aspect 23. The method of aspect 22, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

Aspect 24. The method of aspect 22 or aspect 23, wherein the compound is administered in combination with one or more other agents.

What is claimed:

1. A compound of Formula I:

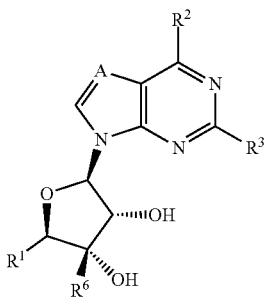

or a pharmaceutically acceptable salt thereof,
wherein:
  A is CH or $CR^4$;
  $R^1$ is $C_1$-$C_6$ alk-fused aryl;
    wherein the $C_1$-$C_6$ alk is optionally substituted with one or more substituents independently selected from the group consisting of halo, $NH_2$, and OH;
    wherein the aryl of the fused aryl is optionally substituted with one or more substituents independently selected from the group consisting of halo, $C_1$-$C_3$ alkyl, $C_1$-$C_3$ haloalkyl, $C_1$-$C_3$ alkylene-$NH_2$, $NH_2$, and $NHC(O)NH_2$; and
    wherein the non-aromatic ring of the fused aryl is optionally substituted with one or more substituents independently selected from the group consisting of halo, CN, $C_1$-$C_3$ alkyl, $C_1$-$C_3$ haloalkyl, $C_1$-$C_3$ alkylene-$N_2$, $N_2$, $NHC(O)NH_2$, OH and =O;
  $R^2$ is halo, $C_1$-$C_6$ alkyl, $C_2$-$C_4$ alkenyl, $C_1$-$C_6$ alk-halo, $C_1$-$C_6$ alk-OH, $C_1$-$C_6$ alk-O—$C_1$-$C_6$ alkyl, $C_1$-$C_6$ alk-O—$C_1$-$C_6$ alk-aryl, $NR^5R^{5'}$, $NHC(O)NR^5R^{5'}$, $NHC(S)NR^5R^{5'}$, $NHNR^5R^{5'}$, $NHOR^5$, or O—$C_1$-$C_6$ alkyl;
  $R^3$ is H, halo, $C_1$-$C_6$ alkyl, or $NH_2$;
  $R^4$ is halo or $C_1$-$C_6$ haloalkyl;
  $R^5$ is H, $C_1$-$C_6$ alkyl, or $C_1$-$C_6$ alk-O—$C_1$-$C_6$ alkyl;
  $R^{5'}$ is H, $C_1$-$C_6$ alkyl, or $C_1$-$C_6$ alk-O—$C_1$-$C_6$ alkyl; or
  $R^5$ and $R^{5'}$, together with the atom to which they are attached, form a $C_2$-$C_6$ heterocycloalkyl ring; and
  $R^6$ is H or $C_1$-$C_6$ alkyl.

2. The compound of claim 1, or a pharmaceutically acceptable salt thereof, wherein A is CH.

3. The compound of claim 1, or a pharmaceutically acceptable salt thereof, wherein the fused aryl of $R^1$ is bicyclo[4.2.0]octa-1(6),2,4-trien-3-yl, 7-fluorobicyclo[4.2.0]octa-1(6),2,4-trien-3-yl, or 7,7-difluorobicyclo[4.2.0]octa-1 (6),2,4-trien-3-yl.

4. The compound of claim 1, or a pharmaceutically acceptable salt thereof, wherein $R^1$ is $CH_2$-(bicyclo[4.2.0]octa-1(6),2,4-trien-3-yl), $CH_2$-(7-fluorobicyclo[4.2.0]octa-1(6),2,4-trien-3-yl), $CH_2$-(7,7-difluorobicyclo[4.2.0]octa-1(6),2,4-trien-3-yl), CH(Me)-(bicyclo[4.2.0]octa-1 (6),2,4-trien-3-yl), CH(Me)-(7-fluorobicyclo[4.2.0]octa-1 (6),2,4-trien-3-yl), CH(Me)-(7,7-difluorobicyclo[4.2.0]octa-1 (6),2,4-trien-3-yl), CH(F)-(bicyclo[4.2.0]octa-1 (6),2,4-trien-3-yl), CH(F)-(7-fluorobicyclo[4.2.0]octa-1 (6),2,4-trien-3-yl), CH(F)-(7,7-difluorobicyclo[4.2.0]octa-1 (6),2,4-trien-3-yl), $CH(NH_2)$-(bicyclo[4.2]octa-1 (6),2,4-trien-3-yl), $CH(NH_2)$-(7-fluorobicyclo[4.2.0]octa-1 (6),2,4-trien-3-yl), $CH(NH_2)$-(7,7-difluorobicyclo[4.2.0]octa-1 (6),2,4-trien-3-yl), CH(OH)-(bicyclo[4.2.0]octa-1 (6),2,4-trien-3-yl), CH(OH)-(7-fluorobicyclo[4.2.0]octa-1 (6),2,4-trien-3-yl), CH(OH)-(7,7-difluorobicyclo[4.2]octa-1 (6),2,4-trien-3-yl), C(Me)(OH)-(bicyclo[4.2.0]octa-1 (6),2,4-trien-3-yl), C(Me)(OH)-(7-fluorobicyclo[4.2.0]octa-1 (6),2,4-trien-3-yl), or —C(Me)(OH)-(7,7-difluorobicyclo[4.2.0]octa-1(6),2,4-trien-3-yl).

5. The compound of claim 1, or a pharmaceutically acceptable salt thereof, wherein $R^2$ is $C_1$-$C_6$ alkyl.

6. The compound of claim 1, or a pharmaceutically acceptable salt thereof, wherein:
  $R^2$ is $NR^5R^{5'}$;
  $R^5$ is H; and
  $R^{5'}$ is H.

7. The compound of claim 1, or a pharmaceutically acceptable salt thereof, wherein:
  $R^2$ is $NR^5R^{5'}$;
  $R^5$ is $CH_3$; and
  $R^{5'}$ is H.

8. The compound of claim 1, or a pharmaceutically acceptable salt thereof, wherein:
  $R^2$ is $NHOR^5$; and
  $R^5$ is H or $C_1$-$C_6$ alkyl.

9. The compound of claim 1, or a pharmaceutically acceptable salt thereof, wherein $R^3$ is H.

10. The compound of claim 1, or a pharmaceutically acceptable salt thereof, wherein $R^6$ is H.

11. The compound of claim 1, or a pharmaceutically acceptable salt thereof, wherein $R^6$ is $CH_3$.

12. The compound of claim 1, wherein the compound is:

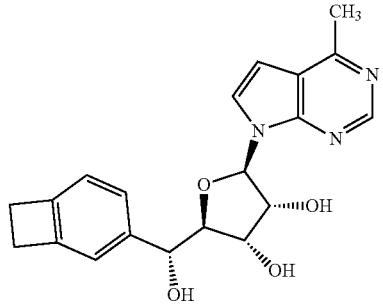 [SMILES: Cc1ncnc2c1ccn2[C@@H]1O[C@H]([C@H](O)c2ccc3c(c2)CC3)[C@@H](O)[C@H]1O]

or a pharmaceutically acceptable salt thereof.

13. A pharmaceutical composition comprising a pharmaceutically acceptable excipient and a compound of claim 1, or a pharmaceutically acceptable salt thereof.

14. The pharmaceutical composition of claim 13, wherein the compound is:

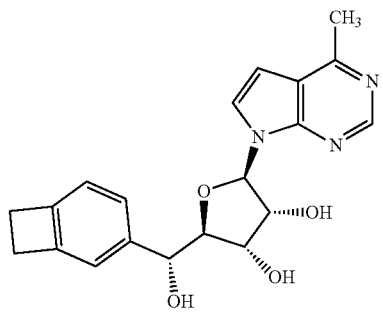 [SMILES: Cc1ncnc2c1ccn2[C@@H]1O[C@H]([C@H](O)c2ccc3c(c2)CC3)[C@@H](O)[C@H]1O]

or a pharmaceutically acceptable salt thereof.

15. A method for inhibiting a protein arginine methyltransferase 5 (PRMT5) enzyme in a cell, wherein the method comprises contacting the protein arginine methyltransferase 5 enzyme in the cell with an effective amount of a compound of claim 1, or a pharmaceutically acceptable salt thereof.

16. The method of claim 15, wherein the compound is:

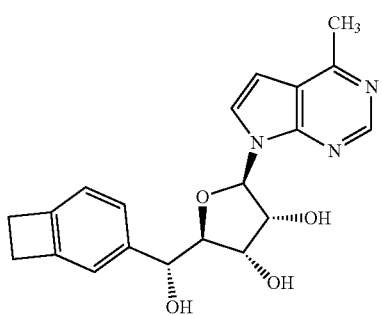 [SMILES: Cc1ncnc2c1ccn2[C@@H]1O[C@H]([C@H](O)c2ccc3c(c2)CC3)[C@@H](O)[C@H]1O]

or a pharmaceutically acceptable salt thereof.

17. A method for inhibiting a protein arginine methyltransferase 5 (PRMT5) enzyme in a subject, wherein the method comprises administering to the subject in need thereof an effective amount of a compound of claim 1, or a pharmaceutically acceptable salt thereof.

18. The method of claim 17, wherein the subject has a disease or disorder associated with aberrant protein arginine methyltransferase 5 activity selected from the group consisting of bladder cancer, breast cancer, a chromosome 9p deleted cancer, a cyclin dependent kinase inhibitor 2A (CDKN2A) deleted cancer, cervical cancer, colon cancer, epidermoid cancer, glioblastoma multiforme, head and neck cancer, a hemoglobinopathy, hepatocellular carcinoma, leukemia, lung cancer, mastocytosis, a methylthioadenosine phosphorylase (MTAP) deleted cancer, multiple myeloma, myelodysplasia, myelodysplastic syndrome, a myeloproliferative disorder, ovarian cancer, pancreatic cancer, prostate cancer, and uterine cancer.

19. The method of claim 18, wherein the leukemia is selected from the group consisting of acute lymphocytic leukemia, acute myelogenous leukemia, chronic lymphocytic leukemia, chronic myelogenous leukemia, and hairy cell leukemia,.

20. The method of claim 18, wherein the hemoglobinopathy is beta-thalassemia or sickle cell disease.

21. The method of claim 18, wherein the lung cancer is non-small cell lung cancer.

22. The method of claim 17, wherein the compound is:

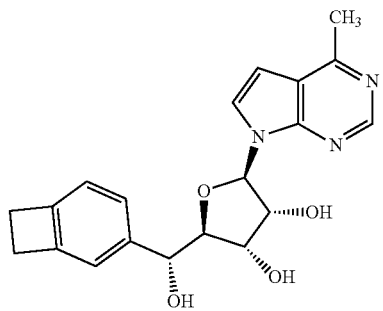 [SMILES: Cc1ncnc2c1ccn2[C@@H]1O[C@H]([C@H](O)c2ccc3c(c2)CC3)[C@@H](O)[C@H]1O]

or a pharmaceutically acceptable salt thereof.

23. The method of claim 17, wherein the method further comprises administering to the subject in need thereof an effective amount of the compound of claim 1, or a pharmaceutically acceptable salt thereof, in combination with one or more other agents.

* * * * *